UnitedStates Patent
Schwartz et al.

(10) Patent No.: US 10,265,380 B2
(45) Date of Patent: Apr. 23, 2019

(54) METHOD OF ADMINISTERING MANF FOR THE PROTECTION OF SENSORY CELLS

(71) Applicants: University of Massachusetts, Boston, MA (US); Amarantus Bioscience Holdings, Inc., San Francisco, CA (US)

(72) Inventors: Lawrence M. Schwartz, Pelham, MA (US); Gerald Commissiong, Hummelstown, PA (US); David A. Lowe, Vevey (CH); Roman Urfer, Belmont, CA (US)

(73) Assignees: Amarantus Bioscience Holdings, Inc., San Francisco, CA (US); University of Massachusetts, Boston, MA (US)

( * ) Notice: Subject to any disclaimer, the term of this patent is extended or adjusted under 35 U.S.C. 154(b) by 0 days.

(21) Appl. No.: 15/123,238

(22) PCT Filed: Mar. 3, 2015

(86) PCT No.: PCT/US2015/018470
§ 371 (c)(1),
(2) Date: Sep. 1, 2016

(87) PCT Pub. No.: WO2015/134485
PCT Pub. Date: Sep. 11, 2015

(65) Prior Publication Data
US 2017/0072015 A1    Mar. 16, 2017

Related U.S. Application Data

(60) Provisional application No. 61/948,343, filed on Mar. 5, 2014, provisional application No. 62/084,279, filed on Nov. 25, 2014.

(51) Int. Cl.
*A61K 38/18*    (2006.01)

(52) U.S. Cl.
CPC .................. *A61K 38/185* (2013.01)

(58) Field of Classification Search
None
See application file for complete search history.

(56) References Cited

FOREIGN PATENT DOCUMENTS

| JP | H11504351 A | 4/1999 |
| JP | 2005220070 A | 8/2005 |
| JP | 2017508793 A | 3/2017 |
| WO | WO-1997030722 A1 | 8/1997 |
| WO | WO-2011075838 A1 | 6/2011 |
| WO | WO-2012170918 A2 | 12/2012 |
| WO | WO-2013034805 A1 | 3/2013 |
| WO | WO-2015134485 A1 | 9/2015 |

OTHER PUBLICATIONS

Mätlik et al., Cell Death and Disease (2015) 6, e2032; doi:10.1038/cddis.2015.371. (Year: 2015).*
Tokuriki and Tawflik, Current Opinion in Structural Biology 2009, 19: 596-604. (Year: 2009).*
Phillips, A., J Pharm Pharmacology, 2001; 53: 1169-1174. (Year: 2001).*
Jafarlou et al., Journal of Biological Regulators & Homeostatic Agents, 2016: 30: 315-321. (Year: 2016).*
Tadros et al., Apoptosis, 2008; 13: 1303-1321. (Year: 2008).*
Cheng, L, et al., "Overexpression of conserved dopamine neurotrophic factor (CDNF) in astrocytes alleviates endoplasmic reticulum stress-induced cell damage and inflammatory cytokine secretion", Biochemical and Biophysical Research Communications, vol. 435, (2013), 34-39.
Roehm, P C, et al., "Strategies to preserve or regenerate spiral ganglion neurons", Current Opinion in Otolaryngology & Head and Neck Surgery, vol. 13, (2005), 294-300.
"International Application Serial No. PCT/US2015/018470, International Search Report dated Jun. 3, 2015", 5 pgs.
"International Application Serial No. PCT/US2015/018470, Written Opinion dated Jun. 3, 2015", 5 pgs.
Hellman, M, et al., "Mesencephalic Astrocyte-derived Neurotrophic Factor (MANF) Has a Unique Mechanism to Rescue Apoptotic Neurons", The Journal of Biological Chemistry, vol. 286, (2011), 8 pgs.
Yu, Y-Q, et al., "Induction profile of MANF/ARMET by cerebral ischemia and its implication for neuron protection", Journal of Cerebral Blood Flow & Metabolism, vol. 30, (2010), 79-91.
"European Application Serial No. 15759074.6, Response Filed Mar. 23, 2017 to Communication pursuant to Rules 161(2) and 162 EPC dated Nov. 25, 2016", 4 pgs.
"International Application Serial No. PCT/US2015/018470, International Preliminary Report on Patentability dated Sep. 15, 2016", 7 pgs.
"European Application Serial No. 15759074.6, Extended European Search Report dated Sep. 18, 2017", 9 pgs.
Chaoshi, Niu, et al., "Does neurotrophic factor benefit to PD therapy via co-function with ubiquitinproteasome system?", Medical Hypotheses, Eden Press, Penrith, US, vol. 76, No. 4, (Jan. 6, 2011), 589-592.
"Japanese Application Serial No. 2016-573670, Notification of Reasons for Refusal dated Nov. 20, 2018", W/ English Translation, 9 pgs.
Hellman, M, et al., "Mesencephalic astrocyte-derived neur otrophic factor (MANF) has a unique mechanism to rescue apoptotic Neurons.", Biol Chem, (Jan. 28, 2011), 2675-2685 pgs.

* cited by examiner

*Primary Examiner* — Christina M Borgeest
(74) *Attorney, Agent, or Firm* — Schwegman Lundberg & Woessner, P.A.

(57) ABSTRACT

Disclosed herein are methods of treating or preventing cell death-related sensory cell loss in a subject in need thereof, the method comprising administering an effective amount of one or more neuroprotective peptides to the subject. Also disclosed are methods of treating or preventing drug-induced ototoxicity in a subject in need thereof, the method comprising administering an effective amount of one or more neuroprotective peptides to the subject.

8 Claims, 4 Drawing Sheets
Specification includes a Sequence Listing.

SEQUENCE LISTING

```
<160> NUMBER OF SEQ ID NOS: 187

<210> SEQ ID NO 1
<211> LENGTH: 185
<212> TYPE: PRT
<213> ORGANISM: Homo sapiens

<400> SEQUENCE: 1

Met Arg Arg Met Arg Arg Met Trp Ala Thr Gln Gly Leu Ala Val Ala
1               5                   10                  15

Leu Ala Leu Ser Val Leu Pro Gly Ser Arg Ala Leu Arg Pro Gly Asp
            20                  25                  30

Cys Glu Val Cys Ile Ser Tyr Leu Gly Arg Phe Tyr Gln Asp Leu Lys
        35                  40                  45

Asp Arg Asp Val Thr Phe Ser Pro Ala Thr Ile Glu Asn Glu Leu Ile
    50                  55                  60

Lys Phe Cys Arg Glu Ala Arg Gly Lys Glu Asn Arg Leu Cys Tyr Tyr
65                  70                  75                  80

Ile Gly Ala Thr Asp Asp Ala Ala Thr Lys Ile Ile Asn Glu Val Ser
                85                  90                  95

Lys Pro Leu Ala His His Ile Pro Val Glu Lys Ile Cys Glu Lys Leu
            100                 105                 110

Lys Lys Lys Asp Ser Gln Ile Cys Glu Leu Lys Tyr Asp Lys Gln Ile
        115                 120                 125

Asp Leu Ser Thr Val Asp Leu Lys Lys Leu Arg Val Lys Glu Leu Lys
    130                 135                 140
```

Lys Ile Leu Asp Asp Trp Gly Glu Thr Cys Lys Gly Cys Ala Glu Lys
145                 150                 155                 160

Ser Asp Tyr Ile Arg Lys Ile Asn Glu Leu Met Pro Lys Tyr Ala Pro
                165                 170                 175

Lys Ala Ala Ser Ala Arg Thr Asp Leu
            180                 185

<210> SEQ ID NO 2
<211> LENGTH: 179
<212> TYPE: PRT
<213> ORGANISM: Homo sapiens

<400> SEQUENCE: 2

Met Trp Ala Thr Gln Gly Leu Ala Val Ala Leu Ser Val Leu
1               5                   10                  15

Pro Gly Ser Arg Ala Leu Arg Pro Gly Asp Cys Glu Val Cys Ile Ser
                20                  25                  30

Tyr Leu Gly Arg Phe Tyr Gln Asp Leu Lys Asp Arg Asp Val Thr Phe
                35                  40                  45

Ser Pro Ala Thr Ile Glu Asn Glu Leu Ile Lys Phe Cys Arg Glu Ala
50                  55                  60

Arg Gly Lys Glu Asn Arg Leu Cys Tyr Tyr Ile Gly Ala Thr Asp Asp
65                  70                  75                  80

Ala Ala Thr Lys Ile Ile Asn Glu Val Ser Lys Pro Leu Ala His His
                85                  90                  95

Ile Pro Val Glu Lys Ile Cys Glu Lys Leu Lys Lys Lys Asp Ser Gln
                100                 105                 110

Ile Cys Glu Leu Lys Tyr Asp Lys Gln Ile Asp Leu Ser Thr Val Asp
                115                 120                 125

Leu Lys Lys Leu Arg Val Lys Glu Leu Lys Lys Ile Leu Asp Asp Trp
130                 135                 140

Gly Glu Thr Cys Lys Gly Cys Ala Glu Lys Ser Asp Tyr Ile Arg Lys
145                 150                 155                 160

Ile Asn Glu Leu Met Pro Lys Tyr Ala Pro Lys Ala Ala Ser Ala Arg
                165                 170                 175

Thr Asp Leu

<210> SEQ ID NO 3
<211> LENGTH: 158
<212> TYPE: PRT
<213> ORGANISM: Homo sapiens

<400> SEQUENCE: 3

Leu Arg Pro Gly Asp Cys Glu Val Cys Ile Ser Tyr Leu Gly Arg Phe
1               5                   10                  15

Tyr Gln Asp Leu Lys Asp Arg Asp Val Thr Phe Ser Pro Ala Thr Ile
                20                  25                  30

Glu Asn Glu Leu Ile Lys Phe Cys Arg Glu Ala Arg Gly Lys Glu Asn
                35                  40                  45

Arg Leu Cys Tyr Tyr Ile Gly Ala Thr Asp Asp Ala Ala Thr Lys Ile
            50                  55                  60

Ile Asn Glu Val Ser Lys Pro Leu Ala His His Ile Pro Val Glu Lys
65                  70                  75                  80

Ile Cys Glu Lys Leu Lys Lys Lys Asp Ser Gln Ile Cys Glu Leu Lys
                85                  90                  95

```
Tyr Asp Lys Gln Ile Asp Leu Ser Thr Val Asp Leu Lys Lys Leu Arg
            100                 105                 110

Val Lys Glu Leu Lys Lys Ile Leu Asp Asp Trp Gly Glu Thr Cys Lys
        115                 120                 125

Gly Cys Ala Glu Lys Ser Asp Tyr Ile Arg Lys Ile Asn Glu Leu Met
    130                 135                 140

Pro Lys Tyr Ala Pro Lys Ala Ala Ser Ala Arg Thr Asp Leu
145                 150                 155
```

<210> SEQ ID NO 4
<211> LENGTH: 159
<212> TYPE: PRT
<213> ORGANISM: Homo sapiens

<400> SEQUENCE: 4

```
Met Leu Arg Pro Gly Asp Cys Glu Val Cys Ile Ser Tyr Leu Gly Arg
1               5                   10                  15

Phe Tyr Gln Asp Leu Lys Asp Arg Asp Val Thr Phe Ser Pro Ala Thr
            20                  25                  30

Ile Glu Asn Glu Leu Ile Lys Phe Cys Arg Glu Ala Arg Gly Lys Glu
        35                  40                  45

Asn Arg Leu Cys Tyr Tyr Ile Gly Ala Thr Asp Asp Ala Ala Thr Lys
    50                  55                  60

Ile Ile Asn Glu Val Ser Lys Pro Leu Ala His His Ile Pro Val Glu
65                  70                  75                  80

Lys Ile Cys Glu Lys Leu Lys Lys Lys Asp Ser Gln Ile Cys Glu Leu
                85                  90                  95

Lys Tyr Asp Lys Gln Ile Asp Leu Ser Thr Val Asp Leu Lys Lys Leu
            100                 105                 110

Arg Val Lys Glu Leu Lys Lys Ile Leu Asp Asp Trp Gly Glu Thr Cys
        115                 120                 125

Lys Gly Cys Ala Glu Lys Ser Asp Tyr Ile Arg Lys Ile Asn Glu Leu
    130                 135                 140

Met Pro Lys Tyr Ala Pro Lys Ala Ala Ser Ala Arg Thr Asp Leu
145                 150                 155
```

<210> SEQ ID NO 5
<211> LENGTH: 187
<212> TYPE: PRT
<213> ORGANISM: Homo sapiens

<400> SEQUENCE: 5

```
Met Trp Cys Ala Ser Pro Val Ala Val Ala Phe Cys Ala Gly Leu
1               5                   10                  15

Leu Val Ser His Pro Val Leu Thr Gln Gly Gln Glu Ala Gly Gly Arg
            20                  25                  30

Pro Gly Ala Asp Cys Glu Val Cys Lys Glu Phe Leu Asn Arg Phe Tyr
        35                  40                  45

Lys Ser Leu Ile Asp Arg Gly Val Asn Phe Ser Leu Asp Thr Ile Glu
    50                  55                  60

Lys Glu Leu Ile Ser Phe Cys Leu Asp Thr Lys Gly Lys Glu Asn Arg
65                  70                  75                  80

Leu Cys Tyr Tyr Leu Gly Ala Thr Lys Asp Ala Ala Thr Lys Ile Leu
                85                  90                  95

Ser Glu Val Thr Arg Pro Met Ser Val His Met Pro Ala Met Lys Ile
            100                 105                 110
```

```
Cys Glu Lys Leu Lys Lys Leu Asp Ser Gln Ile Cys Glu Leu Lys Tyr
            115                 120                 125

Glu Lys Thr Leu Asp Leu Ala Ser Val Asp Leu Arg Lys Met Arg Val
        130                 135                 140

Ala Glu Leu Lys Gln Ile Leu His Ser Trp Gly Glu Glu Cys Arg Ala
145                 150                 155                 160

Cys Ala Glu Lys Thr Asp Tyr Val Asn Leu Ile Gln Glu Leu Ala Pro
                165                 170                 175

Lys Tyr Ala Ala Thr His Pro Lys Thr Glu Leu
                180                 185

<210> SEQ ID NO 6
<211> LENGTH: 161
<212> TYPE: PRT
<213> ORGANISM: Homo sapiens

<400> SEQUENCE: 6

Gln Glu Ala Gly Gly Arg Pro Gly Ala Asp Cys Glu Val Cys Lys Glu
1               5                   10                  15

Phe Leu Asn Arg Phe Tyr Lys Ser Leu Ile Asp Arg Gly Val Asn Phe
            20                  25                  30

Ser Leu Asp Thr Ile Glu Lys Glu Leu Ile Ser Phe Cys Leu Asp Thr
        35                  40                  45

Lys Gly Lys Glu Asn Arg Leu Cys Tyr Tyr Leu Gly Ala Thr Lys Asp
    50                  55                  60

Ala Ala Thr Lys Ile Leu Ser Glu Val Thr Arg Pro Met Ser Val His
65                  70                  75                  80

Met Pro Ala Met Lys Ile Cys Glu Lys Leu Lys Lys Leu Asp Ser Gln
                85                  90                  95

Ile Cys Glu Leu Lys Tyr Glu Lys Thr Leu Asp Leu Ala Ser Val Asp
            100                 105                 110

Leu Arg Lys Met Arg Val Ala Glu Leu Lys Gln Ile Leu His Ser Trp
        115                 120                 125

Gly Glu Glu Cys Arg Ala Cys Ala Glu Lys Thr Asp Tyr Val Asn Leu
    130                 135                 140

Ile Gln Glu Leu Ala Pro Lys Tyr Ala Ala Thr His Pro Lys Thr Glu
145                 150                 155                 160

Leu

<210> SEQ ID NO 7
<211> LENGTH: 162
<212> TYPE: PRT
<213> ORGANISM: Homo sapiens

<400> SEQUENCE: 7

Met Gln Glu Ala Gly Gly Arg Pro Gly Ala Asp Cys Glu Val Cys Lys
1               5                   10                  15

Glu Phe Leu Asn Arg Phe Tyr Lys Ser Leu Ile Asp Arg Gly Val Asn
            20                  25                  30

Phe Ser Leu Asp Thr Ile Glu Lys Glu Leu Ile Ser Phe Cys Leu Asp
        35                  40                  45

Thr Lys Gly Lys Glu Asn Arg Leu Cys Tyr Tyr Leu Gly Ala Thr Lys
    50                  55                  60

Asp Ala Ala Thr Lys Ile Leu Ser Glu Val Thr Arg Pro Met Ser Val
65                  70                  75                  80

His Met Pro Ala Met Lys Ile Cys Glu Lys Leu Lys Lys Leu Asp Ser
```

```
                    85                  90                  95

Gln Ile Cys Glu Leu Lys Tyr Glu Lys Thr Leu Asp Leu Ala Ser Val
            100                 105                 110

Asp Leu Arg Lys Met Arg Val Ala Glu Leu Lys Gln Ile Leu His Ser
            115                 120                 125

Trp Gly Glu Glu Cys Arg Ala Cys Ala Glu Lys Thr Asp Tyr Val Asn
        130                 135                 140

Leu Ile Gln Glu Leu Ala Pro Lys Tyr Ala Ala Thr His Pro Lys Thr
145                 150                 155                 160

Glu Leu

<210> SEQ ID NO 8
<211> LENGTH: 40
<212> TYPE: PRT
<213> ORGANISM: Homo sapiens

<400> SEQUENCE: 8

Ile Leu Asp Asp Trp Gly Glu Thr Cys Lys Gly Cys Ala Glu Lys Ser
1               5                   10                  15

Asp Tyr Ile Arg Lys Ile Asn Glu Leu Met Pro Lys Tyr Ala Pro Lys
            20                  25                  30

Ala Ala Ser Ala Arg Thr Asp Leu
        35                  40

<210> SEQ ID NO 9
<211> LENGTH: 39
<212> TYPE: PRT
<213> ORGANISM: Homo sapiens

<400> SEQUENCE: 9

Leu Asp Asp Trp Gly Glu Thr Cys Lys Gly Cys Ala Glu Lys Ser Asp
1               5                   10                  15

Tyr Ile Arg Lys Ile Asn Glu Leu Met Pro Lys Tyr Ala Pro Lys Ala
            20                  25                  30

Ala Ser Ala Arg Thr Asp Leu
        35

<210> SEQ ID NO 10
<211> LENGTH: 38
<212> TYPE: PRT
<213> ORGANISM: Homo sapiens

<400> SEQUENCE: 10

Asp Asp Trp Gly Glu Thr Cys Lys Gly Cys Ala Glu Lys Ser Asp Tyr
1               5                   10                  15

Ile Arg Lys Ile Asn Glu Leu Met Pro Lys Tyr Ala Pro Lys Ala Ala
            20                  25                  30

Ser Ala Arg Thr Asp Leu
        35

<210> SEQ ID NO 11
<211> LENGTH: 37
<212> TYPE: PRT
<213> ORGANISM: Homo sapiens

<400> SEQUENCE: 11

Asp Trp Gly Glu Thr Cys Lys Gly Cys Ala Glu Lys Ser Asp Tyr Ile
1               5                   10                  15

Arg Lys Ile Asn Glu Leu Met Pro Lys Tyr Ala Pro Lys Ala Ala Ser
```

Ala Arg Thr Asp Leu
        35

<210> SEQ ID NO 12
<211> LENGTH: 36
<212> TYPE: PRT
<213> ORGANISM: Homo sapiens

<400> SEQUENCE: 12

Trp Gly Glu Thr Cys Lys Gly Cys Ala Glu Lys Ser Asp Tyr Ile Arg
1               5                   10                  15

Lys Ile Asn Glu Leu Met Pro Lys Tyr Ala Pro Lys Ala Ala Ser Ala
            20                  25                  30

Arg Thr Asp Leu
        35

<210> SEQ ID NO 13
<211> LENGTH: 35
<212> TYPE: PRT
<213> ORGANISM: Homo sapiens

<400> SEQUENCE: 13

Gly Glu Thr Cys Lys Gly Cys Ala Glu Lys Ser Asp Tyr Ile Arg Lys
1               5                   10                  15

Ile Asn Glu Leu Met Pro Lys Tyr Ala Pro Lys Ala Ala Ser Ala Arg
            20                  25                  30

Thr Asp Leu
        35

<210> SEQ ID NO 14
<211> LENGTH: 34
<212> TYPE: PRT
<213> ORGANISM: Homo sapiens

<400> SEQUENCE: 14

Glu Thr Cys Lys Gly Cys Ala Glu Lys Ser Asp Tyr Ile Arg Lys Ile
1               5                   10                  15

Asn Glu Leu Met Pro Lys Tyr Ala Pro Lys Ala Ala Ser Ala Arg Thr
            20                  25                  30

Asp Leu

<210> SEQ ID NO 15
<211> LENGTH: 33
<212> TYPE: PRT
<213> ORGANISM: Homo sapiens

<400> SEQUENCE: 15

Thr Cys Lys Gly Cys Ala Glu Lys Ser Asp Tyr Ile Arg Lys Ile Asn
1               5                   10                  15

Glu Leu Met Pro Lys Tyr Ala Pro Lys Ala Ala Ser Ala Arg Thr Asp
            20                  25                  30

Leu

<210> SEQ ID NO 16
<211> LENGTH: 32
<212> TYPE: PRT
<213> ORGANISM: Homo sapiens

<400> SEQUENCE: 16

Cys Lys Gly Cys Ala Glu Lys Ser Asp Tyr Ile Arg Lys Ile Asn Glu
1               5                   10                  15

Leu Met Pro Lys Tyr Ala Pro Lys Ala Ala Ser Ala Arg Thr Asp Leu
            20                  25                  30

<210> SEQ ID NO 17
<211> LENGTH: 15
<212> TYPE: PRT
<213> ORGANISM: Homo sapiens

<400> SEQUENCE: 17

Cys Lys Gly Cys Ala Glu Lys Ser Asp Tyr Ile Arg Lys Ile Asn
1               5                   10                  15

<210> SEQ ID NO 18
<211> LENGTH: 15
<212> TYPE: PRT
<213> ORGANISM: Homo sapiens

<400> SEQUENCE: 18

Thr Cys Lys Gly Cys Ala Glu Lys Ser Asp Tyr Ile Arg Lys Ile
1               5                   10                  15

<210> SEQ ID NO 19
<211> LENGTH: 15
<212> TYPE: PRT
<213> ORGANISM: Homo sapiens

<400> SEQUENCE: 19

Glu Thr Cys Lys Gly Cys Ala Glu Lys Ser Asp Tyr Ile Arg Lys
1               5                   10                  15

<210> SEQ ID NO 20
<211> LENGTH: 15
<212> TYPE: PRT
<213> ORGANISM: Homo sapiens

<400> SEQUENCE: 20

Gly Glu Thr Cys Lys Gly Cys Ala Glu Lys Ser Asp Tyr Ile Arg
1               5                   10                  15

<210> SEQ ID NO 21
<211> LENGTH: 15
<212> TYPE: PRT
<213> ORGANISM: Homo sapiens

<400> SEQUENCE: 21

Trp Gly Glu Thr Cys Lys Gly Cys Ala Glu Lys Ser Asp Tyr Ile
1               5                   10                  15

<210> SEQ ID NO 22
<211> LENGTH: 15
<212> TYPE: PRT
<213> ORGANISM: Homo sapiens

<400> SEQUENCE: 22

Asp Trp Gly Glu Thr Cys Lys Gly Cys Ala Glu Lys Ser Asp Tyr
1               5                   10                  15

<210> SEQ ID NO 23
<211> LENGTH: 15
<212> TYPE: PRT
<213> ORGANISM: Homo sapiens

<400> SEQUENCE: 23

```
Asp Asp Trp Gly Glu Thr Cys Lys Gly Cys Ala Glu Lys Ser Asp
1               5                  10                  15

<210> SEQ ID NO 24
<211> LENGTH: 15
<212> TYPE: PRT
<213> ORGANISM: Homo sapiens

<400> SEQUENCE: 24

Leu Asp Asp Trp Gly Glu Thr Cys Lys Gly Cys Ala Glu Lys Ser
1               5                  10                  15

<210> SEQ ID NO 25
<211> LENGTH: 15
<212> TYPE: PRT
<213> ORGANISM: Homo sapiens

<400> SEQUENCE: 25

Ile Leu Asp Asp Trp Gly Glu Thr Cys Lys Gly Cys Ala Glu Lys
1               5                  10                  15

<210> SEQ ID NO 26
<211> LENGTH: 15
<212> TYPE: PRT
<213> ORGANISM: Homo sapiens

<400> SEQUENCE: 26

Lys Ile Leu Asp Asp Trp Gly Glu Thr Cys Lys Gly Cys Ala Glu
1               5                  10                  15

<210> SEQ ID NO 27
<211> LENGTH: 15
<212> TYPE: PRT
<213> ORGANISM: Homo sapiens

<400> SEQUENCE: 27

Lys Lys Ile Leu Asp Asp Trp Gly Glu Thr Cys Lys Gly Cys Ala
1               5                  10                  15

<210> SEQ ID NO 28
<211> LENGTH: 15
<212> TYPE: PRT
<213> ORGANISM: Homo sapiens

<400> SEQUENCE: 28

Leu Lys Lys Ile Leu Asp Asp Trp Gly Glu Thr Cys Lys Gly Cys
1               5                  10                  15

<210> SEQ ID NO 29
<211> LENGTH: 14
<212> TYPE: PRT
<213> ORGANISM: Homo sapiens

<400> SEQUENCE: 29

Cys Lys Gly Cys Ala Glu Lys Ser Asp Tyr Ile Arg Lys Ile
1               5                  10

<210> SEQ ID NO 30
<211> LENGTH: 14
<212> TYPE: PRT
<213> ORGANISM: Homo sapiens

<400> SEQUENCE: 30

Thr Cys Lys Gly Cys Ala Glu Lys Ser Asp Tyr Ile Arg Lys
```

<210> SEQ ID NO 31
<211> LENGTH: 14
<212> TYPE: PRT
<213> ORGANISM: Homo sapiens

<400> SEQUENCE: 31

Glu Thr Cys Lys Gly Cys Ala Glu Lys Ser Asp Tyr Ile Arg
1               5                   10

<210> SEQ ID NO 32
<211> LENGTH: 14
<212> TYPE: PRT
<213> ORGANISM: Homo sapiens

<400> SEQUENCE: 32

Gly Glu Thr Cys Lys Gly Cys Ala Glu Lys Ser Asp Tyr Ile
1               5                   10

<210> SEQ ID NO 33
<211> LENGTH: 14
<212> TYPE: PRT
<213> ORGANISM: Homo sapiens

<400> SEQUENCE: 33

Trp Gly Glu Thr Cys Lys Gly Cys Ala Glu Lys Ser Asp Tyr
1               5                   10

<210> SEQ ID NO 34
<211> LENGTH: 14
<212> TYPE: PRT
<213> ORGANISM: Homo sapiens

<400> SEQUENCE: 34

Asp Trp Gly Glu Thr Cys Lys Gly Cys Ala Glu Lys Ser Asp
1               5                   10

<210> SEQ ID NO 35
<211> LENGTH: 14
<212> TYPE: PRT
<213> ORGANISM: Homo sapiens

<400> SEQUENCE: 35

Asp Asp Trp Gly Glu Thr Cys Lys Gly Cys Ala Glu Lys Ser
1               5                   10

<210> SEQ ID NO 36
<211> LENGTH: 14
<212> TYPE: PRT
<213> ORGANISM: Homo sapiens

<400> SEQUENCE: 36

Leu Asp Asp Trp Gly Glu Thr Cys Lys Gly Cys Ala Glu Lys
1               5                   10

<210> SEQ ID NO 37
<211> LENGTH: 14
<212> TYPE: PRT
<213> ORGANISM: Homo sapiens

<400> SEQUENCE: 37

Ile Leu Asp Asp Trp Gly Glu Thr Cys Lys Gly Cys Ala Glu
1               5                   10

```
<210> SEQ ID NO 38
<211> LENGTH: 14
<212> TYPE: PRT
<213> ORGANISM: Homo sapiens

<400> SEQUENCE: 38

Lys Ile Leu Asp Asp Trp Gly Glu Thr Cys Lys Gly Cys Ala
1               5                   10

<210> SEQ ID NO 39
<211> LENGTH: 14
<212> TYPE: PRT
<213> ORGANISM: Homo sapiens

<400> SEQUENCE: 39

Lys Lys Ile Leu Asp Asp Trp Gly Glu Thr Cys Lys Gly Cys
1               5                   10

<210> SEQ ID NO 40
<211> LENGTH: 13
<212> TYPE: PRT
<213> ORGANISM: Homo sapiens

<400> SEQUENCE: 40

Cys Lys Gly Cys Ala Glu Lys Ser Asp Tyr Ile Arg Lys
1               5                   10

<210> SEQ ID NO 41
<211> LENGTH: 13
<212> TYPE: PRT
<213> ORGANISM: Homo sapiens

<400> SEQUENCE: 41

Thr Cys Lys Gly Cys Ala Glu Lys Ser Asp Tyr Ile Arg
1               5                   10

<210> SEQ ID NO 42
<211> LENGTH: 13
<212> TYPE: PRT
<213> ORGANISM: Homo sapiens

<400> SEQUENCE: 42

Glu Thr Cys Lys Gly Cys Ala Glu Lys Ser Asp Tyr Ile
1               5                   10

<210> SEQ ID NO 43
<211> LENGTH: 13
<212> TYPE: PRT
<213> ORGANISM: Homo sapiens

<400> SEQUENCE: 43

Gly Glu Thr Cys Lys Gly Cys Ala Glu Lys Ser Asp Tyr
1               5                   10

<210> SEQ ID NO 44
<211> LENGTH: 13
<212> TYPE: PRT
<213> ORGANISM: Homo sapiens

<400> SEQUENCE: 44

Trp Gly Glu Thr Cys Lys Gly Cys Ala Glu Lys Ser Asp
1               5                   10

<210> SEQ ID NO 45
```

```
<211> LENGTH: 13
<212> TYPE: PRT
<213> ORGANISM: Homo sapiens

<400> SEQUENCE: 45

Asp Trp Gly Glu Thr Cys Lys Gly Cys Ala Glu Lys Ser
1               5                   10

<210> SEQ ID NO 46
<211> LENGTH: 13
<212> TYPE: PRT
<213> ORGANISM: Homo sapiens

<400> SEQUENCE: 46

Asp Asp Trp Gly Glu Thr Cys Lys Gly Cys Ala Glu Lys
1               5                   10

<210> SEQ ID NO 47
<211> LENGTH: 13
<212> TYPE: PRT
<213> ORGANISM: Homo sapiens

<400> SEQUENCE: 47

Leu Asp Asp Trp Gly Glu Thr Cys Lys Gly Cys Ala Glu
1               5                   10

<210> SEQ ID NO 48
<211> LENGTH: 13
<212> TYPE: PRT
<213> ORGANISM: Homo sapiens

<400> SEQUENCE: 48

Ile Leu Asp Asp Trp Gly Glu Thr Cys Lys Gly Cys Ala
1               5                   10

<210> SEQ ID NO 49
<211> LENGTH: 13
<212> TYPE: PRT
<213> ORGANISM: Homo sapiens

<400> SEQUENCE: 49

Lys Ile Leu Asp Asp Trp Gly Glu Thr Cys Lys Gly Cys
1               5                   10

<210> SEQ ID NO 50
<211> LENGTH: 12
<212> TYPE: PRT
<213> ORGANISM: Homo sapiens

<400> SEQUENCE: 50

Cys Lys Gly Cys Ala Glu Lys Ser Asp Tyr Ile Arg
1               5                   10

<210> SEQ ID NO 51
<211> LENGTH: 12
<212> TYPE: PRT
<213> ORGANISM: Homo sapiens

<400> SEQUENCE: 51

Thr Cys Lys Gly Cys Ala Glu Lys Ser Asp Tyr Ile
1               5                   10

<210> SEQ ID NO 52
<211> LENGTH: 12
<212> TYPE: PRT
```

<213> ORGANISM: Homo sapiens

<400> SEQUENCE: 52

Glu Thr Cys Lys Gly Cys Ala Glu Lys Ser Asp Tyr
1               5                   10

<210> SEQ ID NO 53
<211> LENGTH: 12
<212> TYPE: PRT
<213> ORGANISM: Homo sapiens

<400> SEQUENCE: 53

Gly Glu Thr Cys Lys Gly Cys Ala Glu Lys Ser Asp
1               5                   10

<210> SEQ ID NO 54
<211> LENGTH: 12
<212> TYPE: PRT
<213> ORGANISM: Homo sapiens

<400> SEQUENCE: 54

Trp Gly Glu Thr Cys Lys Gly Cys Ala Glu Lys Ser
1               5                   10

<210> SEQ ID NO 55
<211> LENGTH: 12
<212> TYPE: PRT
<213> ORGANISM: Homo sapiens

<400> SEQUENCE: 55

Asp Trp Gly Glu Thr Cys Lys Gly Cys Ala Glu Lys
1               5                   10

<210> SEQ ID NO 56
<211> LENGTH: 12
<212> TYPE: PRT
<213> ORGANISM: Homo sapiens

<400> SEQUENCE: 56

Asp Asp Trp Gly Glu Thr Cys Lys Gly Cys Ala Glu
1               5                   10

<210> SEQ ID NO 57
<211> LENGTH: 12
<212> TYPE: PRT
<213> ORGANISM: Homo sapiens

<400> SEQUENCE: 57

Leu Asp Asp Trp Gly Glu Thr Cys Lys Gly Cys Ala
1               5                   10

<210> SEQ ID NO 58
<211> LENGTH: 12
<212> TYPE: PRT
<213> ORGANISM: Homo sapiens

<400> SEQUENCE: 58

Ile Leu Asp Asp Trp Gly Glu Thr Cys Lys Gly Cys
1               5                   10

<210> SEQ ID NO 59
<211> LENGTH: 11
<212> TYPE: PRT
<213> ORGANISM: Homo sapiens

```
<400> SEQUENCE: 59

Cys Lys Gly Cys Ala Glu Lys Ser Asp Tyr Ile
1               5                   10

<210> SEQ ID NO 60
<211> LENGTH: 11
<212> TYPE: PRT
<213> ORGANISM: Homo sapiens

<400> SEQUENCE: 60

Thr Cys Lys Gly Cys Ala Glu Lys Ser Asp Tyr
1               5                   10

<210> SEQ ID NO 61
<211> LENGTH: 11
<212> TYPE: PRT
<213> ORGANISM: Homo sapiens

<400> SEQUENCE: 61

Glu Thr Cys Lys Gly Cys Ala Glu Lys Ser Asp
1               5                   10

<210> SEQ ID NO 62
<211> LENGTH: 11
<212> TYPE: PRT
<213> ORGANISM: Homo sapiens

<400> SEQUENCE: 62

Gly Glu Thr Cys Lys Gly Cys Ala Glu Lys Ser
1               5                   10

<210> SEQ ID NO 63
<211> LENGTH: 11
<212> TYPE: PRT
<213> ORGANISM: Homo sapiens

<400> SEQUENCE: 63

Trp Gly Glu Thr Cys Lys Gly Cys Ala Glu Lys
1               5                   10

<210> SEQ ID NO 64
<211> LENGTH: 11
<212> TYPE: PRT
<213> ORGANISM: Homo sapiens

<400> SEQUENCE: 64

Asp Trp Gly Glu Thr Cys Lys Gly Cys Ala Glu
1               5                   10

<210> SEQ ID NO 65
<211> LENGTH: 11
<212> TYPE: PRT
<213> ORGANISM: Homo sapiens

<400> SEQUENCE: 65

Asp Asp Trp Gly Glu Thr Cys Lys Gly Cys Ala
1               5                   10

<210> SEQ ID NO 66
<211> LENGTH: 11
<212> TYPE: PRT
<213> ORGANISM: Homo sapiens

<400> SEQUENCE: 66
```

```
Leu Asp Asp Trp Gly Glu Thr Cys Lys Gly Cys
1               5                   10
```

<210> SEQ ID NO 67
<211> LENGTH: 10
<212> TYPE: PRT
<213> ORGANISM: Homo sapiens

<400> SEQUENCE: 67

```
Cys Lys Gly Cys Ala Glu Lys Ser Asp Tyr
1               5                   10
```

<210> SEQ ID NO 68
<211> LENGTH: 10
<212> TYPE: PRT
<213> ORGANISM: Homo sapiens

<400> SEQUENCE: 68

```
Thr Cys Lys Gly Cys Ala Glu Lys Ser Asp
1               5                   10
```

<210> SEQ ID NO 69
<211> LENGTH: 10
<212> TYPE: PRT
<213> ORGANISM: Homo sapiens

<400> SEQUENCE: 69

```
Glu Thr Cys Lys Gly Cys Ala Glu Lys Ser
1               5                   10
```

<210> SEQ ID NO 70
<211> LENGTH: 10
<212> TYPE: PRT
<213> ORGANISM: Homo sapiens

<400> SEQUENCE: 70

```
Gly Glu Thr Cys Lys Gly Cys Ala Glu Lys
1               5                   10
```

<210> SEQ ID NO 71
<211> LENGTH: 10
<212> TYPE: PRT
<213> ORGANISM: Homo sapiens

<400> SEQUENCE: 71

```
Trp Gly Glu Thr Cys Lys Gly Cys Ala Glu
1               5                   10
```

<210> SEQ ID NO 72
<211> LENGTH: 10
<212> TYPE: PRT
<213> ORGANISM: Homo sapiens

<400> SEQUENCE: 72

```
Asp Trp Gly Glu Thr Cys Lys Gly Cys Ala
1               5                   10
```

<210> SEQ ID NO 73
<211> LENGTH: 10
<212> TYPE: PRT
<213> ORGANISM: Homo sapiens

<400> SEQUENCE: 73

```
Asp Asp Trp Gly Glu Thr Cys Lys Gly Cys
1               5                   10
```

<210> SEQ ID NO 74
<211> LENGTH: 9
<212> TYPE: PRT
<213> ORGANISM: Homo sapiens

<400> SEQUENCE: 74

Cys Lys Gly Cys Ala Glu Lys Ser Asp
1               5

<210> SEQ ID NO 75
<211> LENGTH: 9
<212> TYPE: PRT
<213> ORGANISM: Homo sapiens

<400> SEQUENCE: 75

Thr Cys Lys Gly Cys Ala Glu Lys Ser
1               5

<210> SEQ ID NO 76
<211> LENGTH: 9
<212> TYPE: PRT
<213> ORGANISM: Homo sapiens

<400> SEQUENCE: 76

Glu Thr Cys Lys Gly Cys Ala Glu Lys
1               5

<210> SEQ ID NO 77
<211> LENGTH: 9
<212> TYPE: PRT
<213> ORGANISM: Homo sapiens

<400> SEQUENCE: 77

Gly Glu Thr Cys Lys Gly Cys Ala Glu
1               5

<210> SEQ ID NO 78
<211> LENGTH: 9
<212> TYPE: PRT
<213> ORGANISM: Homo sapiens

<400> SEQUENCE: 78

Trp Gly Glu Thr Cys Lys Gly Cys Ala
1               5

<210> SEQ ID NO 79
<211> LENGTH: 9
<212> TYPE: PRT
<213> ORGANISM: Homo sapiens

<400> SEQUENCE: 79

Asp Trp Gly Glu Thr Cys Lys Gly Cys
1               5

<210> SEQ ID NO 80
<211> LENGTH: 8
<212> TYPE: PRT
<213> ORGANISM: Homo sapiens

<400> SEQUENCE: 80

Cys Lys Gly Cys Ala Glu Lys Ser
1               5

```
<210> SEQ ID NO 81
<211> LENGTH: 8
<212> TYPE: PRT
<213> ORGANISM: Homo sapiens

<400> SEQUENCE: 81

Thr Cys Lys Gly Cys Ala Glu Lys
1               5

<210> SEQ ID NO 82
<211> LENGTH: 8
<212> TYPE: PRT
<213> ORGANISM: Homo sapiens

<400> SEQUENCE: 82

Glu Thr Cys Lys Gly Cys Ala Glu
1               5

<210> SEQ ID NO 83
<211> LENGTH: 8
<212> TYPE: PRT
<213> ORGANISM: Homo sapiens

<400> SEQUENCE: 83

Gly Glu Thr Cys Lys Gly Cys Ala
1               5

<210> SEQ ID NO 84
<211> LENGTH: 8
<212> TYPE: PRT
<213> ORGANISM: Homo sapiens

<400> SEQUENCE: 84

Trp Gly Glu Thr Cys Lys Gly Cys
1               5

<210> SEQ ID NO 85
<211> LENGTH: 7
<212> TYPE: PRT
<213> ORGANISM: Homo sapiens

<400> SEQUENCE: 85

Cys Lys Gly Cys Ala Glu Lys
1               5

<210> SEQ ID NO 86
<211> LENGTH: 7
<212> TYPE: PRT
<213> ORGANISM: Homo sapiens

<400> SEQUENCE: 86

Thr Cys Lys Gly Cys Ala Glu
1               5

<210> SEQ ID NO 87
<211> LENGTH: 7
<212> TYPE: PRT
<213> ORGANISM: Homo sapiens

<400> SEQUENCE: 87

Glu Thr Cys Lys Gly Cys Ala
1               5

<210> SEQ ID NO 88
<211> LENGTH: 7
```

```
<212> TYPE: PRT
<213> ORGANISM: Homo sapiens

<400> SEQUENCE: 88

Gly Glu Thr Cys Lys Gly Cys
 1               5

<210> SEQ ID NO 89
<211> LENGTH: 6
<212> TYPE: PRT
<213> ORGANISM: Homo sapiens

<400> SEQUENCE: 89

Cys Lys Gly Cys Ala Glu
 1               5

<210> SEQ ID NO 90
<211> LENGTH: 6
<212> TYPE: PRT
<213> ORGANISM: Homo sapiens

<400> SEQUENCE: 90

Thr Cys Lys Gly Cys Ala
 1               5

<210> SEQ ID NO 91
<211> LENGTH: 6
<212> TYPE: PRT
<213> ORGANISM: Homo sapiens

<400> SEQUENCE: 91

Glu Thr Cys Lys Gly Cys
 1               5

<210> SEQ ID NO 92
<211> LENGTH: 5
<212> TYPE: PRT
<213> ORGANISM: Homo sapiens

<400> SEQUENCE: 92

Cys Lys Gly Cys Ala
 1               5

<210> SEQ ID NO 93
<211> LENGTH: 5
<212> TYPE: PRT
<213> ORGANISM: Homo sapiens

<400> SEQUENCE: 93

Thr Cys Lys Gly Cys
 1               5

<210> SEQ ID NO 94
<211> LENGTH: 4
<212> TYPE: PRT
<213> ORGANISM: Homo sapiens

<400> SEQUENCE: 94

Cys Lys Gly Cys
 1

<210> SEQ ID NO 95
<211> LENGTH: 40
<212> TYPE: PRT
<213> ORGANISM: Homo sapiens
```

```
<400> SEQUENCE: 95

Lys Gln Ile Leu His Ser Trp Gly Glu Glu Cys Arg Ala Cys Ala Glu
1               5                   10                  15

Lys Thr Asp Tyr Val Asn Leu Ile Gln Glu Leu Ala Pro Lys Tyr Ala
                20                  25                  30

Ala Thr His Pro Lys Thr Glu Leu
            35                  40

<210> SEQ ID NO 96
<211> LENGTH: 39
<212> TYPE: PRT
<213> ORGANISM: Homo sapiens

<400> SEQUENCE: 96

Gln Ile Leu His Ser Trp Gly Glu Glu Cys Arg Ala Cys Ala Glu Lys
1               5                   10                  15

Thr Asp Tyr Val Asn Leu Ile Gln Glu Leu Ala Pro Lys Tyr Ala Ala
                20                  25                  30

Thr His Pro Lys Thr Glu Leu
            35

<210> SEQ ID NO 97
<211> LENGTH: 38
<212> TYPE: PRT
<213> ORGANISM: Homo sapiens

<400> SEQUENCE: 97

Ile Leu His Ser Trp Gly Glu Glu Cys Arg Ala Cys Ala Glu Lys Thr
1               5                   10                  15

Asp Tyr Val Asn Leu Ile Gln Glu Leu Ala Pro Lys Tyr Ala Ala Thr
                20                  25                  30

His Pro Lys Thr Glu Leu
            35

<210> SEQ ID NO 98
<211> LENGTH: 37
<212> TYPE: PRT
<213> ORGANISM: Homo sapiens

<400> SEQUENCE: 98

Leu His Ser Trp Gly Glu Glu Cys Arg Ala Cys Ala Glu Lys Thr Asp
1               5                   10                  15

Tyr Val Asn Leu Ile Gln Glu Leu Ala Pro Lys Tyr Ala Ala Thr His
                20                  25                  30

Pro Lys Thr Glu Leu
            35

<210> SEQ ID NO 99
<211> LENGTH: 36
<212> TYPE: PRT
<213> ORGANISM: Homo sapiens

<400> SEQUENCE: 99

His Ser Trp Gly Glu Glu Cys Arg Ala Cys Ala Glu Lys Thr Asp Tyr
1               5                   10                  15

Val Asn Leu Ile Gln Glu Leu Ala Pro Lys Tyr Ala Ala Thr His Pro
                20                  25                  30

Lys Thr Glu Leu
            35
```

<210> SEQ ID NO 100
<211> LENGTH: 35
<212> TYPE: PRT
<213> ORGANISM: Homo sapiens

<400> SEQUENCE: 100

Ser Trp Gly Glu Glu Cys Arg Ala Cys Ala Glu Lys Thr Asp Tyr Val
1               5                   10                  15

Asn Leu Ile Gln Glu Leu Ala Pro Lys Tyr Ala Ala Thr His Pro Lys
            20                  25                  30

Thr Glu Leu
        35

<210> SEQ ID NO 101
<211> LENGTH: 34
<212> TYPE: PRT
<213> ORGANISM: Homo sapiens

<400> SEQUENCE: 101

Trp Gly Glu Glu Cys Arg Ala Cys Ala Glu Lys Thr Asp Tyr Val Asn
1               5                   10                  15

Leu Ile Gln Glu Leu Ala Pro Lys Tyr Ala Ala Thr His Pro Lys Thr
            20                  25                  30

Glu Leu

<210> SEQ ID NO 102
<211> LENGTH: 33
<212> TYPE: PRT
<213> ORGANISM: Homo sapiens

<400> SEQUENCE: 102

Gly Glu Glu Cys Arg Ala Cys Ala Glu Lys Thr Asp Tyr Val Asn Leu
1               5                   10                  15

Ile Gln Glu Leu Ala Pro Lys Tyr Ala Ala Thr His Pro Lys Thr Glu
            20                  25                  30

Leu

<210> SEQ ID NO 103
<211> LENGTH: 32
<212> TYPE: PRT
<213> ORGANISM: Homo sapiens

<400> SEQUENCE: 103

Glu Glu Cys Arg Ala Cys Ala Glu Lys Thr Asp Tyr Val Asn Leu Ile
1               5                   10                  15

Gln Glu Leu Ala Pro Lys Tyr Ala Ala Thr His Pro Lys Thr Glu Leu
            20                  25                  30

<210> SEQ ID NO 104
<211> LENGTH: 31
<212> TYPE: PRT
<213> ORGANISM: Homo sapiens

<400> SEQUENCE: 104

Glu Cys Arg Ala Cys Ala Glu Lys Thr Asp Tyr Val Asn Leu Ile Gln
1               5                   10                  15

Glu Leu Ala Pro Lys Tyr Ala Ala Thr His Pro Lys Thr Glu Leu
            20                  25                  30

<210> SEQ ID NO 105
<211> LENGTH: 30
<212> TYPE: PRT
<213> ORGANISM: Homo sapiens

<400> SEQUENCE: 105

Cys Arg Ala Cys Ala Glu Lys Thr Asp Tyr Val Asn Leu Ile Gln Glu
1               5                   10                  15

Leu Ala Pro Lys Tyr Ala Ala Thr His Pro Lys Thr Glu Leu
            20                  25                  30

<210> SEQ ID NO 106
<211> LENGTH: 15
<212> TYPE: PRT
<213> ORGANISM: Homo sapiens

<400> SEQUENCE: 106

Leu Lys Gln Ile Leu His Ser Trp Gly Glu Glu Cys Arg Ala Cys
1               5                   10                  15

<210> SEQ ID NO 107
<211> LENGTH: 15
<212> TYPE: PRT
<213> ORGANISM: Homo sapiens

<400> SEQUENCE: 107

Lys Gln Ile Leu His Ser Trp Gly Glu Glu Cys Arg Ala Cys Ala
1               5                   10                  15

<210> SEQ ID NO 108
<211> LENGTH: 15
<212> TYPE: PRT
<213> ORGANISM: Homo sapiens

<400> SEQUENCE: 108

Gln Ile Leu His Ser Trp Gly Glu Glu Cys Arg Ala Cys Ala Glu
1               5                   10                  15

<210> SEQ ID NO 109
<211> LENGTH: 15
<212> TYPE: PRT
<213> ORGANISM: Homo sapiens

<400> SEQUENCE: 109

Ile Leu His Ser Trp Gly Glu Glu Cys Arg Ala Cys Ala Glu Lys
1               5                   10                  15

<210> SEQ ID NO 110
<211> LENGTH: 15
<212> TYPE: PRT
<213> ORGANISM: Homo sapiens

<400> SEQUENCE: 110

Leu His Ser Trp Gly Glu Glu Cys Arg Ala Cys Ala Glu Lys Thr
1               5                   10                  15

<210> SEQ ID NO 111
<211> LENGTH: 15
<212> TYPE: PRT
<213> ORGANISM: Homo sapiens

<400> SEQUENCE: 111

His Ser Trp Gly Glu Glu Cys Arg Ala Cys Ala Glu Lys Thr Asp
1               5                   10                  15

<210> SEQ ID NO 112
<211> LENGTH: 15
<212> TYPE: PRT
<213> ORGANISM: Homo sapiens

<400> SEQUENCE: 112

Ser Trp Gly Glu Glu Cys Arg Ala Cys Ala Glu Lys Thr Asp Tyr
1               5                   10                  15

<210> SEQ ID NO 113
<211> LENGTH: 15
<212> TYPE: PRT
<213> ORGANISM: Homo sapiens

<400> SEQUENCE: 113

Trp Gly Glu Glu Cys Arg Ala Cys Ala Glu Lys Thr Asp Tyr Val
1               5                   10                  15

<210> SEQ ID NO 114
<211> LENGTH: 15
<212> TYPE: PRT
<213> ORGANISM: Homo sapiens

<400> SEQUENCE: 114

Gly Glu Glu Cys Arg Ala Cys Ala Glu Lys Thr Asp Tyr Val Asn
1               5                   10                  15

<210> SEQ ID NO 115
<211> LENGTH: 15
<212> TYPE: PRT
<213> ORGANISM: Homo sapiens

<400> SEQUENCE: 115

Glu Glu Cys Arg Ala Cys Ala Glu Lys Thr Asp Tyr Val Asn Leu
1               5                   10                  15

<210> SEQ ID NO 116
<211> LENGTH: 15
<212> TYPE: PRT
<213> ORGANISM: Homo sapiens

<400> SEQUENCE: 116

Glu Cys Arg Ala Cys Ala Glu Lys Thr Asp Tyr Val Asn Leu Ile
1               5                   10                  15

<210> SEQ ID NO 117
<211> LENGTH: 15
<212> TYPE: PRT
<213> ORGANISM: Homo sapiens

<400> SEQUENCE: 117

Cys Arg Ala Cys Ala Glu Lys Thr Asp Tyr Val Asn Leu Ile Gln
1               5                   10                  15

<210> SEQ ID NO 118
<211> LENGTH: 14
<212> TYPE: PRT
<213> ORGANISM: Homo sapiens

<400> SEQUENCE: 118

Lys Gln Ile Leu His Ser Trp Gly Glu Glu Cys Arg Ala Cys
1               5                   10

<210> SEQ ID NO 119

```
<211> LENGTH: 14
<212> TYPE: PRT
<213> ORGANISM: Homo sapiens

<400> SEQUENCE: 119

Gln Ile Leu His Ser Trp Gly Glu Glu Cys Arg Ala Cys Ala
1               5                   10

<210> SEQ ID NO 120
<211> LENGTH: 14
<212> TYPE: PRT
<213> ORGANISM: Homo sapiens

<400> SEQUENCE: 120

Ile Leu His Ser Trp Gly Glu Glu Cys Arg Ala Cys Ala Glu
1               5                   10

<210> SEQ ID NO 121
<211> LENGTH: 14
<212> TYPE: PRT
<213> ORGANISM: Homo sapiens

<400> SEQUENCE: 121

Leu His Ser Trp Gly Glu Glu Cys Arg Ala Cys Ala Glu Lys
1               5                   10

<210> SEQ ID NO 122
<211> LENGTH: 14
<212> TYPE: PRT
<213> ORGANISM: Homo sapiens

<400> SEQUENCE: 122

His Ser Trp Gly Glu Glu Cys Arg Ala Cys Ala Glu Lys Thr
1               5                   10

<210> SEQ ID NO 123
<211> LENGTH: 14
<212> TYPE: PRT
<213> ORGANISM: Homo sapiens

<400> SEQUENCE: 123

Ser Trp Gly Glu Glu Cys Arg Ala Cys Ala Glu Lys Thr Asp
1               5                   10

<210> SEQ ID NO 124
<211> LENGTH: 14
<212> TYPE: PRT
<213> ORGANISM: Homo sapiens

<400> SEQUENCE: 124

Trp Gly Glu Glu Cys Arg Ala Cys Ala Glu Lys Thr Asp Tyr
1               5                   10

<210> SEQ ID NO 125
<211> LENGTH: 14
<212> TYPE: PRT
<213> ORGANISM: Homo sapiens

<400> SEQUENCE: 125

Gly Glu Glu Cys Arg Ala Cys Ala Glu Lys Thr Asp Tyr Val
1               5                   10

<210> SEQ ID NO 126
<211> LENGTH: 14
<212> TYPE: PRT
```

-continued

<213> ORGANISM: Homo sapiens

<400> SEQUENCE: 126

Glu Glu Cys Arg Ala Cys Ala Glu Lys Thr Asp Tyr Val Asn
1               5                   10

<210> SEQ ID NO 127
<211> LENGTH: 14
<212> TYPE: PRT
<213> ORGANISM: Homo sapiens

<400> SEQUENCE: 127

Glu Cys Arg Ala Cys Ala Glu Lys Thr Asp Tyr Val Asn Leu
1               5                   10

<210> SEQ ID NO 128
<211> LENGTH: 14
<212> TYPE: PRT
<213> ORGANISM: Homo sapiens

<400> SEQUENCE: 128

Cys Arg Ala Cys Ala Glu Lys Thr Asp Tyr Val Asn Leu Ile
1               5                   10

<210> SEQ ID NO 129
<211> LENGTH: 13
<212> TYPE: PRT
<213> ORGANISM: Homo sapiens

<400> SEQUENCE: 129

Gln Ile Leu His Ser Trp Gly Glu Glu Cys Arg Ala Cys
1               5                   10

<210> SEQ ID NO 130
<211> LENGTH: 13
<212> TYPE: PRT
<213> ORGANISM: Homo sapiens

<400> SEQUENCE: 130

Ile Leu His Ser Trp Gly Glu Glu Cys Arg Ala Cys Ala
1               5                   10

<210> SEQ ID NO 131
<211> LENGTH: 13
<212> TYPE: PRT
<213> ORGANISM: Homo sapiens

<400> SEQUENCE: 131

Leu His Ser Trp Gly Glu Glu Cys Arg Ala Cys Ala Glu
1               5                   10

<210> SEQ ID NO 132
<211> LENGTH: 13
<212> TYPE: PRT
<213> ORGANISM: Homo sapiens

<400> SEQUENCE: 132

His Ser Trp Gly Glu Glu Cys Arg Ala Cys Ala Glu Lys
1               5                   10

<210> SEQ ID NO 133
<211> LENGTH: 13
<212> TYPE: PRT
<213> ORGANISM: Homo sapiens

```
<400> SEQUENCE: 133

Ser Trp Gly Glu Glu Cys Arg Ala Cys Ala Glu Lys Thr
1               5                   10

<210> SEQ ID NO 134
<211> LENGTH: 13
<212> TYPE: PRT
<213> ORGANISM: Homo sapiens

<400> SEQUENCE: 134

Trp Gly Glu Glu Cys Arg Ala Cys Ala Glu Lys Thr Asp
1               5                   10

<210> SEQ ID NO 135
<211> LENGTH: 13
<212> TYPE: PRT
<213> ORGANISM: Homo sapiens

<400> SEQUENCE: 135

Gly Glu Glu Cys Arg Ala Cys Ala Glu Lys Thr Asp Tyr
1               5                   10

<210> SEQ ID NO 136
<211> LENGTH: 13
<212> TYPE: PRT
<213> ORGANISM: Homo sapiens

<400> SEQUENCE: 136

Glu Glu Cys Arg Ala Cys Ala Glu Lys Thr Asp Tyr Val
1               5                   10

<210> SEQ ID NO 137
<211> LENGTH: 13
<212> TYPE: PRT
<213> ORGANISM: Homo sapiens

<400> SEQUENCE: 137

Glu Cys Arg Ala Cys Ala Glu Lys Thr Asp Tyr Val Asn
1               5                   10

<210> SEQ ID NO 138
<211> LENGTH: 13
<212> TYPE: PRT
<213> ORGANISM: Homo sapiens

<400> SEQUENCE: 138

Cys Arg Ala Cys Ala Glu Lys Thr Asp Tyr Val Asn Leu
1               5                   10

<210> SEQ ID NO 139
<211> LENGTH: 12
<212> TYPE: PRT
<213> ORGANISM: Homo sapiens

<400> SEQUENCE: 139

Ile Leu His Ser Trp Gly Glu Glu Cys Arg Ala Cys
1               5                   10

<210> SEQ ID NO 140
<211> LENGTH: 12
<212> TYPE: PRT
<213> ORGANISM: Homo sapiens

<400> SEQUENCE: 140
```

Leu His Ser Trp Gly Glu Glu Cys Arg Ala Cys Ala
1               5                   10

<210> SEQ ID NO 141
<211> LENGTH: 12
<212> TYPE: PRT
<213> ORGANISM: Homo sapiens

<400> SEQUENCE: 141

His Ser Trp Gly Glu Glu Cys Arg Ala Cys Ala Glu
1               5                   10

<210> SEQ ID NO 142
<211> LENGTH: 12
<212> TYPE: PRT
<213> ORGANISM: Homo sapiens

<400> SEQUENCE: 142

Ser Trp Gly Glu Glu Cys Arg Ala Cys Ala Glu Lys
1               5                   10

<210> SEQ ID NO 143
<211> LENGTH: 12
<212> TYPE: PRT
<213> ORGANISM: Homo sapiens

<400> SEQUENCE: 143

Trp Gly Glu Glu Cys Arg Ala Cys Ala Glu Lys Thr
1               5                   10

<210> SEQ ID NO 144
<211> LENGTH: 12
<212> TYPE: PRT
<213> ORGANISM: Homo sapiens

<400> SEQUENCE: 144

Gly Glu Glu Cys Arg Ala Cys Ala Glu Lys Thr Asp
1               5                   10

<210> SEQ ID NO 145
<211> LENGTH: 12
<212> TYPE: PRT
<213> ORGANISM: Homo sapiens

<400> SEQUENCE: 145

Glu Glu Cys Arg Ala Cys Ala Glu Lys Thr Asp Tyr
1               5                   10

<210> SEQ ID NO 146
<211> LENGTH: 12
<212> TYPE: PRT
<213> ORGANISM: Homo sapiens

<400> SEQUENCE: 146

Glu Cys Arg Ala Cys Ala Glu Lys Thr Asp Tyr Val
1               5                   10

<210> SEQ ID NO 147
<211> LENGTH: 12
<212> TYPE: PRT
<213> ORGANISM: Homo sapiens

<400> SEQUENCE: 147

Cys Arg Ala Cys Ala Glu Lys Thr Asp Tyr Val Asn
1               5                   10

<210> SEQ ID NO 148
<211> LENGTH: 11
<212> TYPE: PRT
<213> ORGANISM: Homo sapiens

<400> SEQUENCE: 148

Leu His Ser Trp Gly Glu Glu Cys Arg Ala Cys
1               5                   10

<210> SEQ ID NO 149
<211> LENGTH: 11
<212> TYPE: PRT
<213> ORGANISM: Homo sapiens

<400> SEQUENCE: 149

His Ser Trp Gly Glu Glu Cys Arg Ala Cys Ala
1               5                   10

<210> SEQ ID NO 150
<211> LENGTH: 11
<212> TYPE: PRT
<213> ORGANISM: Homo sapiens

<400> SEQUENCE: 150

Ser Trp Gly Glu Glu Cys Arg Ala Cys Ala Glu
1               5                   10

<210> SEQ ID NO 151
<211> LENGTH: 11
<212> TYPE: PRT
<213> ORGANISM: Homo sapiens

<400> SEQUENCE: 151

Trp Gly Glu Glu Cys Arg Ala Cys Ala Glu Lys
1               5                   10

<210> SEQ ID NO 152
<211> LENGTH: 11
<212> TYPE: PRT
<213> ORGANISM: Homo sapiens

<400> SEQUENCE: 152

Gly Glu Glu Cys Arg Ala Cys Ala Glu Lys Thr
1               5                   10

<210> SEQ ID NO 153
<211> LENGTH: 11
<212> TYPE: PRT
<213> ORGANISM: Homo sapiens

<400> SEQUENCE: 153

Glu Glu Cys Arg Ala Cys Ala Glu Lys Thr Asp
1               5                   10

<210> SEQ ID NO 154
<211> LENGTH: 11
<212> TYPE: PRT
<213> ORGANISM: Homo sapiens

<400> SEQUENCE: 154

Glu Cys Arg Ala Cys Ala Glu Lys Thr Asp Tyr
1               5                   10

```
<210> SEQ ID NO 155
<211> LENGTH: 11
<212> TYPE: PRT
<213> ORGANISM: Homo sapiens

<400> SEQUENCE: 155

Cys Arg Ala Cys Ala Glu Lys Thr Asp Tyr Val
1               5                   10

<210> SEQ ID NO 156
<211> LENGTH: 10
<212> TYPE: PRT
<213> ORGANISM: Homo sapiens

<400> SEQUENCE: 156

His Ser Trp Gly Glu Glu Cys Arg Ala Cys
1               5                   10

<210> SEQ ID NO 157
<211> LENGTH: 10
<212> TYPE: PRT
<213> ORGANISM: Homo sapiens

<400> SEQUENCE: 157

Ser Trp Gly Glu Glu Cys Arg Ala Cys Ala
1               5                   10

<210> SEQ ID NO 158
<211> LENGTH: 10
<212> TYPE: PRT
<213> ORGANISM: Homo sapiens

<400> SEQUENCE: 158

Trp Gly Glu Glu Cys Arg Ala Cys Ala Glu
1               5                   10

<210> SEQ ID NO 159
<211> LENGTH: 10
<212> TYPE: PRT
<213> ORGANISM: Homo sapiens

<400> SEQUENCE: 159

Gly Glu Glu Cys Arg Ala Cys Ala Glu Lys
1               5                   10

<210> SEQ ID NO 160
<211> LENGTH: 10
<212> TYPE: PRT
<213> ORGANISM: Homo sapiens

<400> SEQUENCE: 160

Glu Glu Cys Arg Ala Cys Ala Glu Lys Thr
1               5                   10

<210> SEQ ID NO 161
<211> LENGTH: 10
<212> TYPE: PRT
<213> ORGANISM: Homo sapiens

<400> SEQUENCE: 161

Glu Cys Arg Ala Cys Ala Glu Lys Thr Asp
1               5                   10

<210> SEQ ID NO 162
<211> LENGTH: 10
```

```
<212> TYPE: PRT
<213> ORGANISM: Homo sapiens

<400> SEQUENCE: 162

Cys Arg Ala Cys Ala Glu Lys Thr Asp Tyr
1               5                   10

<210> SEQ ID NO 163
<211> LENGTH: 9
<212> TYPE: PRT
<213> ORGANISM: Homo sapiens

<400> SEQUENCE: 163

Ser Trp Gly Glu Glu Cys Arg Ala Cys
1               5

<210> SEQ ID NO 164
<211> LENGTH: 9
<212> TYPE: PRT
<213> ORGANISM: Homo sapiens

<400> SEQUENCE: 164

Trp Gly Glu Glu Cys Arg Ala Cys Ala
1               5

<210> SEQ ID NO 165
<211> LENGTH: 9
<212> TYPE: PRT
<213> ORGANISM: Homo sapiens

<400> SEQUENCE: 165

Gly Glu Glu Cys Arg Ala Cys Ala Glu
1               5

<210> SEQ ID NO 166
<211> LENGTH: 9
<212> TYPE: PRT
<213> ORGANISM: Homo sapiens

<400> SEQUENCE: 166

Glu Glu Cys Arg Ala Cys Ala Glu Lys
1               5

<210> SEQ ID NO 167
<211> LENGTH: 9
<212> TYPE: PRT
<213> ORGANISM: Homo sapiens

<400> SEQUENCE: 167

Glu Cys Arg Ala Cys Ala Glu Lys Thr
1               5

<210> SEQ ID NO 168
<211> LENGTH: 9
<212> TYPE: PRT
<213> ORGANISM: Homo sapiens

<400> SEQUENCE: 168

Cys Arg Ala Cys Ala Glu Lys Thr Asp
1               5

<210> SEQ ID NO 169
<211> LENGTH: 8
<212> TYPE: PRT
<213> ORGANISM: Homo sapiens
```

<400> SEQUENCE: 169

Trp Gly Glu Glu Cys Arg Ala Cys
1               5

<210> SEQ ID NO 170
<211> LENGTH: 8
<212> TYPE: PRT
<213> ORGANISM: Homo sapiens

<400> SEQUENCE: 170

Gly Glu Glu Cys Arg Ala Cys Ala
1               5

<210> SEQ ID NO 171
<211> LENGTH: 8
<212> TYPE: PRT
<213> ORGANISM: Homo sapiens

<400> SEQUENCE: 171

Glu Glu Cys Arg Ala Cys Ala Glu
1               5

<210> SEQ ID NO 172
<211> LENGTH: 8
<212> TYPE: PRT
<213> ORGANISM: Homo sapiens

<400> SEQUENCE: 172

Glu Cys Arg Ala Cys Ala Glu Lys
1               5

<210> SEQ ID NO 173
<211> LENGTH: 8
<212> TYPE: PRT
<213> ORGANISM: Homo sapiens

<400> SEQUENCE: 173

Cys Arg Ala Cys Ala Glu Lys Thr
1               5

<210> SEQ ID NO 174
<211> LENGTH: 7
<212> TYPE: PRT
<213> ORGANISM: Homo sapiens

<400> SEQUENCE: 174

Gly Glu Glu Cys Arg Ala Cys
1               5

<210> SEQ ID NO 175
<211> LENGTH: 7
<212> TYPE: PRT
<213> ORGANISM: Homo sapiens

<400> SEQUENCE: 175

Glu Glu Cys Arg Ala Cys Ala
1               5

<210> SEQ ID NO 176
<211> LENGTH: 7
<212> TYPE: PRT
<213> ORGANISM: Homo sapiens

<400> SEQUENCE: 176

Glu Cys Arg Ala Cys Ala Glu
1               5

<210> SEQ ID NO 177
<211> LENGTH: 7
<212> TYPE: PRT
<213> ORGANISM: Homo sapiens

<400> SEQUENCE: 177

Cys Arg Ala Cys Ala Glu Lys
1               5

<210> SEQ ID NO 178
<211> LENGTH: 6
<212> TYPE: PRT
<213> ORGANISM: Homo sapiens

<400> SEQUENCE: 178

Glu Glu Cys Arg Ala Cys
1               5

<210> SEQ ID NO 179
<211> LENGTH: 6
<212> TYPE: PRT
<213> ORGANISM: Homo sapiens

<400> SEQUENCE: 179

Glu Cys Arg Ala Cys Ala
1               5

<210> SEQ ID NO 180
<211> LENGTH: 6
<212> TYPE: PRT
<213> ORGANISM: Homo sapiens

<400> SEQUENCE: 180

Cys Arg Ala Cys Ala Glu
1               5

<210> SEQ ID NO 181
<211> LENGTH: 5
<212> TYPE: PRT
<213> ORGANISM: Homo sapiens

<400> SEQUENCE: 181

Glu Cys Arg Ala Cys
1               5

<210> SEQ ID NO 182
<211> LENGTH: 5
<212> TYPE: PRT
<213> ORGANISM: Homo sapiens

<400> SEQUENCE: 182

Cys Arg Ala Cys Ala
1               5

<210> SEQ ID NO 183
<211> LENGTH: 4
<212> TYPE: PRT
<213> ORGANISM: Homo sapiens

<400> SEQUENCE: 183

Cys Arg Ala Cys

```
<210> SEQ ID NO 184
<211> LENGTH: 993
<212> TYPE: DNA
<213> ORGANISM: Homo sapiens

<400> SEQUENCE: 184
agctacggcg cgcggccggg acttggaggc ggtgcggcgc ggcgggtgcg gttcagtcgg      60
tcggcggcgg cagcggagga ggaggaggag gaggaggatg aggaggatga ggaggatgtg     120
ggccacgcag gggctggcgg tggcgctggc tctgagcgtg ctgccgggca gccgggcgct     180
gcggccgggc gactgcgaag tttgtatttc ttatctggga agattttacc aggacctcaa     240
agacagagat gtcacattct caccagccac tattgaaaac gaacttataa agttctgccg     300
ggaagcaaga ggcaaagaga atcggttgtg ctactatatc ggggccacag atgatgcagc     360
caccaaaatc atcaatgagg tatcaaagcc tctggcccac acatccctg tggagaagat      420 ctgtgagaag cttaagaaga aggacagcca gatatgtgag cttaagtatg acaagcagat     480
cgacctgagc acagtggacc tgaagaagct ccgagttaaa gagctgaaga gattctggga     540
tgactggggg gagacatgca aaggctgtgc agaaaagtct gactacatcc ggaagataaa     600
tgaactgatg cctaaatatg cccccaaggc agccagtgca cggaccgatt tgtagtctgc     660
tcaatctctg ttgcacctga ggggaaaaa acagttcaac tgcttactcc aaaacagcc      720 ttttgtaat ttatttttta agtgggctcc tgacaatact gtatcagatg tgaagcctgg     780
agctttcctg atgatgctgg ccctacagta cccccatgag gggattccct tccttctgtt     840
gctggtgtac tctaggactt caaagtgtgt ctgggatttt tttattaaag aaaaaaatt     900 tctagctgtc cttgcagaat tatagtgaat accaaaatgg ggttttgccc caggaggctc     960
ctaaaaaaaa aaaaaaaaaa aaaaaaaaaa aaa                                  993

<210> SEQ ID NO 185
<211> LENGTH: 540
<212> TYPE: DNA
<213> ORGANISM: Homo sapiens

<400> SEQUENCE: 185
atgtgggcca cgcaggggct ggcggtggcg ctggctctga gcgtgctgcc gggcagccgg      60
gcgctgcggc cgggcgactg cgaagtttgt atttcttatc tgggaagatt ttaccaggac     120
ctcaaagaca gagatgtcac attctcacca gccactattg aaaacgaact tataaagttc     180
tgccgggaag caagaggcaa agagaatcgg ttgtgctact atatcggggc cacagatgat     240
gcagccacca aaatcatcaa tgaggtatca aagcctctgg cccaccacat ccctgtggag     300
aagatctgtg agaagcttaa gaagaaggac agccagatat gtgagcttaa gtatgacaag     360
cagatcgacc tgagcacagt ggacctgaag aagctccgag ttaaagagct gaagaagatt     420
ctggatgact gggggagac atgcaaaggc tgtgcagaaa agtctgacta catccggaag      480
ataaatgaac tgatgcctaa atatgccccc aaggcagcca gtgcacggac cgatttgtag     540

<210> SEQ ID NO 186
<211> LENGTH: 1140
<212> TYPE: DNA
<213> ORGANISM: Homo sapiens

<400> SEQUENCE: 186
gcgcgggtgg cggaggcgat tgaagctgct ggcccagcat gtggtgcgcg agcccagttg      60
```

```
ctgtggtggc cttttgcgcc gggcttttgg tctctcaccc ggtgctgacg cagggccagg      120
aggccggggg gcggccaggg gccgactgtg aagtatgtaa agaattcttg aaccgattct      180
acaagtcact gatagacaga ggagttaact tttcgctgga cactatagag aaagaattga      240
tcagtttttg cttggacacc aaaggaaaag aaaaccgcct gtgctattat ctaggagcca      300
caaaagacgc agccacaaag atcctaagtg aagtcactcg cccaatgagt gtgcatatgc      360
ctgcaatgaa gatttgtgag aagctgaaga agttggatag ccagatctgt gagctgaaat      420
atgaaaaaac actggacttg gcatcagttg acctgcggaa gatgagagtg gcagagctga      480
agcagatcct gcatagctgg ggggaggagt gcagggcctg tgcagaaaaa actgactatg      540
tgaatctcat tcaagagctg gcccccaagt atgcagcgac acaccccaaa acagagctct      600
gatctccaat gccagcacat ttgtgacttg taattagaga gaaaagtgac tctctaggat      660
atggacatgt tgattaagga taactgggaa tgcatcatat ttggtctcat gcttttttgtg     720 ttggtattat tcctcagaat tttgttacgt gggtttatga gtgaaactaa tactactgat     780
aacttacatt tgcagtgtac caaaagctaa aagttccttt ctcataagtt tcttggaatg     840
actatgccag ttttcattgc ctgtctccta aaagtgacct actgacaaat tgatggagta    900
aattgattcc aagaaagaag aaggcattca gagactcctc tctggatgca attttaaaat      960
atattggact aaaacaaaag acacaacagt cagcttatct aatgcacaac ttcaatccca     1020
aatacagaat caaagttttt tttcaagtga attttctgtt ttcactctat attgtagctc     1080
tctttggtat cagaaatggt caggcaggag tactcgtttt tcccattgga agaaacccca     1140

<210> SEQ ID NO 187
<211> LENGTH: 564
<212> TYPE: DNA
<213> ORGANISM: Homo sapiens

<400> SEQUENCE: 187
atgtggtgcg cgagcccagt tgctgtggtg gccttttgcg ccgggctttt ggtctctcac       60
ccggtgctga cgcagggcca ggaggccggg gggcggccag gggccgactg tgaagtatgt      120
aaagaattct tgaaccgatt ctacaagtca ctgatagaca gaggagttaa cttttcgctg      180
gacactatag agaaagaatt gatcagtttt tgcttggaca ccaaaggaaa agaaaaccgc      240
ctgtgctatt atctaggagc cacaaaagac gcagccacaa agatcctaag tgaagtcact      300
cgcccaatga gtgtgcatat gcctgcaatg aagatttgtg agaagctgaa gaagttggat      360
agccagatct gtgagctgaa atatgaaaaa acactggact tggcatcagt tgacctgcgg      420
aagatgagag tggcagagct gaagcagatc ctgcatagct gggggggagga gtgcagggcc     480 tgtgcagaaa aaactgacta tgtgaatctc attcaagagc tggcccccaa gtatgcagcg      540
acacacccca aaacagagct ctga                                              564
```

METHOD OF ADMINISTERING MANF FOR THE PROTECTION OF SENSORY CELLS

CROSS-REFERENCE

This application is a U.S. National Stage Filing under 35 U.S.C. 371 from International Application No. PCT/US2015/018470, filed on Mar. 3, 2015, and published as WO 2015/134485 on Sep. 11, 2015, which claims the benefit of U.S. Provisional Application No. 61/948,343, filed Mar. 5, 2014, and U.S. Provisional Application No. 62/084,279, filed Nov. 25, 2014, each of which application is incorporated herein by reference in its entirety.

BACKGROUND OF THE INVENTION

Cell death (e.g., via apoptosis, autophagy, cornification, necrosis) is a common feature of many diseases or disorders affecting sensory perception. For example, mis-regulation of cell death (e.g., apoptosis, necrosis) can cause a partial or complete loss of hearing, vision, taste, smell, or touch. Mis-regulated cell death can also cause distortions of these senses.

Cell death, most typically via apoptosis, is a common feature of many retinal degenerative diseases. This controlled type of cell death happens normally in development and some body functions, but when it happens abnormally in the retina, it can kill the cells required for light detection and vision. Mis-regulation of cell death is also implicated in acquired and genetic hearing impairment. Exposure to excessive noise can trigger cell death in terminally differentiated sensory hair cells, leading to noise-induced hearing loss. The use of therapeutic drugs, such as aminoglycoside antibiotics and cisplatin, can also result in the activation of cell death in sensory hair cells leading to hearing loss. Not only therapeutic drugs, but also industrial compounds and pharmaceutical excipients (e.g., solvents and the like) can activate cell death mechanisms inappropriately. Mis-regulated cell death can also contribute to the development of presbycusis, also known as age-related hearing loss.

There is a need in the art to develop therapies to combat sensory loss, including sensory loss caused by mis-regulation of cell death. There is also a need in the art to develop therapies to treat drug-induced ototoxicity.

SUMMARY OF THE INVENTION

In a first aspect, disclosed herein are methods of treating or preventing cell death-related hearing impairment comprising administering an effective amount of a neuroprotective peptide comprising a mesencephalic astrocyte-derived neurotrophic factor (MANF), or fragment thereof to a subject in need thereof.

In a second aspect, disclosed herein are methods of treating or preventing ototoxicity comprising administering an effective amount of a neuroprotective peptide comprising a mesencephalic astrocyte-derived neurotrophic factor (MANF), or fragment thereof to a subject in need thereof.

In either the first or second aspect, the peptide sequence of the neuroprotective peptide can comprise a sequence that has at least about 80% identity with SEQ ID NO:3. For example, the peptide sequence of the neuroprotective peptide can comprise a sequence that has at least about 90% identity with SEQ ID NO:3. In another example, the peptide sequence of the neuroprotective peptide can comprise a sequence that has at least about 95% identity with SEQ ID NO:3. In another example, the peptide sequence of the neuroprotective peptide can consist of a sequence that has at least about 80% identity with SEQ ID NO:3. In another example, the peptide sequence of the neuroprotective peptide can consist of a sequence that has at least about 90% identity with SEQ ID NO:3. In another example, the peptide sequence of the neuroprotective peptide can consist of a sequence that has at least about 95% identity with SEQ ID NO:3. In another example, the peptide sequence of the neuroprotective peptide can consist of a sequence that has 100% identity with SEQ ID NO:3.

The neuroprotective peptides of the first or second aspect can have a length that is greater than, equal to, or less than the length of SEQ ID NO:3. For example, the neuroprotective peptide can have a length that is at least 80% the length of SEQ ID NO:3. In another example, the neuroprotective peptide can have a length that is 100% the length of SEQ ID NO:3.

In either the first or second aspect, the peptide sequence of the neuroprotective peptide can consist of a sequence listed in Table 3. The neuroprotective peptide can be cell permeable.

In a third aspect, disclosed herein are methods of treating or preventing cell death-related hearing impairment comprising administering an effective amount of a neuroprotective peptide comprising a conserved dopamine neurotrophic factor (CDNF), or a fragment thereof.

In a fourth aspect, disclosed herein are methods of treating or preventing ototoxicity in a subject comprising administering an effective amount of a neuroprotective peptide comprising a conserved dopamine neurotrophic factor (CDNF), or a fragment thereof.

In either the third or fourth aspect, the peptide sequence of the neuroprotective peptide can comprise a sequence that has at least about 80% identity with SEQ ID NO:6. For example, the peptide sequence of the neuroprotective peptide can comprise a sequence that has at least about 90% identity with SEQ ID NO:6. In another example, the peptide sequence of the neuroprotective peptide can comprise a sequence that has at least about 95% identity with SEQ ID NO:6. In another example, the peptide sequence of the neuroprotective peptide can consist of a sequence that has at least about 80% identity with SEQ ID NO:6. In another example, the peptide sequence of the neuroprotective peptide can consist of a sequence that has at least about 90% identity with SEQ ID NO:6. In another example, the peptide sequence of the neuroprotective peptide can consist of a sequence that has at least about 95% identity with SEQ ID NO:6. In another example, the peptide sequence of the neuroprotective peptide can consist of a sequence that is SEQ ID NO:6.

The neuroprotective peptides of the first or second aspect can have a length that is greater than, equal to, or less than the length of SEQ ID NO:6. For example, the neuroprotective peptide can have a length that is at least 80% the length of SEQ ID NO:6. In another example, the neuroprotective peptide can have a length that is 100% the length of SEQ ID NO:6.

In either the third or fourth aspect, the peptide sequence of the neuroprotective peptide can consist of a sequence listed in Table 4. The neuroprotective peptide can be cell permeable.

In any of aspects one through four, the effective amount of the neuroprotective peptide can be in a formulation at a concentration of about 1 µMol-50 µMol. For example, the effective amount of the neuroprotective peptide can be in a formulation at a concentration of about 3 µMol-20 µMol. The effective amount can be administered in a volume of about 100 μL-500 μL of the formulation. For example, the effective amount can be administered in a volume of about 200 μL-300 μL of the formulation.

In any of aspects one through four, the effective amount of the neuroprotective peptide can be about 1 μg-500 μg. For example, the effective amount of the neuroprotective peptide can be about 5 μg-250 μg.

In any of aspects one through four, the subject can suffer from one or more symptoms comprising hearing loss, tinnitus, vertigo, instability or loss of balance, nausea, or a combination thereof. At least one of the symptoms can be improved following treatment.

In any of aspects one through four, the administering can comprise topical administration, systemic administration, intratympanic administration, intracochlear administration, transtympanic injection, or a combination thereof. For example, the administering can comprise intratympanic administration by injection or perfusion. In another example, the administering can comprise intrachochlear administration that is: by injection, with a cochlear implant, with an osmotic mini-pump, or with a reciprocating perfusion system.

In any of aspects one through four, the administering can occur prior to a therapeutic treatment with an ototoxic drug.

In any of aspects one through four, the administering can occur concurrently with a therapeutic treatment with an ototoxic drug.

In any of aspects one through four, the administering can occur after exposure to an ototoxic chemical or toxin.

In any of aspects one through four, the ototoxicity can be associated with an anesthetic, an antibiotic, an antimalarial, a cardiac medication, a chemotherapeutic agent, a diuretic, a glucocorticosteroid, an immunomodulatory drug, a mucosal protectant, a narcotic analgesic, a non-steroidal anti-inflammatory drug (NSAID), a psychopharmacologic agent, a quinine, a toxic substance, a vapor or solvent, or a combination thereof.

In any of aspects one through four, the ototoxicity can be associated with amikacin, amphotericin B, capreomycin, chloramphenicol, erythromycin, gentamycin, kanamycin, minocycline, polymyxin B, neomycin, netilimicin, streptomycin, a sulfonamide, tobramycin, vancomycin, chloroquine, hydroxychloroquine, celiprolol, flecainide, lidocaine, metoprolol, procainamide, propranolo, quinidine, bleomycine, bromocriptine, carboplatinum, cisplatin, methotrexate, nitrogen mustard, vinblastin, vincristine, acetazolamide, bendroflumethiazide, bumetadine, chlorthalidone, diapamide, ethacrynic acid, furosemide, hydrochlorthiazide, methylchlorthiazide, prednisolone, adrenocorticotrophic hormone (ACTH), thalidomide, misoprotol, hydrocodone, aspirin, acematacine, benorilate, benoxaprofen, carprofen, diclofenac, diflunisal, etocolac, fenoprofen, feprazon, ibuprofen, indomethacin, isoxicam, ketoprofen, methyl salicylates, naproxen, D-penicilliamin, phenylbutazone, piroxicam, proglumetacin, proquazon, rofecoxib, salicylates, sulindac, tolmetin, zomepirac, amitryptiline, alprazolam, clorazepate, chlordiazepoxide, diazepam, flurazepam, lorazepam, midazolam, oxazepam, prozepam, quazepam, temazepam, triazolam, bupropion, carbamzepine, diclofensine, doxepin, desipirimine, fluoxetin, imipramine, lithium, melitracen, molindon, paroxetin, phenelzin, protriptilin, trazodon, zimeldin, chloroquine phosphate, quinacrine hydrochloride, quinine sulfate, alcohol, arsenum, caffeine, lead, marijuana, nicotine, mercury, auronofin, cyclohexane, dichloromethane, hexane, lindane, methyl-chloride, methyl-n-butyl-ketone, perchlor-ethylene, styrene, tetrachlor-ethane, toluol, trichloroethylene, or a combination thereof.

In any of aspects one through four, the effective amount of the neuroprotective peptide can be formulated in a solution, a gel, a foam or fibrin.

In a fifth aspect, disclosed herein are methods of improving visual acuity comprising administering to a subject in need thereof an effective amount of a neuroprotective peptide comprising a MANF family protein, or fragment thereof.

In a sixth aspect, disclosed herein are methods of treating a retinal disorder comprising administering to a subject in need thereof an effective amount of a neuroprotective peptide comprising a MANF family protein, or fragment thereof.

In the sixth aspect, the retinal disorder can be macular degeneration, diabetic eye disease, age-related macular degeneration, branch retinal vein occlusion, central retinal vein occlusion, central retinal artery occlusion, central serous retinopathy, diabetic retinopathy, Fuchs' dystrophy, giant cell arteritis, glaucoma, hypertensive retinopathy, thyroid eye disease, iridocorneal endothelial syndrome, ischemic optic neuropathy, juvenile macular degeneration, macular edema, macular telangiectasia, Marfan syndrome, optic neuritis, photokeratitis, retinitis pigmentosa, retinopathy of prematurity, Stargardt disease, usher syndrome, Wolfram syndrome, or any combination thereof. For example, the retinal disorder can be retinitis pigmentosa.

In either the fifth or sixth aspect, the MANF family protein can be MANF.

In either the fifth or sixth aspect, where the MANF family protein is MANF, the peptide sequence of the neuroprotective peptide can comprise a sequence that has at least about 80% identity with SEQ ID NO:3. For example, the peptide sequence of the neuroprotective peptide can comprise a sequence that has at least about 90% identity with SEQ ID NO:3. In another example, the peptide sequence of the neuroprotective peptide can comprise a sequence that has at least about 95% identity with SEQ ID NO:3. In another example, the peptide sequence of the neuroprotective peptide can consist of a sequence that has at least about 80% identity with SEQ ID NO:3. In another example, the peptide sequence of the neuroprotective peptide can consist of a sequence that has at least about 90% identity with SEQ ID NO:3. In another example, the peptide sequence of the neuroprotective peptide can consist of a sequence that has at least about 95% identity with SEQ ID NO:3. In another example, the peptide sequence of the neuroprotective peptide can consist of a sequence that has 100% identity with SEQ ID NO:3.

The neuroprotective peptides of the fifth or sixth aspect, where the MANF family protein is MANF, can have a length that is greater than, equal to, or less than the length of SEQ ID NO:3. For example, the neuroprotective peptide can have a length that is at least 80% the length of SEQ ID NO:3. In another example, the neuroprotective peptide can have a length that is 100% the length of SEQ ID NO:3.

In either the fifth or sixth aspect, where the MANF family protein is MANF, the peptide sequence of the neuroprotective peptide can consist of a sequence listed in Table 3. The neuroprotective peptide can be cell permeable.

In either the fifth or sixth aspect, the MANF family protein can be CDNF.

In either the fifth or sixth aspect, where the MANF family protein is CDNF, the peptide sequence of the neuroprotective peptide can comprise a sequence that has at least about 80% identity with SEQ ID NO:6. For example, the peptide sequence of the neuroprotective peptide can comprise a sequence that has at least about 90% identity with SEQ ID NO:6. In another example, the peptide sequence of the neuroprotective peptide can comprise a sequence that has at least about 95% identity with SEQ ID NO:6. In another example, the peptide sequence of the neuroprotective peptide can consist of a sequence that has at least about 80% identity with SEQ ID NO:6. In another example, the peptide sequence of the neuroprotective peptide can consist of a sequence that has at least about 90% identity with SEQ ID NO:6. In another example, the peptide sequence of the neuroprotective peptide can consist of a sequence that has at least about 95% identity with SEQ ID NO:6. In another example, the peptide sequence of the neuroprotective peptide can consist of a sequence that is SEQ ID NO:6.

The neuroprotective peptides of the fifth or sixth aspect, where the MANF family protein is CDNF, can have a length that is greater than, equal to, or less than the length of SEQ ID NO:6. For example, the neuroprotective peptide can have a length that is at least 80% the length of SEQ ID NO:6. In another example, the neuroprotective peptide can have a length that is 100% the length of SEQ ID NO:6.

In either the fifth or sixth aspect, where the MANF family protein is CDNF, the peptide sequence of the neuroprotective peptide can consist of a sequence listed in Table 4. The neuroprotective peptide can be cell permeable.

In either the fifth or sixth aspect, the administering is topical, intravitreal, intracameral, systemic, conjunctival, intracorneal, intraocular, ophthalmic, retrobulbar, subconjunctival, or a combination thereof.

In a seventh aspect, disclosed herein are methods of treating or preventing cell death-related sensory loss comprising administering to a subject in need thereof an effective amount of a neuroprotective peptide comprising a MANF family protein, or fragment thereof.

In the seventh aspect, the effective amount of the neuroprotective peptide can be in a formulation at a concentration of about 1 µMol-50 µMol. For example, the effective amount of the neuroprotective peptide can in a formulation at a concentration of about 3 µMol-20 µMol. The effective amount can be administered in a volume of about 100 µL-500 µL of the formulation. For example, the effective amount can be administered in a volume of about 200 µL-300 µL of the formulation.

In the seventh aspect, the effective amount of the neuroprotective peptide can be about 1 µg-500 µg. For example, the effective amount of the neuroprotective peptide can be about 5 µg-250 µg.

In an eighth aspect, disclosed herein are methods of treating or preventing cell death-related sensory loss comprising administering to a subject in need thereof an effective amount of a viral expression vector comprising a promoter sequence capable of directing the expression of an operably linked transgene encoding a neuroprotective peptide comprising a MANF family protein, or fragment thereof.

In either the seventh or eighth aspect, the MANF family protein can be MANF.

In the seventh or eighth aspect, where the MANF family protein is MANF, the peptide sequence of the neuroprotective peptide can comprise a sequence that has at least about 80% identity with SEQ ID NO:3. For example, the peptide sequence of the neuroprotective peptide can comprise a sequence that has at least about 90% identity with SEQ ID NO:3. In another example, the peptide sequence of the neuroprotective peptide can comprise a sequence that has at least about 95% identity with SEQ ID NO:3. In another example, the peptide sequence of the neuroprotective peptide can consist of a sequence that has at least about 80% identity with SEQ ID NO:3. In another example, the peptide sequence of the neuroprotective peptide can consist of a sequence that has at least about 90% identity with SEQ ID NO:3. In another example, the peptide sequence of the neuroprotective peptide can consist of a sequence that has at least about 95% identity with SEQ ID NO:3. In another example, the peptide sequence of the neuroprotective peptide can consist of a sequence that has 100% identity with SEQ ID NO:3.

In the seventh or eighth aspect, where the MANF family protein is MANF, the neuroprotective peptide can have a length that is greater than, equal to, or less than the length of SEQ ID NO:3. For example, the neuroprotective peptide can have a length that is at least 80% the length of SEQ ID NO:3. In another example, the neuroprotective peptide can have a length that is 100% the length of SEQ ID NO:3.

In the seventh or eighth aspect, where the MANF family protein is MANF, the peptide sequence of the neuroprotective peptide can consist of a sequence listed in Table 3. The neuroprotective peptide can be cell permeable.

In the eighth aspect, where the MANF family protein is MANF, the transgene can comprise a nucleotide sequence that has at least about 80% identity with SEQ ID NO:184. For example, the transgene can comprise a nucleotide sequence that has at least about 90% identity with SEQ ID NO:184. In another example, the transgene can comprise a nucleotide sequence that has at least about 95% identity with SEQ ID NO:184.

In the eighth aspect, where the MANF family protein is MANF, the transgene can comprise a nucleotide sequence that has at least about 80% identity with SEQ ID NO:185. For example, the transgene can comprise a nucleotide sequence that has at least about 90% identity with SEQ ID NO:185. In another example, the transgene can comprise a nucleotide sequence that has at least about 95% identity with SEQ ID NO:185.

In either the seventh or eighth aspect, the MANF family protein can be CDNF.

In the seventh or eighth aspect, where the MANF family protein is CDNF, the peptide sequence of the neuroprotective peptide can comprise a sequence that has at least about 80% identity with SEQ ID NO:6. For example, the peptide sequence of the neuroprotective peptide can comprise a sequence that has at least about 90% identity with SEQ ID NO:6. In another example, the peptide sequence of the neuroprotective peptide can comprise a sequence that has at least about 95% identity with SEQ ID NO:6. In another example, the peptide sequence of the neuroprotective peptide can consist of a sequence that has at least about 80% identity with SEQ ID NO:6. In another example, the peptide sequence of the neuroprotective peptide can consist of a sequence that has at least about 90% identity with SEQ ID NO:6. In another example, the peptide sequence of the neuroprotective peptide can consist of a sequence that has at least about 95% identity with SEQ ID NO:6. In another example, the peptide sequence of the neuroprotective peptide can consist of a sequence that is SEQ ID NO:6.

In the seventh or eighth aspect, where the MANF family protein is CDNF, the neuroprotective peptide can have a length that is greater than, equal to, or less than the length of SEQ ID NO:6. For example, the neuroprotective peptide can have a length that is at least 80% the length of SEQ ID NO:6. In another example, the neuroprotective peptide can have a length that is 100% the length of SEQ ID NO:6.

In the seventh or eighth aspect, where the MANF family protein is CDNF, the peptide sequence of the neuroprotective peptide can consist of a sequence listed in Table 4. The neuroprotective peptide can be cell permeable.

In the eighth aspect, where the MANF family protein is CDNF, the transgene can comprise a nucleotide sequence that has at least about 80% identity with SEQ ID NO:186. For example, the transgene can comprise a nucleotide sequence that has at least about 90% identity with SEQ ID NO:186. In another example, the transgene can comprise a nucleotide sequence that has at least about 95% identity with SEQ ID NO:186.

In the eighth aspect, where the MANF family protein is CDNF, the transgene can comprise a nucleotide sequence that has at least about 80% identity with SEQ ID NO:187. For example, the transgene can comprise a nucleotide sequence that has at least about 90% identity with SEQ ID NO:187. In another example, the transgene can comprise a nucleotide sequence that has at least about 95% identity with SEQ ID NO:187.

In the eighth aspect, the viral expression vector can be HIV, SIV, FIV, EIAV, AAV, adenovirus, retrovirus, herpes virus, lentivirus, or a replication defective version thereof.

In a ninth aspect, disclosed herein are methods of treating or preventing cell death-related sensory loss in a subject in need thereof, the method comprising administering an effective amount of a MANF modulator. The MANF modulator can be valproic acid.

In any of the seventh, eighth, or ninth aspects, the cell death-related sensory loss can be impaired vision, night blindness, retinal detachment, light sensitivity, tunnel vision, loss of peripheral vision, blindness, spots, or a combination thereof. The cell death-related sensory loss can be caused by macular degeneration, diabetic eye disease, age-related macular degeneration, branch retinal vein occlusion, central retinal vein occlusion, central retinal artery occlusion, central serous retinopathy, diabetic retinopathy, Fuchs' dystrophy, giant cell arteritis, glaucoma, hypertensive retinopathy, thyroid eye disease, iridocorneal endothelial syndrome, ischemic optic neuropathy, juvenile macular degeneration, macular edema, macular telangioctasia, Marfan syndrome, optic neuritis, photokeratitis, retinitis pigmentosa, retinopathy of prematurity, Stargardt disease, usher syndrome, Wolfram syndrome, or any combination thereof. The administering can be topical, intravitreal, intracameral, systemic, conjunctival, intracorneal, intraocular, ophthalmic, retrobulbar, subconjunctival, or a combination thereof.

In any of the seventh, eighth, or ninth aspects, the cell death-related sensory loss can be a loss or decrease of the ability to smell. The cell death-related sensory loss can be caused by age, trauma, disease, or a combination thereof. Administering can comprise endosunusial administration, intrasinal administration, intranasal administration, nasal administration, transmucosal administration, or a combination thereof.

In any of the seventh, eighth, or ninth aspects, the cell death-related sensory loss can be a loss or decrease of the ability to taste. The cell death-related sensory loss can be caused by zinc deficiency or zinc toxicity, age, drug or toxin exposure, or a combination thereof. Administering can comprise buccal administration, sublingual administration, oral administration, endosunusial administration, intrasinal administration, intranasal administration, nasal administration, transmucosal administration, or a combination thereof.

In any of the seventh, eighth, or ninth aspects, the cell death-related sensory loss can be reduced sensitivity to temperature change and pain, spontaneous tingling or burning pain, skin allodynia (severe pain from normally non-painful stimuli, such as light touch), or a combination thereof. The cell death-related sensory loss can be caused by chemotherapy-linked neuropathy or diabetic neuropathy. Administering can comprise cutaneous injection, intraepidermal administration, intravenous administration, oral administration, perineural, subcutaneous administration, topical administration, transdermal administration, or a combination thereof.

In any of the seventh, eighth, or ninth aspects, the cell death-related sensory loss can be hearing loss, tinnitus, vertigo, instability or loss of balance, nausea, or a combination thereof. The cell death-related sensory loss can be age-related hearing loss. The cell death-related sensory loss can be noise-induced hearing loss. The cell death-related sensory loss can be caused by an ototoxic chemical. The cell death-related sensory loss can be caused by drug-induced ototoxicity. Administering can comprise topical administration, systemic administration, intratympanic administration, intracochlear administration, transtympanic injection, or a combination thereof.

In a tenth aspect, disclosed herein are methods of treating or preventing ototoxicity comprising administering to a subject in need thereof an effective amount of a viral expression vector comprising a promoter sequence capable of directing the expression of an operably linked transgene encoding a neuroprotective peptide comprising a MANF family protein, or fragment thereof.

In the tenth aspect, the MANF family protein can be MANF.

In the tenth aspect, where the MANF protein is MANF, the peptide sequence of the neuroprotective peptide can comprise a sequence that has at least about 80% identity with SEQ ID NO:3. For example, the peptide sequence of the neuroprotective peptide can comprise a sequence that has at least about 90% identity with SEQ ID NO:3. In another example, the peptide sequence of the neuroprotective peptide can comprise a sequence that has at least about 95% identity with SEQ ID NO:3. In another example, the peptide sequence of the neuroprotective peptide can consist of a sequence that has at least about 80% identity with SEQ ID NO:3. In another example, the peptide sequence of the neuroprotective peptide can consist of a sequence that has at least about 90% identity with SEQ ID NO:3. In another example, the peptide sequence of the neuroprotective peptide can consist of a sequence that has at least about 95% identity with SEQ ID NO:3. In another example, the peptide sequence of the neuroprotective peptide can consist of a sequence that has 100% identity with SEQ ID NO:3.

In the tenth aspect, where the MANF family protein is MANF, the neuroprotective peptide can have a length that is greater than, equal to, or less than the length of SEQ ID NO:3. For example, the neuroprotective peptide can have a length that is at least 80% the length of SEQ ID NO:3. In another example, the neuroprotective peptide can have a length that is 100% the length of SEQ ID NO:3.

In the tenth aspect, where the MANF family protein is MANF, the peptide sequence of the neuroprotective peptide can consist of a sequence listed in Table 3. The neuroprotective peptide can be cell permeable.

In the tenth aspect, where the MANF family protein is MANF, the transgene can comprise a nucleotide sequence that has at least about 80% identity with SEQ ID NO:184. For example, the transgene can comprise a nucleotide sequence that has at least about 90% identity with SEQ ID NO:184. In another example, the transgene can comprise a nucleotide sequence that has at least about 95% identity with SEQ ID NO:184.

In the tenth aspect, where the MANF family protein is MANF, the transgene can comprise a nucleotide sequence that has at least about 80% identity with SEQ ID NO:185.

For example, the transgene can comprise a nucleotide sequence that has at least about 90% identity with SEQ ID NO:185. In another example, the transgene can comprise a nucleotide sequence that has at least about 95% identity with SEQ ID NO:185.

In the tenth aspect, the MANF family protein can be CDNF.

In the tenth aspect, where the MANF family protein is CDNF, the peptide sequence of the neuroprotective peptide can comprise a sequence that has at least about 80% identity with SEQ ID NO:6. For example, the peptide sequence of the neuroprotective peptide can comprise a sequence that has at least about 90% identity with SEQ ID NO:6. In another example, the peptide sequence of the neuroprotective peptide can comprise a sequence that has at least about 95% identity with SEQ ID NO:6. In another example, the peptide sequence of the neuroprotective peptide can consist of a sequence that has at least about 80% identity with SEQ ID NO:6. In another example, the peptide sequence of the neuroprotective peptide can consist of a sequence that has at least about 90% identity with SEQ ID NO:6. In another example, the peptide sequence of the neuroprotective peptide can consist of a sequence that has at least about 95% identity with SEQ ID NO:6. In another example, the peptide sequence of the neuroprotective peptide can consist of a sequence that is SEQ ID NO:6.

In the tenth aspect, where the MANF family protein is CDNF, the neuroprotective peptide can have a length that is greater than, equal to, or less than the length of SEQ ID NO:6. For example, the neuroprotective peptide can have a length that is at least 80% the length of SEQ ID NO:6. In another example, the neuroprotective peptide can have a length that is 100% the length of SEQ ID NO:6.

In the tenth aspect, where the MANF family protein is CDNF, the peptide sequence of the neuroprotective peptide can consist of a sequence listed in Table 4. The neuroprotective peptide can be cell permeable.

In the tenth aspect, where the MANF family protein is CDNF, the transgene can comprise a nucleotide sequence that has at least about 80% identity with SEQ ID NO:186. For example, the transgene can comprise a nucleotide sequence that has at least about 90% identity with SEQ ID NO:186. In another example, the transgene can comprise a nucleotide sequence that has at least about 95% identity with SEQ ID NO:186.

In the tenth aspect, where the MANF family protein is CDNF, the transgene can comprise a nucleotide sequence that has at least about 80% identity with SEQ ID NO:187. For example, the transgene can comprise a nucleotide sequence that has at least about 90% identity with SEQ ID NO:187. In another example, the transgene can comprise a nucleotide sequence that has at least about 95% identity with SEQ ID NO:187.

In the tenth aspect, the viral expression vector can be HIV, SIV, FIV, EIAV, AAV, adenovirus, retrovirus, herpes virus, lentivirus, or a replication defective version thereof.

In an eleventh aspect, disclosed herein are methods of treating or preventing ototoxicity comprising administering to a subject in need thereof an effective amount of a MANF modulator. The MANF modulator can be valproic acid.

In the tenth or eleventh aspect, administering can occur prior to a therapeutic treatment with a drug.

In the tenth or eleventh aspect, administering can comprise topical administration, systemic administration, intratympanic administration, intracochlear administration, transtympanic injection, or a combination thereof. For example, administering can comprise intratympanic administration by injection or perfusion. In another example, administering can comprise intrachochlear administration that is: by injection, with a cochlear implant, with an osmotic mini-pump, or with a reciprocating perfusion system.

In the tenth or eleventh aspect, administering can occur prior to a therapeutic treatment with a drug.

In the tenth or eleventh aspect, administering can occur after beginning a therapeutic treatment with a drug.

In the tenth or eleventh aspect, administering can occur after the subject in need thereof has experienced symptoms of drug-induced ototoxicity.

In the tenth or eleventh aspect, administering can occur before an anticipated exposure, during an exposure, or after an exposure to an ototoxic chemical or toxin.

In the tenth or eleventh aspect, the subject in need thereof can have symptoms of ototoxicity comprising hearing loss, tinnitus, vertigo, instability or loss of balance, nausea, or a combination thereof.

In the tenth or eleventh aspect, the ototoxicity can be caused by an anesthetic, an antibiotic, an antimalarial, a cardiac medication, a chemotherapeutic agent, a diuretic, a glucocorticosteroid, an immunomodulatory drug, a mucosal protectant, a narcotic analgesic, a non-steroidal anti-inflammatory drug (NSAID), a psychopharmacologic agent, a quinine, a toxic substance, a vapor or solvent, or a combination thereof.

In the tenth or eleventh aspect, the ototoxicity can be caused by amikacin, amphotericin B, capreomycin, chloramphenicol, erythromycin, gentamycin, kanamycin, minocycline, polymyxin B, neomycin, netilimicin, streptomycin, a sulfonamide, tobramycin, vancomycin, chloroquine, hydroxychloroquine, celiprolol, flecainide, lidocaine, metoprolol, procainamide, propranolo, quinidine, bleomycine, bromocriptine, carboplatinum, cisplatin, methotrexate, nitrogen mustard, vinblastin, vincristine, acetazolamide, bendroflumethiazide, bumetadine, chlorthalidone, diapamide, ethacrynic acid, furosemide, hydrochlorthiazide, methylchlorthiazide, prednisolone, adrenocorticotrophic hormone (ACTH), thalidomide, misoprotol, hydrocodone, aspirin, acematacine, benorilate, benoxaprofen, carprofen, diclofenac, diflunisal, etocolac, fenoprofen, feprazon, ibuprofen, indomethacin, isoxicam, ketoprofen, methyl salicylates, naproxen, D-Penicilliamin, phenylbutazone, piroxicam, proglumetacin, proquazon, rofecoxib, salicylates, sulindac, tolmetin, zomepirac, amitryptiline, alprazolam, clorazepate, chlordiazepoxide, diazepam, flurazepam, lorazepam, midazolam, oxazepam, prozepam, quazepam, temazepam, triazolam, bupropion, carbamzepine, diclofensine, doxepin, desiprimine, fluoxetin, imipramine, lithium, melitracen, molindon, paroxetin, phenelzin, protriptilin, trazodon, zimeldin, chloroquine phosphate, quinacrine hydrochloride, quinine sulfate, alcohol, arsenum, caffeine, lead, marijuana, nicotine, mercury, auronofin, cyclohexane, dichloromethane, hexane, lindane, methyl-chloride, methyl-n-butyl-ketone, perchlor-ethylene, styrene, tetrachlor-ethane, toluol, trichloroethylene, or a combination thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference. In the event

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
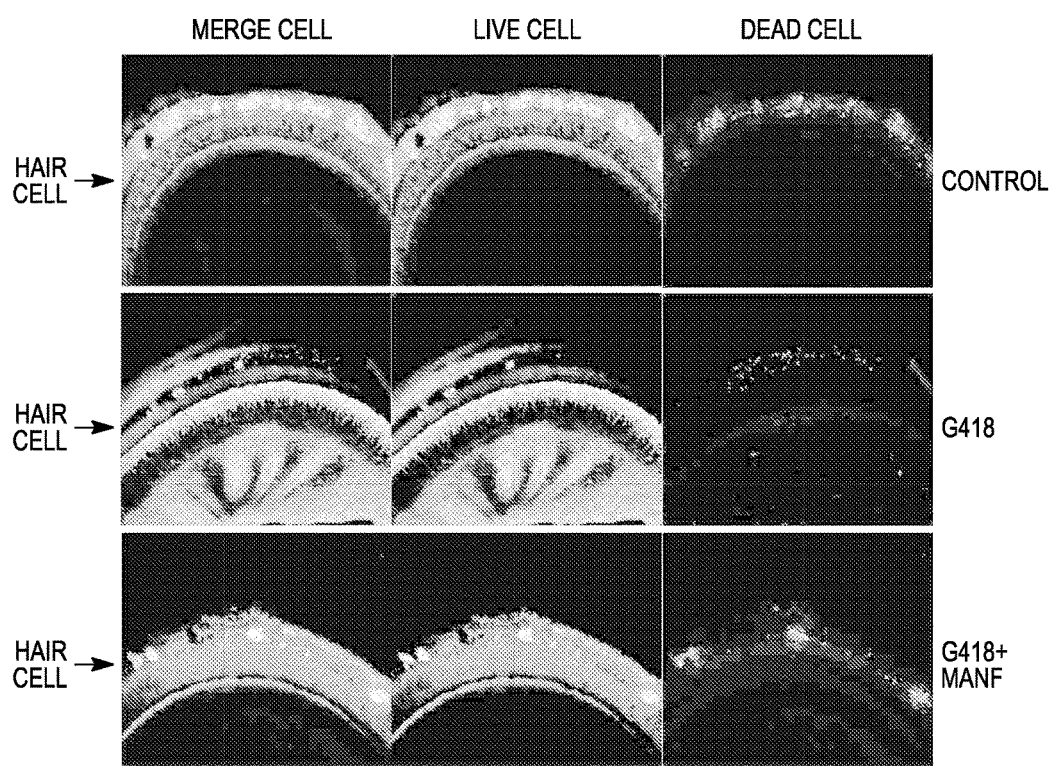
FIG. 1 illustrates the results of an in vitro assay for hair cell survival; the top row shows a control cochlea organ culture, the middle row shows a Geneticin (G418) (aminoglycoside antibiotic)-treated cochlea organ culture, the bottom row shows a MANF and G418 cochlea organ culture; the right column shows dead cells, the middle column shows living cells, and the left column is a merge of the other two images.

Mis-regulation of cell death is a common feature of many diseases involving sensory loss or distortion. For example, mis-regulation of cell death can result in loss of sight, hearing, smell, taste, or touch. Mis-regulated cell death resulting in loss of hearing can be caused by a combination of factors, including hereditable factors and environmental factors. For example, exposure to excessive noise, exposure to radiation, or exposure to ototoxic substances can cause hearing loss. Disclosed herein are compositions and methods for treating or preventing sensory loss caused by mis-regulation of cell death, including compositions and methods for treating or preventing ototoxicity.

For the purposes of clarity and a concise description, features can be described herein as part of the same or separate embodiments; however it will be appreciated that the scope of the invention may include embodiments having combinations of all or some of the features described.

The terminology used herein is for the purpose of describing particular embodiments only and is not intended to be limiting of the invention.

As used herein, the indefinite articles "a", "an" and "the" should be understood to include plural reference unless the context clearly indicates otherwise.

The phrase "and/or," as used herein, should be understood to mean "either or both" of the elements so conjoined, e.g., elements that are conjunctively present in some cases and disjunctively present in other cases.

As used herein, "or" should be understood to have the same meaning as "and/or" as defined above. For example, when separating a listing of items, "and/or" or "or" shall be interpreted as being inclusive, e.g., the inclusion of at least one, but also including more than one, of a number of items, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

As used herein, the terms "including", "includes", "having", "has", "with", or variants thereof, are intended to be inclusive similar to the term "comprising."

As used herein, the term "about" means plus or minus 10% of the indicated value. For example, about 100 means from 90 to 110.

All genes and gene products (including RNA and proteins), and their respective names, disclosed herein are intended to correspond to homologs from any species for which the compositions and methods disclosed herein are applicable. When a gene or gene product from a particular species is disclosed, it is understood that this disclosure is intended to be exemplary only and is not to be interpreted as a limitation unless the context in which it appears clearly indicates otherwise. For example, the genes and gene products disclosed herein, which in some embodiments relate to mammalian (including human) nucleic acid and/or amino acid sequences, are intended to encompass homologous and/or orthologous and/or paralogous genes and gene products from other animals including, but not limited to, other mammals, fish, reptiles, amphibians, birds, and other vertebrates.

In the context of the present invention, the terms "polypeptide," "peptide," and "protein" are equivalent and mutually interchangeable. They refer to any amino acid chain, including native peptides, degradation products, synthetically synthesized peptides, or recombinant peptides; and include any post-translational modifications thereto (for example phosphorylation or glycosylation). Polypeptides include modified peptides, which may have, for example, modifications rendering the peptides more stable or less immunogenic. Such modifications can include, but are not limited to, cyclization, N-terminus modification, C-terminus modification, peptide bond modification, backbone modification and residue modification. Acetylation-amidation of the termini of the peptide (e.g., N-terminal acetylation and C-terminal amidation) can increase the stability and cell permeability of the peptides.

As used herein, the term "fragment" refers to a portion of a compound. For example, when referring to a protein, a fragment is a plurality of consecutive amino acids comprising less than the entire length of the polypeptide.

The disclosure of a particular sequence should be understood as disclosure of all fragments of a sequence. A fragment of a sequence can be defined according to a percent length of a reference sequence (e.g., a reference protein or peptide sequence). For example, a fragment of a sequence (e.g., protein or peptide sequence) can have a length that is at least about 1%, 2%, 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99% of the length of the reference sequence. In another example, a fragment of a sequence (e.g., protein or peptide sequence) can have a length that is at most about 1%, 2%, 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99% of the length of the reference sequence. In another example, a fragment of a sequence (e.g., protein or peptide sequence) can have a length that is about 1-99%, 2-99%, 5-99%, 10-99%, 20-99%, 30-99%, 40-99%, 50-99%, 60-99%, 70-99%, 80-99%, 90-99%, 2-90%, 5-90%, 10-90%, 20-90%, 30-90%, 40-90%, 50-90%, 60-90%, 70-90%, 80-90%, 5-80%, 10-80%, 20-80%, 30-80%, 40-80%, 50-80%, 60-80%, 70-80%, 10-70%, 20-70%, 30-70%, 40-70%, 50-70%, 60-70%, 20-60%, 30-60%, 40-60%, 50-60%, 30-50%, 40-50%, or 30-40% of the length of the reference sequence. Fragments can also be defined as have a percent identity to a reference sequence; for example a fragment can have length that is less than the reference sequence and a percent identity of the reference sequence.

The term "identity" refers to a relationship between the sequences of two or more polypeptide molecules or two or more nucleic acid molecules, as determined by aligning and comparing the sequences. "Percent identity" means the percent of identical residues between the amino acids or nucleotides in the compared molecules and is calculated based on the size of the smallest of the molecules being compared. For these calculations, gaps in alignments (if any) are preferably addressed by a particular mathematical model or computer program (i.e., an "algorithm"). Methods that can be used to calculate the identity of the aligned nucleic acids or polypeptides include those described in Computational Molecular Biology, (Lesk, A. M., ed.), 1988, New York: Oxford University Press; Biocomputing Informatics and Genome Projects, (Smith, D. W., ed.), 1993, New York: Academic Press; Computer Analysis of Sequence Data, Part I, (Griffin, A. M., and Griffin, H. G., eds.), 1994, New Jersey: Humana Press; von Heinje, G., 1987, Sequence Analysis in Molecular Biology, New York: Academic Press; Sequence Analysis Primer, (Gribskov, M. and Devereux, J., eds.), 1991, New York: M. Stockton Press; and Carillo et al, 1988, SUM J. Applied Math. 48: 1073.

The disclosure of any particular sequence herein should be interpreted as the disclosure of all sequences sharing a percent identity with the sequence. A sequence can be defined herein according to a percent identity with a reference sequence. For example, the sequence can have at least about: 50%, 55%, 60%, 65%, 70%, 75%, 80%, 85%, 90%, 95%, 96%, 97%, 98%, 99%, or 100% identity with the reference sequence. In another example, the sequence can have about: 50-60%, 50-75%, 50-80%, 50-85%, 50-90%, 50-95%, 50-97%, 50-99%, 50-100%, 60-75%, 60-80%, 60-85%, 60-90%, 60-95%, 60-97%, 60-99%, 60-100%, 75-80%, 75-85%, 75-90%, 75-95%, 75-97%, 75-99%, 75-100%, 80-85%, 80-90%, 80-95%, 80-97%, 80-99%, 80-100%, 85-90%, 85-95%, 85-97%, 85-99%, 85-100%, 90-95%, 90-97%, 90-99%, 90-100%, 95-97%, 95-99%, 95-100%, 97-99%, 97-100%, or 99-100% identity with the reference sequence. Such sequences can be called variants of the reference sequence.

A "variant" of a polypeptide comprises an amino acid sequence wherein one or more amino acid residues are inserted into, deleted from and/or substituted into the amino acid sequence relative to another polypeptide sequence. The substituted amino acid(s) can be conservative substitutions or non-conservative substitutions, depending upon the context. Variants include fusion proteins.

Conservative substitutions are substitutions of one amino acid with a chemically similar amino acid. The following six groups each contain amino acids that are conservative substitutions for one another: (1) Alanine (A), Serine (S), Threonine (T); (2) Aspartic acid (D), Glutamic acid (E); (3) Asparagine (N), Glutamine (Q); (4) Arginine (R), Lysine (K); (5) Isoleucine (I), Leucine (L), Methionine (M), Valine (V); and (6) Phenylalanine (F), Tyrosine (Y), Tryptophan (W).

In making changes to the peptides and proteins disclosed herein, the hydropathic index of amino acids can be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein or peptide is understood in the art. Kyte et al., J. Mol. Biol, 157: 105-131 (1982). It is known that certain amino acids can be substituted for other amino acids having a similar hydropathic index or score and still retain a similar biological activity. In making changes based upon the hydropathic index, the substitution of amino acids whose hydropathic indices are within ±2, ±1, or ±0.5 are included.

It is also understood in the art that the substitution of like amino acids can be made effectively on the basis of hydrophilicity. In certain embodiments, the greatest local average hydrophilicity of a protein or peptide, as governed by the hydrophilicity of its adjacent amino acids, correlates with a biological property of the protein or peptide.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, the substitution of amino acids whose hydrophilicity values are within ±2, ±1, ±0.5 are included.

As used herein, the term "subject" refers to any animal (e.g., mammals, birds, reptiles, amphibians, fish), including, but not limited to, humans, non-human primates, rodents, and the like, which is to be the recipient of a particular treatment. Typically, the terms "subject" and "patient" may be used interchangeably herein in reference to a subject.

As used herein, the term "administering" refers to providing a therapeutically effective amount of a chemical or biological compound or pharmaceutical composition to a subject. The chemical or biological compound of the present invention can be administered alone, but may be administered with other compounds, excipients, fillers, binders, carriers or other vehicles selected based upon the chosen route of administration and standard pharmaceutical practice. Administration may be by way of carriers or vehicles, such as injectable solutions, including sterile aqueous or non-aqueous solutions, or saline solutions; creams; lotions; capsules; tablets; granules; pellets; powders; suspensions, emulsions, or microemulsions; patches; micelles; liposomes; vesicles; implants, including microimplants; eye drops; ear drops; sprays, including nasal sprays; other proteins and peptides; synthetic polymers; microspheres; nanoparticles; and the like.

The chemical or biological compound or pharmaceutical composition of the present invention may also be included, or packaged, with other non-toxic compounds, such as pharmaceutically acceptable carriers, excipients, binders and fillers including, but not limited to, glucose, lactose, gum acacia, gelatin, mannitol, xanthan gum, locust bean gum, galactose, oligosaccharides and/or polysaccharides, starch paste, magnesium trisilicate, talc, corn starch, starch fragments, keratin, colloidal silica, potato starch, urea, dextrans, dextrins, and the like. Moreover, the packaging material may be biologically inert or lack bioactivity, such as plastic polymers, silicone, etc. and may be processed internally by the subject without affecting the effectiveness of the neurotrophic factor packaged and/or delivered therewith.

The term "effective amount," as applied to the compound(s), biologics and pharmaceutical compositions described herein, means the quantity necessary to render the desired therapeutic result. For example, an effective amount is a level effective to treat, cure, or alleviate the symptoms of a disorder for which the therapeutic compound, biologic or composition is being administered. Amounts effective for the particular therapeutic goal sought will depend upon a variety of factors including the disorder being treated and its severity and/or stage of development/progression; the bioavailability, and activity of the specific compound, biologic or pharmaceutical composition used; the route or method of administration and introduction site on the subject; the rate of clearance of the specific compound or biologic and other pharmacokinetic properties; the duration of treatment; inoculation regimen; drugs used in combination or coincident with the specific compound, biologic or composition; the age, body weight, sex, diet, physiology and general health of the subject being treated; and like factors well known to one of skill in the relevant scientific art. Some variation in dosage can occur depending upon the condition of the subject being treated, and the physician or other individual administering treatment will, in any event, determine the appropriate dose for an individual patient.

As used herein, "disorder" refers to a disorder, disease or condition, or other departure from healthy or normal biological activity, and the terms can be used interchangeably. The terms would refer to any condition that impairs normal function. The condition may be caused by sporadic or heritable genetic abnormalities. The condition may also be caused by non-genetic abnormalities. The condition may also be caused by injuries to a subject from environmental factors, such as, but not limited to, cutting, crushing, burning, piercing, stretching, shearing, injecting, or otherwise modifying a subject's cell(s), tissue(s), organ(s), system(s), or the like.

As used herein, "treatment" or "treating" refers to arresting or inhibiting, or attempting to arrest or inhibit, the development or progression of a disorder and/or causing, or attempting to cause, the reduction, suppression, regression, or remission of a disorder and/or a symptom thereof. As would be understood by those skilled in the art, various clinical and scientific methodologies and assays may be used to assess the development or progression of a disorder, and similarly, various clinical and scientific methodologies and assays may be used to assess the reduction, regression, or remission of a disorder or its symptoms. Additionally, treatment can be applied to a subject or to a cell culture.

Introduction

Cell death (e.g., via apoptosis, autophagy, necrosis) is a common feature of many diseases or disorders affecting sensory perception. Cell death is a common feature of many retinal degenerative diseases. Cell death mis-regulation is also implicated in acquired and genetic hearing impairment; for example, due to damage to the cochlear and vestibular systems of the ear. Acquired hearing impairment can be caused by ototoxicity. Mis-regulated cell death, particularly of olfactory sensory neurons, is also associated with the loss of the sense of smell. Mis-regulation of cell death, particularly of mature taste bud cells and taste progenitor cells, can also directly lead to the loss or decrease of the ability to taste. There is a need in the art to develop therapies to combat sensory loss, including sensory loss caused by mis-regulation of cell death. There is also a need in the art to develop therapies treat or prevent ototoxity.

Cell death can be classified according to its morphological appearance (which may be apoptotic, necrotic, autophagic, necroptic, or associated with mitosis), enzymological criteria (with and without the involvement of nucleases or of distinct classes of proteases, such as caspases, calpains, cathepsins and transglutaminases), functional aspects (programmed or accidental, physiological or pathological) or immunological characteristics (immunogenic or non-immunogenic). There are at least five distinct modalities of cell death, including cornification, autophagy, necrosis, necroptic, and apoptosis.

Autophagic cell death is a type of cell death involving enhanced autophagic catabolism of the cell. Morphologically, autophagy can be identified by a lack of chromatin condensation, massive vacuolization of the cytoplasm, accumulation of double-membrane autophagic vacuoles in the cytoplasm, and little or no uptake by phagocytic cells (in vivo). Biochemical features of autophagy include Beclin-1 dissociation from Bcl-2/XL, dependency on atg gene products, LC3-I to LC3-II conversion, and p62Lck degradation.

Necrotic cell death is cell death lacking the features of apoptosis or autophagy. Morphologically, necrosis can be identified by cytoplasmic swelling (oncosis), rupture of the plasma membrane, swelling of cytoplasmic organelles, and moderate chromatin condensation. Biochemical features of necrosis include activation of calpains, activation of cathepsins, a drop in ATP levels, HMGB-1 release, lysosomal membrane permeabilization (LMP), plasma membrane rupture, RIP1 phosphorylation, RIP1 ubiquitination, and elevated ROS generation. Cornification is a very specific form of programmed cell death that occurs in the epidermis.

Apoptosis is a term that defines a type of cell death with specific morphological features. It is not necessarily a synonym of programmed cell death or caspace activation. The morphological features associated with apoptosis include a rounding-up of the cell, retraction of pseudopodia, a reduction of cellular and nuclear volume (pyknosis), nuclear fragmentation (karyorrhexis), minor modifications of cytoplasmic organelles, plasma membrane blebbing, and eventual engulfment by resident phagocytes (in vivo). Biochemical features of apoptosis include activation of proapoptotic Bcl-2 family proteins (e.g., Bax, Bak, Bid), activation of caspases, mitochondrial transmembrane permeabilization ($\Delta\Psi m$) dissipation, mitochondrial membrane permeabilization (MMP), oligonucleosomal DNA fragmentation, plasma membrane rupture, phosphatidylserine (PS) exposure, reactive oxygen species (ROS) over generation, and ssDNA accumulation.

Virtually all cells carry the genetic machinery needed to commit suicide. This process typically occurs by a program known as apoptosis. The ability to initiate apoptosis serves a variety of fundamental developmental and homeostatic roles in organisms. A general rule of embryogenesis is that many more cells are produced within each lineage than are needed for organ formation. Local cell-cell interactions determine which ones are valuable members of the community and therefore should be retained, and which ones are surplus cells that should be selectively deleted. In some regions of the developing nervous system, this selection process can result in the death of up to 95% of the neurons before or shortly after birth. Apoptosis can also be employed to remove deleterious cells, such as self-reactive lymphocytes during negative selection in the thymus. Here too, more than 95% of the T cells produced in the bone narrow die in the thymus because they have either failed to develop normally or instead recognize our own proteins as foreign.

While apoptosis provides an essential tool for building and maintaining the human body, its use comes at a very high cost. It has been estimated that mis-regulation of apoptosis accounts for more than 70% of all human disease. Inappropriate activation of apoptosis can result in the loss of valuable but condemned cells, such as neurons in Alzheimer's and Parkinson's Diseases. Conversely, some cells have genetic defects that prevent them from activating apoptosis under the appropriate conditions, which can allow these potentially deleterious cells to persist and induce pathogenesis. This inhibition of cell death is what happens with most cancers and virtually all auto-immune diseases.

While the proteins that comprise the core "killing" machinery of apoptosis have been defined in exquisite detail, much less is known about the signaling pathways that allow this process to be regulated in a cell-type specific manner. By selectively targeting these signaling molecules it will be possible to develop therapies that activate or inhibit apoptosis in a lineage-specific manner. For example, the provision of selective growth factors could allow valuable but condemned cells, such as dopaminergic neurons in Parkinson's disease, to survive the insults that lead to their inappropriate death during disease.

Cell Death and Sensory Loss

Cell death (e.g., via apoptosis, autophagy, necrosis) is a common feature of many diseases or disorders affecting sensory perception.

Cell death is a common feature of many retinal degenerative diseases. This controlled type of cell death happens normally in development and some body functions, but when it happens abnormally in the retina, it can kill the cells required for light detection and vision.

Cell death in retinal cell populations has been detected in a wide range of eye diseases causing visual impairment. Compared to necrosis, apoptosis is an early maker of disease and represents a controlled form of cell death. It is now known that multiple pathways, including oxidative stress and nitric oxide synthase, and both mitochondrial-mediated caspase-dependent and -independent mechanisms are involved, with variations dependent on disease and cell type. Retinal diseases in which cell death mis-regulation plays a part include retinitis pigmentosa, retinal dystrophies, age-related macular degeneration, glaucoma, and diabetic retinopathy. Symptoms of these retinal diseases include impaired vision, night blindness, retinal detachment, light sensitivity, tunnel vision, loss of peripheral vision, or blindness.

Cell death mis-regulation is also implicated in acquired and genetic hearing impairment; for example, due to damage to the cochlear and vestibular systems of the ear. Apoptosis of sensory hair cells in these systems is an important contributor to several acquired hearing pathologies. Cell death of hair cells in the cochleae is associated with hearing loss, tinnitus, and vertigo. Cell death of vestibular hair cells is associated with vertigo and instability or loss of balance. Nausea is also a common symptom of damage to the vestibular system.

The outer hair cells in particular appear to be very susceptible for various cell death stimuli. Exposure to excessive noise can trigger cell death in terminally differentiated sensory hair cells, leading to noise-induced hearing loss. In the case of noise-induced hearing loss, excessive noise exposure triggers the activation of apoptotic cell death programs in these outer hair cells. Cell death is a key event in the pathology of age-related hearing impairment or presbycusis, possibly due to the accumulation of ROS. The use of therapeutic drugs can also result in the activation of cell death in sensory hair cells leading to hearing loss. Such drug-induced ototoxicity has been associated with at least 20 marketed drugs to date, particularly antibiotics and chemotherapies. An example of this effect is the drug cisplatin, which is administered to 25% of cancer patients. Approximately 700,000 cancer patients are treated with cisplatin annually in the US and Western Europe. Ototoxicity can also be associated with toxins, such as heavy metals, and organic solvents (e.g., toluene, styrene, xylene). Symptoms of ototoxicity include hearing loss, vertigo, or tinnitus. Ototoxicity can cause damage to the cochlea, which is a structure of the inner ear that contains several nerve endings and makes hearing possible. Ototoxicity can also induce cell death in the vestibular system, which includes vestibular hair cells. The ototoxicity of chemicals can be enhanced by exposure to excessive noise.

Mis-regulated cell death, particularly of olfactory sensory neurons, is associated with the loss of the sense of smell. Age has a significant impact on the ability to smell with an estimated 25 percent of the elderly population experiencing some degree of olfactory loss. Other major causes of smell loss include trauma and disease (such as sinusitis). All three causes of smell loss are associated with the death of olfactory sensory neurons in the nose. The loss of the sense of smell can also impact the ability to taste.

Mis-regulation of cell death, particularly of mature taste bud cells and taste progenitor cells, can also directly lead to the loss or decrease of the ability to taste. Apoptosis has been implicated in irradiation-triggered taste dysfunction. Zinc deficiency and zinc toxicity can also trigger cell death leading to a decreased ability to taste. Cell death may also be implicated in age-related loss of taste, as well as drug or toxin induced loss of taste.

Peripheral neuropathy is damage or disease affecting nerves. This damage can affect sensation, movement, gland or organ function, and can cause other health problems. Neuropathy may cause painful cramps, fasciculations (fine muscle twitching), muscle loss, bone degeneration, and changes in the skin, hair, and nails. Additionally, motor neuropathy may cause impaired balance and coordination or, most commonly, muscle weakness; sensory neuropathy may cause numbness to touch and vibration, reduced position sense causing poorer coordination and balance, reduced sensitivity to temperature change and pain, spontaneous tingling or burning pain, or skin allodynia (severe pain from normally non-painful stimuli, such as light touch); and autonomic neuropathy may produce diverse symptoms, depending on the affected glands and organs, but common symptoms are poor bladder control, abnormal blood pressure or heart rate, and reduced ability to sweat normally.

Common causes of peripheral neuropathy include systemic diseases (such as diabetes or leprosy), vitamin deficiency, medication (e.g., chemotherapy), traumatic injury, excessive alcohol consumption, immune system disease, infection, or genetic. Neuronal apoptosis has been implicated in chemotherapy-linked neuropathy and diabetic neuropathy.

MANF Family Proteins

Neurotrophic factors are small proteins that are synthesized and released by glial cells that induce neurons to up-regulate survival programs that help protect the cells from apoptosis. One of these neurotrophic factors, mesencephalic astrocyte-derived neurotrophic factor (MANF (NM_006010 (mRNA); NP_006001 (protein))), is an 18 kDa secreted protein. Conserved dopaminergic neurotrophic factor (CDNF (NM_001029954 (mRNA); NP_001025125 (protein))) is the second member of the MANF family of proteins to be discovered.

When tested in a primary nigral neuron cell cultures, MANF protected these midbrain dopaminergic neurons from death. MANF also enhances the survival of dopaminergic neurons in vivo in the rat 6-hydroxydopamine (6-OHDA) model of Parkinson's disease. 6-OHDA is a potent and specific dopaminergic neuron toxin and is used to create an aggressive model of Parkinson's disease. Injection of MANF into 6-OHDA treated rat brains resulted in a statistically significant reduction in the loss of dopaminergic neurons and reduced the behavioral symptoms associated with the disorder. These data are particularly exciting because MANF can improve dopaminergic neuron survival and correct motor defects up to 4 weeks after 6-OHDA treatment, a time when tyrosine hydroxylase (TH) the main biomarker for dopaminergic neurons is no longer normally detectable. Thus, MANF can protect certain neurons from insults that result in cell death.

Certain sensory cells in the eye (retina) and ear (hair cells of the cochlea) express endogenous MANF protein. These cells are of particular interest since there are few treatments for retinopathies or hair cell death. For example, use of certain antibiotics, like neomycin, can result in aminoglycoside-induced deafness (AID) in humans. Experiments with neonatal mouse cochlea reported herein suggest that MANF protects hair cells from Geneticin (G418)-induced cell death. MANF may also induce the proliferation and migration of cochlear Lesser Epithelial Ridge (LER) cells. Without being limited by theory, this can treat or prevent hearing loss because: (1) LER cells can create new hair cells; and (2) LER cells can secrete trophic factors that promote hair cell survival.

Treating or Preventing Sensory Loss

Disclosed herein are methods of treating or preventing cell death-related sensory loss in a subject in need thereof, the methods comprising administering an effective amount of one or more neuroprotective peptides to the subject.

Also disclosed herein are methods of treating or preventing cell death-related sensory loss in a subject in need thereof, the methods comprising administration of an effective amount of a viral expression vector comprising a promoter sequence capable of directing the expression of an operably linked neuroprotective peptide.

Also disclosed herein are methods of treating or preventing cell death-related sensory loss in a subject in need thereof, the methods comprising administration of an effective amount of a MANF modulator. The MANF modulator can be a small molecule or other active agent that increases the expression and/or activity of MANF.

The cell death-related sensory loss can include visual impairment, auditory impairment, olfactory impairment, gustatory impairment, or tactile impairment.

The cell death-related sensory loss can include visual impairment and can include impaired vision, night blindness, retinal detachment, light sensitivity, tunnel vision, loss of peripheral vision, blindness, spots, or a combination thereof. The apoptosis-related sensory loss can be caused, for example, by retinitis pigmentosa, retinal dystrophies, age-related macular degeneration, glaucoma, or diabetic retinopathy.

The cell death-related sensory loss can include a loss or decrease of the ability to smell. The loss or decrease of the ability to smell can be caused by age, trauma, disease, or a combination thereof.

The cell death-related sensory loss can include a loss or decrease of the ability to taste. The loss or decrease of the ability to taste can be caused by zinc deficiency or zinc toxicity. The loss or decrease of the ability to taste can be age related, or due to drug or toxin exposure.

The cell death-related sensory loss can include peripheral neuropathy. Symptoms of peripheral neuropathy can include reduced sensitivity to temperature change and pain, spontaneous tingling or burning pain, skin allodynia (severe pain from normally non-painful stimuli, such as light touch), or a combination thereof. The peripheral neuropathy can be caused by systemic diseases (such as diabetes or leprosy), vitamin deficiency, drug (e.g., chemotherapy) or toxin exposure, traumatic injury, excessive alcohol consumption, immune system disease, infection, or a genetic cause. In some embodiments, the peripheral neuropathy is chemotherapy-linked neuropathy or diabetic neuropathy.

The cell death-related sensory loss can include hearing impairment, hearing loss, tinnitus, vertigo, instability or loss of balance, nausea or a combination thereof. The cell death-related sensory loss can include age-related hearing loss. The cell death-related sensory loss can be caused by noise-induced hearing loss. The cell death-related sensory loss (e.g., hearing loss, tinnitus, vertigo, etc.) can be caused by an ototoxic chemical, radiation, noise, or combination thereof. The cell death-related sensory loss can be caused by drug-induced ototoxicity.

Treating or Preventing Ototoxicity

Ototoxicity is the quality of being toxic to the ear. Ototoxic chemicals can damage the cochlea, auditory nerve, and/or the vestibular system. Such damage can cause, for example, hearing loss or tinnitus. A wide variety of drugs are ototoxic. Factors affecting drug-induced ototoxicity include dose, duration of therapy, concurrent renal failure, infusion rate, lifetime dose, co-administration with other drugs having ototoxic potential, and/or genetic susceptibility. Ototoxicity can also be associated with toxins, such as heavy metals, and organic solvents (e.g., toluene, styrene, xylene). Ototoxicity can also be associated with radiation (e.g., radiation therapy), or mechanical stresses such as noise. Ototoxicity can also be caused by a combination or accumulation of different exposures including ototoxic chemicals, radiation, noise, or other mechanical stresses.

In cases where hearing loss is inevitable due to cumulative ototoxic exposures, patients need to be cognizant of the tradeoffs of potentially curative therapy versus permanent hearing loss. There is a need for treatment regimens that minimize these complications. Accordingly, provided herein are prophylactic methods and/or treatment regimens that prevent or delay onset of ototoxicity and exert an otoprotective effect.

The inner ear comprises two parts: the osseous labyrinth and the membranous labyrinth. The vestibule, the semicircular canals and the cochlea form the osseous labyrinth. The osseous labyrinth is filled with the perilymph which also surrounds the soft tissue of the membranous labyrinth. The membranous labyrinth contains a series of closed sacs containing the endolymph.

The vestibule connects the cochlea in front with the semicircular canals at the back. The cochlea is a conical and spiraled structure located in the rostral part of the labyrinth. The cochlear duct is a single bony tube approximately 34 mm long in humans and spirals around a middle core that contains the spiral ganglion of the auditory nerve. The cochlear duct is divided into three chambers called scalae: the scala vestibule, the scala media and the scala tympani. The oval window touches the scala vestibule and the round window touches the scala tympani. The organ of Corti is the sensory epithelium of the cochlea and comprises rod-shaped cells, supporting cells, and hair cells.

Human ears contain about 17,000 hair cells: a single row of inner hair cells long the length of the cochlea and three rows of outer hair cells extending from the base to the apex of the cochlea. The distribution of receptor cells in the ear is sparse when compared to other sensory organs such as the retina or nasal epithelium; hence the loss of even a few thousand hair cells results in severe hearing loss. Any cochleo-vestibular ototoxicity or acoustic trauma can affect hair cells profoundly; humans cannot regenerate hair cells and once a cochlear hair cell is damaged, the reduction in hearing can be permanent.

Accordingly, disclosed herein are methods of treating or preventing ototoxicity in a subject in need thereof, the method comprising administering an effective amount of one or more neuroprotective peptides to the subject.

Also disclosed herein are methods of treating or preventing ototoxicity in a subject in need thereof, the methods comprising administering an effective amount of a viral expression vector comprising a promoter sequence capable of directing the expression of an operably linked neuroprotective peptide.

Also disclosed herein are methods of treating or preventing ototoxicity in a subject in need thereof, the methods comprising administering an effective amount of a MANF modulator to the subject.

Administering one or more active ingredients (e.g., neuroprotective peptides, viral expression vectors, MANF modulators) can occur prior to a therapeutic treatment with a drug. Administering the one or more neuroprotective peptides can occur concurrently with a therapeutic treatment with a drug. Administering the one or more active ingredients can occur after beginning a therapeutic treatment with a drug. Administering the one or more active ingredients can occur after the subject in need thereof has experienced symptoms of drug-induced ototoxicity during or after a therapeutic treatment with a drug. Administering the one or more active ingredients can occur before an anticipated exposure, during exposure, or after exposure to an ototoxic chemical or toxin.

The symptoms of ototoxicity (e.g., drug-induced ototoxicity) can comprise hearing loss, tinnitus, vertigo, instability or loss of balance, nausea, or a combination thereof.

An ototoxic drug or chemical can be an anesthetic, an antibiotic, an antimalarial, a cardiac medication, a chemotherapeutic agent, a diuretic, a glucocorticosteroid, an immunomodulatory drug, a mucosal protectant, a narcotic analgesic, a non-steroidal anti-inflammatory drug (NSAID), a psychopharmacologic agent, a quinine, a toxic substance, a vapor or solvent, or a combination thereof.

The ototoxic drug or chemical can be an anesthetic. In some embodiments, the anesthetic comprises bupivacain, tetracain, lidocaine, or a combination thereof.

The ototoxic drug or chemical can be an antibiotic. In some embodiments, the antibiotic comprises amikacin, amphotericin B, capreomycin, chloramphenicol, erythromycin, gentamycin, kanamycin, minocycline, polymyxin B, neomycin, netilimicin, streptomycin, a sulfonamide, tobramycin, vancomycin, or a combination thereof.

The ototoxic drug or chemical can be an antimalarial. In some embodiments, the antimalarial comprises chloroquine, hydroxychloroquine, or a combination thereof.

The ototoxic drug or chemical can be a cardiac medication. In some embodiments, the cardiac medication comprises celiprolol, flecainide, lidocaine, metoprolol, procainamide, propranolo, quinidine, or a combination thereof.

The ototoxic drug or chemical can be a chemotherapeutic agent. In some embodiments, the chemotherapeutic agent comprises bleomycine, bromocriptine, carboplatinum, cisplatin, methotrexate, nitrogen mustard, vinblastin, vincristine, or a combination thereof.

The ototoxic drug or chemical can be a diuretic. In some embodiments, the diuretic comprises acetazolamide, bendroflumethiazide, bumetadine, chlorthalidone, diapamide, ethacrynic acid, furosemide, hydrochlorthiazide, methylchlorthiazide, or a combination thereof.

The ototoxic drug or chemical can be a glucocorticosteroid. In some embodiments, the glucocorticosteroid comprises prednisolone, adrenocorticotrophic hormone (ACTH), or a combination thereof.

The ototoxic drug or chemical can be an immunomodulatory drug. In some embodiments, the immunomodulatory drug comprises thalidomide.

The ototoxic drug or chemical can be a mucosal protectant. In some embodiments, the mucosal protectant comprises misoprotol.

The ototoxic drug or chemical can be a narcotic analgesic. In some embodiments, the narcotic analgesic comprises hydrocodone.

The ototoxic drug or chemical can be a NSAID. In some embodiments, the NSAID comprises aspirin, acematacine, benorilate, benoxaprofen, carprofen, diclofenac, diflunisal, etocolac, fenoprofen, feprazon, ibuprofen, indomethacin, isoxicam, ketoprofen, methyl salicylates, naproxen, D-Penicilliamin, phenylbutazone, piroxicam, proglumetacin, proquazon, rofecoxib, salicylates, sulindac, tolmetin, zomepirac, or a combination thereof.

The ototoxic drug or chemical can be a psychopharmacologic agent. In some embodiments, the psychopharmacologic agent comprises amitryptiline, alprazolam, clorazepate, chlordiazepoxide, diazepam, flurazepam, lorazepam, midazolam, oxazepam, prozepam, quazepam, temazepam, triazolam, bupropion, carbamzepine, diclofensine, doxepin, desiprimine, fluoxetin, imipramine, lithium, melitracen, molindon, paroxetin, phenelzin, protriptilin, trazodon, zimeldin, or a combination thereof.

The ototoxic drug or chemical can be a quinine. In some embodiments, the quinine comprises chloroquine phosphate, quinacrine hydrochloride, quinine sulfate, or a combination thereof.

The ototoxic drug or chemical can be a toxic substance. In some embodiments, the toxic substance comprises alcohol, arsenum, caffeine, lead, marijuana, nicotine, mercury, auronofin, or a combination thereof.

The ototoxic drug or chemical can be a vapor or solvent. In some embodiments, the vapor or solvent comprises cyclohexane, dichloromethane, hexane, lindane, methylchloride, methyl-n-butyl-ketone, perchlor-ethylene, styrene, tetrachlor-ethane, toluol, trichloroethylene, or a combination thereof.

Active Ingredients

Active ingredients useful in the methods disclosed herein include neuroprotective peptides, viral expression vectors comprising nucleotides capable of expressing neuroprotective peptides, and/or MANF modulators.

The appropriate dosage of the active ingredient(s) will depend, for example, on the condition to be treated, the severity and course of the condition, whether the active ingredient(s) are administered for preventive or therapeutic purposes, previous therapy, the patient's clinical history and response to the active ingredient(s), the type of active ingredient(s) used, and the discretion of the attending physician. The active ingredient(s) are suitably administered to the patient at one time or over a series of treatments and may be administered to the patient at any time as necessary for treatment or prevention of cell death-related sensory loss. The active ingredient(s) may be administered as the sole treatment or in conjunction with other drugs or therapies useful in treating the condition in question.

Neuroprotective Peptides

Neuroprotective peptides can comprise amino acid sequences corresponding to a full length, or an active fragment of, a protein that is mesencephalic astrocytes-derived neurotrophic factor (MANF), conserved dopamine neurotrophic factor (CDNF), nerve growth factor (NGF), brain-derived neurotrophic factor (BDNF), neurotrophin-3, neurotrophin-4, glial cell line-derived neurotrophic factor (GDNF), neurturin, artemin, persephin, interferon gamma, epidermal growth factor (EGF), basic fibroblast growth factor (bFGF), neurogenin, bone morphogenic protein (BMP), leukemia inhibitory factor (LIF), sonic hedgehog, vascular endothelial growth factor (VEGF), stem cell factor (SCF), or ciliary neurotrophic factor (CNTF). In some embodiments, the neuroprotective peptide is a full length or active fragment of a MANF family protein (e.g., MANF or CDNF). In some embodiments, the MANF family protein is MANF. In some embodiments, the MANF family protein is CDNF.

In some embodiments, a neuroprotective peptide comprises a protein having 70, 80, 85, 90, 95, 96, 97, 98, 99, or 100% homology (or identity) with the sequence of human: MANF, CDNF, NGF, BDNF, neurotrophin-3, neurotrophin-4, GDNF, neurturin, aremin, persephin, interferon gamma, EGF, bFGF, neurogenin, BMP, LIF, sonic hedgehog, VEGF, SCF, or CNTF. In some embodiments, active fragments of these proteins can include peptides with a length of about 4-40 amino acids; for example, about: 4-40, 4-35, 4-30, 4-25, 4-20, 4-15, 4-10, 5-40, 6-40, 7-40, 8-40, 5-35, 5-30, 5-25, 5-20, 5-15, 5-10, 6-35, 6-30, 6-25, 6-20, 6-15, 6-10, 7-35, 7-30, 7-25, 7-20, 7-15, 7-10, 8-35, 8-30, 8-25, 8-20, or 8-15 amino acids. For example, the preferred peptides can consist of 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 amino acids.

Neuroprotective peptides can be a MANF family protein or active fragments thereof. The MANF family protein can be MANF or CDNF. In some embodiments, one or more neuroprotective peptides comprise MANF, or an active fragment thereof. Exemplary MANF peptide sequences can be found in Table 1. In some embodiments, one or more neuroprotective peptides comprise CDNF, or an active fragment thereof. Exemplary CDNF sequences can be found in Table 2. Either MANF or CDNF can be the pro-form, which contains a signal sequence, or the mature, secreted form in which the signal sequence is missing.

In some embodiments, the neuroprotective peptide comprises a protein having 70, 80, 85, 90, 95, 96, 97, 98, 99, or 100% homology (or identity) with the sequence of human CDNF or MANF protein.

In some embodiments, the neuroprotective peptide comprises about: 10%, 20%, 30%, 40%, 50%, 60%, 70%, 80%, 90%, or 100% of the length of human CDNF or MANF protein.

Neuroprotective peptides can be a pro-form of MANF or an active fragment thereof. For example, the peptide sequence of the neuroprotective peptide can comprise or consist of a sequence that has at least about 80% identity with SEQ ID NO: 1. In another example, the peptide sequence of the neuroprotective peptide can comprise or consist of a sequence that has at least about 90% identity with SEQ ID NO: 1. In another example, the peptide sequence of the neuroprotective peptide can comprise or consist of a sequence that has at least about 95% identity with SEQ ID NO: 1. In another example, the peptide sequence of the neuroprotective peptide can comprise or consist of a sequence that has at least about 97% identity with SEQ ID NO: 1. In another example, the peptide sequence of the neuroprotective peptide can comprise or consist of a sequence that has 100% identity with SEQ ID NO: 1. In any of these examples, the neuroprotective peptide can have a length that is at least about 5% the length of SEQ ID NO: 1. In any of these examples, the neuroprotective peptide can have a length that is at least about 50% the length of SEQ ID NO: 1. In any of these examples, the neuroprotective peptide can have a length that is at least about 80% the length of SEQ ID NO: 1. In any of these examples, the neuroprotective peptide can have a length that is at least about 90% the length of SEQ ID NO: 1. In any of these examples, the neuroprotective peptide can have a length that is the same length as SEQ ID NO: 1. The neuroprotective peptide, in any of these examples can also have a maximum length. The maximum length can be, e.g., 100%, 90%, 80%, 70%, 60%, 50%, or 25% the length of SEQ ID NO: 1.

Neuroprotective peptides can be a pro-form of MANF or an active fragment thereof. For example, the peptide sequence of the neuroprotective peptide can comprise or consist of a sequence that has at least about 80% identity with SEQ ID NO: 2. In another example, the peptide sequence of the neuroprotective peptide can comprise or consist of a sequence that has at least about 90% identity with SEQ ID NO: 2. In another example, the peptide sequence of the neuroprotective peptide can comprise or consist of a sequence that has at least about 95% identity with SEQ ID NO: 2. In another example, the peptide sequence of the neuroprotective peptide can comprise or consist of a sequence that has at least about 97% identity with SEQ ID NO: 2. In another example, the peptide sequence of the neuroprotective peptide can comprise or consist of a sequence that has 100% identity with SEQ ID NO: 2. In any of these examples, the neuroprotective peptide can have a length that is at least about 5% the length of SEQ ID NO: 2. In any of these examples, the neuroprotective peptide can have a length that is at least about 50% the length of SEQ ID NO: 2. In any of these examples, the neuroprotective peptide can have a length that is at least about 80% the length of SEQ ID NO: 2. In any of these examples, the neuroprotective peptide can have a length that is at least about 90% the length of SEQ ID NO: 2. In any of these examples, the neuroprotective peptide can have a length that is the same length as SEQ ID NO: 2. The neuroprotective peptide, in any of these examples can also have a maximum length. The maximum length can be, e.g., 100%, 90%, 80%, 70%, 60%, 50%, or 25% the length of SEQ ID NO: 2.

Neuroprotective peptides can be a mature or secreted form of MANF, or an active fragment thereof. For example, the peptide sequence of the neuroprotective peptide can comprise or consist of a sequence that has at least about 80% identity with SEQ ID NO: 3. In another example, the peptide sequence of the neuroprotective peptide can comprise or consist of a sequence that has at least about 90% identity with SEQ ID NO: 3. In another example, the peptide sequence of the neuroprotective peptide can comprise or consist of a sequence that has at least about 95% identity with SEQ ID NO: 3. In another example, the peptide sequence of the neuroprotective peptide can comprise or consist of a sequence that has at least about 97% identity with SEQ ID NO: 3. In another example, the peptide sequence of the neuroprotective peptide can comprise or consist of a sequence that has 100% identity with SEQ ID NO: 3. In any of these examples, the neuroprotective peptide can have a length that is at least about 5% the length of SEQ ID NO: 3. In any of these examples, the neuroprotective peptide can have a length that is at least about 50% the length of SEQ ID NO: 3. In any of these examples, the neuroprotective peptide can have a length that is at least about 80% the length of SEQ ID NO: 3. In any of these examples, the neuroprotective peptide can have a length that is at least about 90% the length of SEQ ID NO: 3. In any of these examples, the neuroprotective peptide can have a length that is the same length as SEQ ID NO: 3. The neuroprotective peptide, in any of these examples can also have a maximum length. The maximum length can be, e.g., 100%, 90%, 80%, 70%, 60%, 50%, or 25% the length of SEQ ID NO: 3.

Neuroprotective peptides can be a synthetic form of MANF, or an active fragment thereof. The synthetic form of MANF contains a non-natural N-terminal methionine. The N-terminal methionine can enable production of the synthetic form of MANF in cell lines lacking the post-translational modification machinery to process the pro-form of MANF to the secreted or mature form of MANF. For example, the peptide sequence of the neuroprotective peptide can comprise or consist of a sequence that has at least about 80% identity with SEQ ID NO: 4. In another example, the peptide sequence of the neuroprotective peptide can comprise or consist of a sequence that has at least about 90% identity with SEQ ID NO: 4. In another example, the peptide sequence of the neuroprotective peptide can comprise or consist of a sequence that has at least about 95% identity with SEQ ID NO: 4. In another example, the peptide sequence of the neuroprotective peptide can comprise or consist of a sequence that has at least about 97% identity with SEQ ID NO: 4. In another example, the peptide sequence of the neuroprotective peptide can comprise or consist of a sequence that has 100% identity with SEQ ID NO: 4. In any of these examples, the neuroprotective peptide can have a length that is at least about 5% the length of SEQ ID NO: 4. In any of these examples, the neuroprotective peptide can have a length that is at least about 50% the length of SEQ ID NO: 4. In any of these examples, the neuroprotective peptide can have a length that is at least about 80% the length of SEQ ID NO: 4. In any of these examples, the neuroprotective peptide can have a length that is at least about 90% the length of SEQ ID NO: 4. In any of these examples, the neuroprotective peptide can have a length that is the same length as SEQ ID NO: 4. The neuroprotective peptide, in any of these examples can also have a maximum length. The maximum length can be, e.g., 100%, 90%, 80%, 70%, 60%, 50%, or 25% the length of SEQ ID NO: 4.

TABLE 1

Human MANF Protein Sequences

| SEQ ID | NAME | ASCESSION Number | SEQUENCE |
|---|---|---|---|
| SEQ ID NO: 1 | Human Pro-MANF | NP_006001 | MRRMRRMWAT QGLAVALALS VLPGSRALRP GDCEVCISYL GRFYQDLKDR DVTFSPATIE NELIKFCREA RGKENRLCYY IGATDDAATK IINEVSKPLA HHIPVEKICE KLKKKDSQIC ELKYDKQIDL STVDLKKLRV KELKKILDDW GETCKGCAEK SDYIRKINEL MPKYAPKAAS ARTDL |
| SEQ ID NO: 2 | Human Pro-MANF | | MWATQGLAVA LALSVLPGSR ALRPGDCEVC ISYLGRFYQD LKDRDVTFSP ATIENELIKF CREARGKENR LCYYIGATDD AATKIINEVS KPLAHHIPVE KICEKLKKKD SQICELKYDK QIDLSTVDLK KLRVKELKKI LDDWGETCKG CAEKSDYIRK INELMPKYAP KAASARTDL |
| SEQ ID NO: 3 | Human MANF (Secreted Form) | | LRPGDCEVCI SYLGRFYQDL KDRDVTFSPA TIENELIKFC REARGKENRL CYYIGATDDA ATKIINEVSK PLAHHIPVEK ICEKLKKKDS QICELKYDKQ IDLSTVDLKK LRVKELKKIL DDWGETCKGC AEKSDYIRKI NELMPKYAPK AASARTDL |
| SEQ ID NO: 4 | Human Synthetic MANF | | MLRPGDCEVC ISYLGRFYQD LKDRDVTFSP ATIENELIKF CREARGKENR LCYYIGATDD AATKIINEVS KPLAHHIPVE KICEKLKKKD SQICELKYDK QIDLSTVDLK KLRVKELKKI LDDWGETCKG CAEKSDYIRK INELMPKYAP KAASARTDL |

Neuroprotective peptides can be a pro-form of CDNF, or an active fragment thereof. For example, the peptide sequence of the neuroprotective peptide can comprise or consist of a sequence that has at least about 80% identity with SEQ ID NO: 5. In another example, the peptide sequence of the neuroprotective peptide can comprise or consist of a sequence that has at least about 90% identity with SEQ ID NO: 5. In another example, the peptide sequence of the neuroprotective peptide can comprise or consist of a sequence that has at least about 95% identity with SEQ ID NO: 5. In another example, the peptide sequence of the neuroprotective peptide can comprise or consist of a sequence that has at least about 97% identity with SEQ ID NO: 5. In another example, the peptide sequence of the neuroprotective peptide can comprise or consist of a sequence that has 100% identity with SEQ ID NO: 5. In any of these examples, the neuroprotective peptide can have a length that is at least about 5% the length of SEQ ID NO: 5. In any of these examples, the neuroprotective peptide can have a length that is at least about 50% the length of SEQ ID NO: 5. In any of these examples, the neuroprotective peptide can have a length that is at least about 80% the length of SEQ ID NO: 5. In any of these examples, the neuroprotective peptide can have a length that is at least about 90% the length of SEQ ID NO: 5. In any of these examples, the neuroprotective peptide can have a length that is the same length as SEQ ID NO: 5. The neuroprotective peptide, in any of these examples can also have a maximum length. The maximum length can be, e.g., 100%, 90%, 80%, 70%, 60%, 50%, or 25% the length of SEQ ID NO: 5.

Neuroprotective peptides can be a mature or secreted form of CDNF, or an active fragment thereof. For example, the peptide sequence of the neuroprotective peptide can comprise or consist of a sequence that has at least about 80% identity with SEQ ID NO: 6. In another example, the peptide sequence of the neuroprotective peptide can comprise or consist of a sequence that has at least about 90% identity with SEQ ID NO: 6. In another example, the peptide sequence of the neuroprotective peptide can comprise or consist of a sequence that has at least about 95% identity with SEQ ID NO: 6. In another example, the peptide sequence of the neuroprotective peptide can comprise or consist of a sequence that has at least about 97% identity with SEQ ID NO: 6. In another example, the peptide sequence of the neuroprotective peptide can comprise or consist of a sequence that has 100% identity with SEQ ID NO: 6. In any of these examples, the neuroprotective peptide can have a length that is at least about 5% the length of SEQ ID NO: 6. In any of these examples, the neuroprotective peptide can have a length that is at least about 50% the length of SEQ ID NO: 6. In any of these examples, the neuroprotective peptide can have a length that is at least about 80% the length of SEQ ID NO: 6. In any of these examples, the neuroprotective peptide can have a length that is at least about 90% the length of SEQ ID NO: 6. In any of these examples, the neuroprotective peptide can have a length that is the same length as SEQ ID NO: 6. The neuroprotective peptide, in any of these examples can also have a maximum length. The maximum length can be, e.g., 100%, 90%, 80%, 70%, 60%, 50%, or 25% the length of SEQ ID NO: 6.

Neuroprotective peptides can be a synthetic form of CDNF, or an active fragment thereof. The synthetic form of CDNF contains a non-natural N-terminal methionine. The N-terminal methionine can enable production of the synthetic form of CDNF in cell lines lacking the post-translational modification machinery to process the pro-form of CDNF to the secreted or mature form of CDNF. For example, the peptide sequence of the neuroprotective peptide can comprise or consist of a sequence that has at least about 80% identity with SEQ ID NO: 7. In another example, the peptide sequence of the neuroprotective peptide can comprise or consist of a sequence that has at least about 90% identity with SEQ ID NO: 7. In another example, the peptide sequence of the neuroprotective peptide can comprise or consist of a sequence that has at least about 95% identity with SEQ ID NO: 7. In another example, the peptide sequence of the neuroprotective peptide can comprise or consist of a sequence that has at least about 97% identity with SEQ ID NO: 7. In another example, the peptide sequence of the neuroprotective peptide can comprise or consist of a sequence that has 100% identity with SEQ ID NO: 7. In any of these examples, the neuroprotective peptide can have a length that is at least about 5% the length of SEQ ID NO: 7. In any of these examples, the neuroprotective peptide can have a length that is at least about 50% the length of SEQ ID NO: 7. In any of these examples, the neuroprotective peptide can have a length that is at least about 80% the length of SEQ ID NO: 7. In any of these examples, the neuroprotective peptide can have a length that is at least about 90% the length of SEQ ID NO: 7. In any of these examples, the neuroprotective peptide can have a length that is the same length as SEQ ID NO: 7. The neuroprotective peptide, in any of these examples can also have a maximum length. The maximum length can be, e.g., 100%, 90%, 80%, 70%, 60%, 50%, or 25% the length of SEQ ID NO: 7.

TABLE 2

Human CDNF Protein Sequences

| SEQ ID | NAME | ASCESSION Number | SEQUENCE |
|---|---|---|---|
| SEQ ID NO: 5 | Human CDNF Pre-cursor | NP_001025125 | MWCASPVAVV AFCAGLLVSH PVLTQGQEAG GRPGADCEVC KEFLNRFYKS LIDRGVNFSL DTIEKELISF CLDTKGKENR LCYYLGATKD AATKILSEVT RPMSVHMPAM KICEKLKKLD SQICELKYEK TLDLASVDLR KMRVAELKQI LHSWGEECRA CAEKTDYVNL IQELAPKYAA THPKTEL |
| SEQ ID NO: 6 | Human CDNF (Mature) | | QEAGGRPGAD CEVCKEFLNR FYKSLIDRGV NFSLDTIEKE LISFCLDTKG KENRLCYYLG ATKDAATKIL SEVTRPMSVH MPAMKICEKL KKLDSQICEL KYEKTLDLAS VDLRKMRVAE LKQILHSWGE ECRACAEKTD YVNLIQELAP KYAATHPKTE L |
| SEQ ID NO: 7 | Human Syn-thetic CDNF | | MQEAGGRPGA DCEVCKEFLN RFYKSLIDRG VNFSLDTIEK ELISFCLDTK GKENRLCYYL GATKDAATKI LSEVTRPMSV HMPAMKICEK LKKLDSQICE LKYEKTLDLA SVDLRKMRVA ELKQILHSWG EECRACAEKT DYVNLIQELA PKYAATHPKT EL |

Active fragments of MANF or CDNF can include short peptides with a length of about 4-40 amino acids; for example, about: 4-40, 4-35, 4-30, 4-25, 4-20, 4-15, 4-10, 5-40, 6-40, 7-40, 8-40, 5-35, 5-30, 5-25, 5-20, 5-15, 5-10, 6-35, 6-30, 6-25, 6-20, 6-15, 6-10, 7-35, 7-30, 7-25, 7-20, 7-15, 7-10, 8-35, 8-30, 8-25, 8-20, or 8-15 amino acids. For example, the preferred peptides can consist of 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 amino acids. The peptides may comprise any of the naturally occurring amino acids such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine as well as non-conventional or modified amino acids. The peptide can have 70, 80, 85, 90, 95, 96, 97, 98, 99, or 100% homology (or identity) with the sequence of human CDNF or MANF protein. In some embodiments, the peptides comprise the sequence CXXC. In some embodiments, the peptides comprise the sequence CKGC or CRAC (see, e.g., WO 2013/034805). These peptides can be cell permeable. Active fragments of MANF can include any of the short peptides disclosed in Table 3. Active fragments of CDNF can include any of the short peptides disclosed in Table 4.

TABLE 3

Short peptides of human MANF.

| SEQ ID NO | SEQUENCE |
|---|---|
| SEQ ID NO: 8 | ILDDWGETCKGCAEKSDYIRKINELMPKYAPKAASARTDL |
| SEQ ID NO: 9 | LDDWGETCKGCAEKSDYIRKINELMPKYAPKAASARTDL |
| SEQ ID NO: 10 | DDWGETCKGCAEKSDYIRKINELMPKYAPKAASARTDL |
| SEQ ID NO: 11 | DWGETCKGCAEKSDYIRKINELMPKYAPKAASARTDL |
| SEQ ID NO: 12 | WGETCKGCAEKSDYIRKINELMPKYAPKAASARTDL |
| SEQ ID NO: 13 | GETCKGCAEKSDYIRKINELMPKYAPKAASARTDL |
| SEQ ID NO: 14 | ETCKGCAEKSDYIRKINELMPKYAPKAASARTDL |
| SEQ ID NO: 15 | TCKGCAEKSDYIRKINELMPKYAPKAASARTDL |
| SEQ ID NO: 16 | CKGCAEKSDYIRKINELMPKYAPKAASARTDL |
| SEQ ID NO: 17 | CKGCAEKSDYIRKIN |
| SEQ ID NO: 18 | TCKGCAEKSDYIRKI |
| SEQ ID NO: 19 | ETCKGCAEKSDYIRK |
| SEQ ID NO: 20 | GETCKGCAEKSDYIR |
| SEQ ID NO: 21 | WGETCKGCAEKSDYI |
| SEQ ID NO: 22 | DWGETCKGCAEKSDY |
| SEQ ID NO: 23 | DDWGETCKGCAEKSD |
| SEQ ID NO: 24 | LDDWGETCKGCAEKS |
| SEQ ID NO: 25 | ILDDWGETCKGCAEK |
| SEQ ID NO: 26 | KILDDWGETCKGCAE |
| SEQ ID NO: 27 | KKILDDWGETCKGCA |
| SEQ ID NO: 28 | LKKILDDWGETCKGC |
| SEQ ID NO: 29 | CKGCAEKSDYIRKI |
| SEQ ID NO: 30 | TCKGCAEKSDYIRK |
| SEQ ID NO: 31 | ETCKGCAEKSDYIR |
| SEQ ID NO: 32 | GETCKGCAEKSDYI |
| SEQ ID NO: 33 | WGETCKGCAEKSDY |
| SEQ ID NO: 34 | DWGETCKGCAEKSD |
| SEQ ID NO: 35 | DDWGETCKGCAEKS |
| SEQ ID NO: 36 | LDDWGETCKGCAEK |
| SEQ ID NO: 37 | ILDDWGETCKGCAE |
| SEQ ID NO: 38 | KILDDWGETCKGCA |
| SEQ ID NO: 39 | KKILDDWGETCKGC |
| SEQ ID NO: 40 | CKGCAEKSDYIRK |
| SEQ ID NO: 41 | TCKGCAEKSDYIR |
| SEQ ID NO: 42 | ETCKGCAEKSDYI |
| SEQ ID NO: 43 | GETCKGCAEKSDY |
| SEQ ID NO: 44 | WGETCKGCAEKSD |
| SEQ ID NO: 45 | DWGETCKGCAEKS |
| SEQ ID NO: 46 | DDWGETCKGCAEK |
| SEQ ID NO: 47 | LDDWGETCKGCAE |
| SEQ ID NO: 48 | ILDDWGETCKGCA |
| SEQ ID NO: 49 | KILDDWGETCKGC |
| SEQ ID NO: 50 | CKGCAEKSDYIR |
| SEQ ID NO: 51 | TCKGCAEKSDYI |
| SEQ ID NO: 52 | ETCKGCAEKSDY |
| SEQ ID NO: 53 | GETCKGCAEKSD |
| SEQ ID NO: 54 | WGETCKGCAEKS |
| SEQ ID NO: 55 | DWGETCKGCAEK |
| SEQ ID NO: 56 | DDWGETCKGCAE |
| SEQ ID NO: 57 | LDDWGETCKGCA |
| SEQ ID NO: 58 | ILDDWGETCKGC |
| SEQ ID NO: 59 | CKGCAEKSDYI |
| SEQ ID NO: 60 | TCKGCAEKSDY |
| SEQ ID NO: 61 | ETCKGCAEKSD |
| SEQ ID NO: 62 | GETCKGCAEKS |
| SEQ ID NO: 63 | WGETCKGCAEK |
| SEQ ID NO: 64 | DWGETCKGCAE |
| SEQ ID NO: 65 | DDWGETCKGCA |
| SEQ ID NO: 66 | LDDWGETCKGC |
| SEQ ID NO: 67 | CKGCAEKSDY |
| SEQ ID NO: 68 | TCKGCAEKSD |
| SEQ ID NO: 69 | ETCKGCAEKS |
| SEQ ID NO: 70 | GETCKGCAEK |
| SEQ ID NO: 71 | WGETCKGCAE |
| SEQ ID NO: 72 | DWGETCKGCA |
| SEQ ID NO: 73 | DDWGETCKGC |
| SEQ ID NO: 74 | CKGCAEKSD |
| SEQ ID NO: 75 | TCKGCAEKS |
| SEQ ID NO: 76 | ETCKGCAEK |
| SEQ ID NO: 77 | GETCKGCAE |
| SEQ ID NO: 78 | WGETCKGCA |
| SEQ ID NO: 79 | DWGETCKGC |
| SEQ ID NO: 80 | CKGCAEKS |
| SEQ ID NO: 81 | TCKGCAEK |

TABLE 3-continued

Short peptides of human MANF.

| SEQ ID NO | SEQUENCE |
| --- | --- |
| SEQ ID NO: 82 | ETCKGCAE |
| SEQ ID NO: 83 | GETCKGCA |
| SEQ ID NO: 84 | WGETCKGC |
| SEQ ID NO: 85 | CKGCAEK |
| SEQ ID NO: 86 | TCKGCAE |
| SEQ ID NO: 87 | ETCKGCA |
| SEQ ID NO: 88 | GETCKGC |
| SEQ ID NO: 89 | CKGCAE |
| SEQ ID NO: 90 | TCKGCA |
| SEQ ID NO: 91 | ETCKGC |
| SEQ ID NO: 92 | CKGCA |
| SEQ ID NO: 93 | TCKGC |
| SEQ ID NO: 94 | CKGC |

TABLE 4

Short peptides of human CDNF.

| SEQ ID NO | SEQUENCE |
| --- | --- |
| SEQ ID NO: 95 | KQILHSWGEECRACAEKTDYVNLIQELAPKYAATHPKTEL |
| SEQ ID NO: 96 | QILHSWGEECRACAEKTDYVNLIQELAPKYAATHPKTEL |
| SEQ ID NO: 97 | ILHSWGEECRACAEKTDYVNLIQELAPKYAATHPKTEL |
| SEQ ID NO: 98 | LHSWGEECRACAEKTDYVNLIQELAPKYAATHPKTEL |
| SEQ ID NO: 99 | HSWGEECRACAEKTDYVNLIQELAPKYAATHPKTEL |
| SEQ ID NO: 100 | SWGEECRACAEKTDYVNLIQELAPKYAATHPKTEL |
| SEQ ID NO: 101 | WGEECRACAEKTDYVNLIQELAPKYAATHPKTEL |
| SEQ ID NO: 102 | GEECRACAEKTDYVNLIQELAPKYAATHPKTEL |
| SEQ ID NO: 103 | EECRACAEKTDYVNLIQELAPKYAATHPKTEL |
| SEQ ID NO: 104 | ECRACAEKTDYVNLIQELAPKYAATHPKTEL |
| SEQ ID NO: 105 | CRACAEKTDYVNLIQELAPKYAATHPKTEL |
| SEQ ID NO: 106 | LKQILHSWGEECRAC |
| SEQ ID NO: 107 | KQILHSWGEECRACA |
| SEQ ID NO: 108 | QILHSWGEECRACAE |
| SEQ ID NO: 109 | ILHSWGEECRACAEK |
| SEQ ID NO: 110 | LHSWGEECRACAEKT |
| SEQ ID NO: 111 | HSWGEECRACAEKTD |
| SEQ ID NO: 112 | SWGEECRACAEKTDY |
| SEQ ID NO: 113 | WGEECRACAEKTDYV |
| SEQ ID NO: 114 | GEECRACAEKTDYVN |
| SEQ ID NO: 115 | EECRACAEKTDYVNL |
| SEQ ID NO: 116 | ECRACAEKTDYVNLI |
| SEQ ID NO: 117 | CRACAEKTDYVNLIQ |
| SEQ ID NO: 118 | KQILHSWGEECRAC |
| SEQ ID NO: 119 | QILHSWGEECRACA |
| SEQ ID NO: 120 | ILHSWGEECRACAE |
| SEQ ID NO: 121 | LHSWGEECRACAEK |
| SEQ ID NO: 122 | HSWGEECRACAEKT |
| SEQ ID NO: 123 | SWGEECRACAEKTD |
| SEQ ID NO: 124 | WGEECRACAEKTDY |
| SEQ ID NO: 125 | GEECRACAEKTDYV |
| SEQ ID NO: 126 | EECRACAEKTDYVN |
| SEQ ID NO: 127 | ECRACAEKTDYVNL |
| SEQ ID NO: 128 | CRACAEKTDYVNLI |
| SEQ ID NO: 129 | QILHSWGEECRAC |
| SEQ ID NO: 130 | ILHSWGEECRACA |
| SEQ ID NO: 131 | LHSWGEECRACAE |
| SEQ ID NO: 132 | HSWGEECRACAEK |
| SEQ ID NO: 133 | SWGEECRACAEKT |
| SEQ ID NO: 134 | WGEECRACAEKTD |
| SEQ ID NO: 135 | GEECRACAEKTDY |
| SEQ ID NO: 136 | EECRACAEKTDYV |
| SEQ ID NO: 137 | ECRACAEKTDYVN |
| SEQ ID NO: 138 | CRACAEKTDYVNL |
| SEQ ID NO: 139 | ILHSWGEECRAC |
| SEQ ID NO: 140 | LHSWGEECRACA |
| SEQ ID NO: 141 | HSWGEECRACAE |
| SEQ ID NO: 142 | SWGEECRACAEK |
| SEQ ID NO: 143 | WGEECRACAEKT |
| SEQ ID NO: 144 | GEECRACAEKTD |
| SEQ ID NO: 145 | EECRACAEKTDY |
| SEQ ID NO: 146 | ECRACAEKTDYV |
| SEQ ID NO: 147 | CRACAEKTDYVN |
| SEQ ID NO: 148 | LHSWGEECRAC |
| SEQ ID NO: 149 | HSWGEECRACA |

TABLE 4-continued

Short peptides of human CDNF.

| SEQ ID NO | SEQUENCE |
| --- | --- |
| SEQ ID NO: 150 | SWGEECRACAE |
| SEQ ID NO: 151 | WGEECRACAEK |
| SEQ ID NO: 152 | GEECRACAEKT |
| SEQ ID NO: 153 | EECRACAEKTD |
| SEQ ID NO: 154 | ECRACAEKTDY |
| SEQ ID NO: 155 | CRACAEKTDYV |
| SEQ ID NO: 156 | HSWGEECRAC |
| SEQ ID NO: 157 | SWGEECRACA |
| SEQ ID NO: 158 | WGEECRACAE |
| SEQ ID NO: 159 | GEECRACAEK |
| SEQ ID NO: 160 | EECRACAEKT |
| SEQ ID NO: 161 | ECRACAEKTD |
| SEQ ID NO: 162 | CRACAEKTDY |
| SEQ ID NO: 163 | SWGEECRAC |
| SEQ ID NO: 164 | WGEECRACA |
| SEQ ID NO: 165 | GEECRACAE |
| SEQ ID NO: 166 | EECRACAEK |
| SEQ ID NO: 167 | ECRACAEKT |
| SEQ ID NO: 168 | CRACAEKTD |
| SEQ ID NO: 169 | WGEECRAC |
| SEQ ID NO: 170 | GEECRACA |
| SEQ ID NO: 171 | EECRACAE |
| SEQ ID NO: 172 | ECRACAEK |
| SEQ ID NO: 173 | CRACAEKT |
| SEQ ID NO: 174 | GEECRAC |
| SEQ ID NO: 175 | EECRACA |
| SEQ ID NO: 176 | ECRACAE |
| SEQ ID NO: 177 | CRACAEK |
| SEQ ID NO: 178 | EECRAC |
| SEQ ID NO: 179 | ECRACA |
| SEQ ID NO: 180 | CRACAE |
| SEQ ID NO: 181 | ECRAC |
| SEQ ID NO: 182 | CRACA |
| SEQ ID NO: 183 | CRAC |

Neuroprotective peptides can be conjugated to a detectable chemical or biochemical moiety such as a FITC-label. As used herein, a "detectable chemical or biochemical moiety" means a tag that exhibits an amino acid sequence or a detectable chemical or biochemical moiety for the purpose of facilitating detection of the peptide; such as a detectable molecule selected from among: a visible, fluorescent, chemiluminescent, or other detectable dye; an enzyme that is detectable in the presence of a substrate, e.g., an alkaline phosphatase with NBT plus BCIP or a peroxidase with a suitable substrate; a detectable protein, e.g., a green fluorescent protein. Preferably, the tag does not prevent or hinder the penetration of the peptide into the target cell.

Effective Amounts

With respect to neuroprotective peptides disclosed herein, (e.g., MANF family proteins or active fragments thereof), the effective amount can vary, as described herein.

The effective amount of a neuroprotective peptide (e.g., MANF family proteins or active fragments thereof, e.g., MANF, CDNF, or fragments thereof) can expressed as a weight of the neuroprotective peptide. The weights disclosed should be interpreted as an amount that is administered in a single dose to a site of administration. For example, the effective amount of the neuroprotective peptide can be about: 0.5 µg-2.5 µg, 0.5 µg-5 µg, 0.5 µg-7.5 µg, 0.5 µg-12.5 µg, 0.5 µg-25 µg, 0.5 µg-50 µg, 0.5 µg-75 µg, 0.5 µg-100 µg, 0.5 µg-150 µg, 0.5 µg-250 µg, 0.5 µg-500 µg, 0.5 µg-1000 µg, 0.5 µg-1250 µg, 0.5 µg-2500 µg, 1 µg-2.5 µg, 1 µg-5 µg, 1 µg-7.5 µg, 1 µg-12.5 µg, 1 µg-25 µg, 1 µg-50 µg, 1 µg-75 µg, 1 µg-100 µg, 1 µg-150 µg, 1 µg-250 µg, 1 µg-500 µg, 1 µg-1000 µg, 1 µg-1250 µg, 1 µg-2500 µg, 2.5 µg-5 µg, 2.5 µg-7.5 µg, 2.5 µg-12.5 µg, 2.5 µg-25 µg, 2.5 µg-50 µg, 2.5 µg-75 µg, 2.5 µg-100 µg, 2.5 µg-150 µg, 2.5 µg-250 µg, 2.5 µg-500 µg, 2.5 µg-1000 µg, 2.5 µg-1250 µg, 2.5 µg-2500 µg, 5 µg-7.5 µg, 5 µg-12.5 µg, 5 µg-25 µg, 5 µg-50 µg, 5 µg-75 µg, 5 µg-100 µg, 5 µg-150 µg, 5 µg-250 µg, 5 µg-500 µg, 5 µg-1000 µg, 5 µg-1250 µg, 5 µg-2500 µg, 7.5 µg-12.5 µg, 7.5 µg-25 µg, 7.5 µg-50 µg, 7.5 µg-75 µg, 7.5 µg-100 µg, 7.5 µg-150 µg, 7.5 µg-250 µg, 7.5 µg-500 µg, 7.5 µg-1000 µg, 7.5 µg-1250 µg, 7.5 µg-2500 µg, 12.5 µg-25 µg, 12.5 µg-50 µg, 12.5 µg-75 µg, 12.5 µg-100 µg, 12.5 µg-150 µg, 12.5 µg-250 µg, 12.5 µg-500 µg, 12.5 µg-1000 µg, 12.5 µg-1250 µg, 12.5 µg-2500 µg, 25 µg-50 µg, 25 µg-75 µg, 25 µg-100 µg, 25 µg-150 µg, 25 µg-250 µg, 25 µg-500 µg, 25 µg-1000 µg, 25 µg-1250 µg, 25 µg-2500 µg, 50 µg-75 µg, 50 µg-100 µg, 50 µg-150 µg, 50 µg-250 µg, 50 µg-500 µg, 50 µg-1000 µg, 50 µg-1250 µg, 50 µg-2500 µg, 75 µg-100 µg, 75 µg-150 µg, 75 µg-250 µg, 75 µg-500 µg, 75 µg-1000 µg, 75 µg-1250 µg, 75 µg-2500 µg, 100 µg-150 µg, 100 µg-250 µg, 100 µg-500 µg, 100 µg-1000 µg, 100 µg-1250 µg, 100 µg-2500 µg, 150 µg-250 µg, 150 µg-500 µg, 150 µg-1000 µg, 150 µg-1250 µg, 150 µg-2500 µg, 250 µg-500 µg, 250 µg-1000 µg, 250 µg-1250 µg, 250 µg-2500 µg, 500 µg-1000 µg, 500 µg-1250 µg, 500 µg-2500 µg, 1000 µg-1250 µg, 1000 µg-2500 µg, or 1250 µg-2500 µg. The effective amount can be about 1 µg-500 µg. The effective amount can be about 5 µg-250 µg.

The effective amount of a neuroprotective peptide (e.g., MANF family proteins or active fragments thereof, e.g., MANF, CDNF, or fragments thereof) can be at least about: 0.5 µg, 2.5 µg, 5 µg, 7.5 µg, 12.5 µg, 25 µg, 50 µg, 75 µg, 100 µg, 150 µg, 250 µg, 500 µg, 1000 µg, 1250 µg, or 2500 µg.

The effective amount of a neuroprotective peptide (e.g., MANF family proteins or active fragments thereof, e.g., MANF, CDNF, or fragments thereof) can be less than about: 0.5 µg, 2.5 µg, 5 µg, 7.5 µg, 12.5 µg, 25 µg, 50 µg, 75 µg, 100 µg, 150 µg, 250 µg, 500 µg, 1000 µg, 1250 µg, or 2500 µg.

The effective amount of a neuroprotective peptide (e.g., MANF family proteins or active fragments thereof, e.g., MANF, CDNF, or fragments thereof) can be in a formulation having a wide range of concentrations. For example, the effective amount of the neuroprotective peptide can be in a formulation at a concentration of about: 0.1 µMol-500 µMol, 0.1 µMol-100 µMol, 0.1 µMol-50 µMol, 0.1 µMol-20 µMol, 0.1 µMol-10 µMol, 0.1 µMol-5 µMol, 0.1 µMol-3 µMol, 0.1 µMol-1 µMol, 0.1 µMol-0.5 µMol, 0.5 µMol-500 µMol, 0.5 µMol-100 µMol, 0.5 µMol-50 µMol, 0.5 µMol-20 µMol, 0.5 µMol-10 µMol, 0.5 µMol-5 µMol, 0.5 µMol-3 µMol, 0.5 µMol-1 µMol, 1 µMol-500 µMol, 1 µMol-100 µMol, 1 µMol-50 µMol, 1 µMol-20 µMol, 1 µMol-10 µMol, 1 µMol-5 µMol, 1 µMol-3 µMol, 3 µMol-500 µMol, 3 µMol-100 µMol, 3 µMol-50 µMol, 3 µMol-20 µMol, 3 µMol-10 µMol, 3 µMol-5 µMol, 5 µMol-500 µMol, 5 µMol-100 µMol, 5 µMol-50 µMol, 5 µMol-20 µMol, 5 µMol-10 µMol, 10 µMol-500 µMol, 10 µMol 100 µMol, 10 µMol-50 µMol, 10 µMol-20 µMol, 20 µMol-500 µMol, 20 µMol-100 µMol, 20 µMol-50 µMol, 50 µMol-500 µMol, 50 µMol-100 µMol, or 100 µMol-500 µMol. In some examples, the effective amount of the neuroprotective peptide is in a formulation at a concentration of about: 1 µMol 50 µMol. In some examples, the effective amount of the neuroprotective peptide is in a formulation at a concentration of about: 3 µMol-20 µMol.

The effective amount of the neuroprotective peptide in a formulation can be administered in a range of volumes. The range of volumes can depend upon the route of administration. The range of volumes can depend upon the site of administration. Exemplary volume ranges include about: 1 µL, 5 µL, 1 µL-25 µL, 1 µL-50 µL, 1 µL-100 µL, 1 µL-200 µL, 1 µL-250 µL, 1 µL-300 µL, 1 µL-500 µL, 1 µL-1000 µL, 5 µL-25 µL, 5 µL-50 µL, 5 µL-100 µL, 5 µL-200 µL, 5 µL-250 µL, 5 µL-300 µL, 5 µL-500 µL, 5 µL 1000 µL, 25 µL-50 µL, 25 µL-100 µL, 25 µL-200 µL, 25 µL-250 µL, 25 µL-300 µL, 25 µL-500 µL, 25 µL-1000 µL, 50 µL-100 µL, 50 µL 200 µL, 50 µL-250 µL, 50 µL-300 µL, 50 µL-500 µL, 50 µL-1000 µL, 100 µL-200 µL, 100 µL-250 µL, 100 µL-300 µL, 100 µL-500 µL, 100 µL 1000 µL, 200 µL-250 µL, 200 µL-300 µL, 200 µL-500 µL, 200 µL-1000 µL, 250 µL-500 µL, 250 µL-1000 µL, 300 µL-500 µL, 300 µL-1000, or 500 µL-1000 µL. The volume range can be about 50 µL-1000 µL. The volume range can be about 100 µL-500 µL. The volume range can be about 200 µL-300 µL.

Viral Therapy/Gene Therapy

Broadly, gene therapy seeks to transfer new genetic material to the cells of a patient with resulting therapeutic benefit to the patient. Such benefits include treatment or prophylaxis of a broad range of diseases, disorders and other conditions.

The methods provided herein can comprise delivery of a transgene to a subject's organ or body region affected by cell death-related sensory loss, or to an organ or body region where prevention of cell death-related sensory loss is desired, by administering a recombinant viral vector containing a transgene, wherein the delivery is under conditions that favor expression of the transgene. For example, methods of gene therapy known in the art are disclosed in US Patent Application No. 20090069261, which is hereby incorporated by reference in its entirety.

Unless specifically indicated to the contrary, expression of the transgene is not limited to translation to a polypeptide or protein but also includes replication and/or transcription of the transgene polynucleotide.

The vector comprising the transgene can be an expression vector that expresses a MANF family protein. The MANF family protein can be MANF or an active fragment thereof. The transgene can comprise a nucleotide sequence that encodes for MANF or an active fragment thereof, wherein the nucleotide sequence has at least about 70% identity to SEQ ID NO: 184. The transgene can comprise a nucleotide sequence that encodes for MANF or an active fragment thereof, wherein the nucleotide sequence has at least about 80% identity to SEQ ID NO: 184. The transgene can comprise a nucleotide sequence that encodes for MANF or an active fragment thereof, wherein the nucleotide sequence has at least about 90% identity to SEQ ID NO: 184. The transgene can comprise a nucleotide sequence that encodes for MANF or an active fragment thereof, wherein the nucleotide sequence has at least about 95% identity to SEQ ID NO: 184. The transgene can comprise a nucleotide sequence that encodes for MANF or an active fragment thereof, wherein the nucleotide sequence is SEQ ID NO: 184.

The vector comprising the transgene can be an expression vector that expresses a MANF family protein. The MANF family protein can be MANF or an active fragment thereof. The transgene can comprise a nucleotide sequence that encodes for MANF or an active fragment thereof, wherein the nucleotide sequence has at least about 70% identity to SEQ ID NO: 185. The transgene can comprise a nucleotide sequence that encodes for MANF or an active fragment thereof, wherein the nucleotide sequence has at least about 80% identity to SEQ ID NO: 185. The transgene can comprise a nucleotide sequence that encodes for MANF or an active fragment thereof, wherein the nucleotide sequence has at least about 90% identity to SEQ ID NO: 185. The transgene can comprise a nucleotide sequence that encodes for MANF or an active fragment thereof, wherein the nucleotide sequence has at least about 95% identity to SEQ ID NO: 185. The transgene can comprise a nucleotide sequence that encodes for MANF or an active fragment thereof, wherein the nucleotide sequence is SEQ ID NO: 185.

The vector comprising the transgene can be an expression vector that expresses a MANF family protein. The MANF family protein can be a pro-MANF or an active fragment thereof. In one example, the transgene can comprise a nucleotide sequence that encodes for a peptide sequence that has at least about 80% identity to SEQ ID NO:1. In another example, the transgene can comprise a nucleotide sequence that encodes for a peptide sequence that has at least about 90% identity to SEQ ID NO:1. In another example, the transgene can comprise a nucleotide sequence that encodes for a peptide sequence that has at least about 95% identity to SEQ ID NO:1. In another example, the transgene can comprise a nucleotide sequence that encodes for a peptide sequence that has 100% identity with SEQ ID NO:1. In any of these examples, the peptide sequence can have a length that is at least about 5% the length of SEQ ID NO:1. In any of these examples, the peptide sequence can have a length that is at least about 50% the length of SEQ ID NO:1. In any of these examples, the peptide sequence can have a length that is at least about 80% the length of SEQ ID NO:1. In any of these examples, the peptide sequence can have a length that is at least about 90% the length of SEQ ID NO:1. In any of these examples, the peptide sequence can have a length that is at least about 95% the length of SEQ ID NO:1. The peptide sequence, in any of these examples, can also have a maximum length. The maximum length can be, e.g., 100%, 90%, 80%, 70%, 60%, 50%, or 25% the length of SEQ ID NO:1.

The vector comprising the transgene can be an expression vector that expresses a MANF family protein. The MANF family protein can be a pro-MANF or an active fragment thereof. In one example, the transgene can comprise a nucleotide sequence that encodes for a peptide sequence that has at least about 80% identity to SEQ ID NO:2. In another example, the transgene can comprise a nucleotide sequence that encodes for a peptide sequence that has at least about 90% identity to SEQ ID NO:2. In another example, the transgene can comprise a nucleotide sequence that encodes for a peptide sequence that has at least about 95% identity to SEQ ID NO:2. In another example, the transgene can comprise a nucleotide sequence that encodes for a peptide sequence that has 100% identity with SEQ ID NO:2. In any of these examples, the peptide sequence can have a length that is at least about 5% the length of SEQ ID NO:2. In any of these examples, the peptide sequence can have a length that is at least about 50% the length of SEQ ID NO:2. In any of these examples, the peptide sequence can have a length that is at least about 80% the length of SEQ ID NO:2. In any of these examples, the peptide sequence can have a length that is at least about 90% the length of SEQ ID NO:2. In any of these examples, the peptide sequence can have a length that is at least about 95% the length of SEQ ID NO:2. The peptide sequence, in any of these examples, can also have a maximum length. The maximum length can be, e.g., 100%, 90%, 80%, 70%, 60%, 50%, or 25% the length of SEQ ID NO:2.

The vector comprising the transgene can be an expression vector that expresses a MANF family protein. The MANF family protein can be a mature or secreted form of MANF, or an active fragment thereof. In one example, the transgene can comprise a nucleotide sequence that encodes for a peptide sequence that has at least about 80% identity to SEQ ID NO:3. In another example, the transgene can comprise a nucleotide sequence that encodes for a peptide sequence that has at least about 90% identity to SEQ ID NO:3. In another example, the transgene can comprise a nucleotide sequence that encodes for a peptide sequence that has at least about 95% identity to SEQ ID NO:3. In another example, the transgene can comprise a nucleotide sequence that encodes for a peptide sequence that has 100% identity with SEQ ID NO:3. In any of these examples, the peptide sequence can have a length that is at least about 5% the length of SEQ ID NO:3. In any of these examples, the peptide sequence can have a length that is at least about 50% the length of SEQ ID NO:3. In any of these examples, the peptide sequence can have a length that is at least about 80% the length of SEQ ID NO:3. In any of these examples, the peptide sequence can have a length that is at least about 90% the length of SEQ ID NO:3. In any of these examples, the peptide sequence can have a length that is at least about 95% the length of SEQ ID NO:3. The peptide sequence, in any of these examples, can also have a maximum length. The maximum length can be, e.g., 100%, 90%, 80%, 70%, 60%, 50%, or 25% the length of SEQ ID NO:3.

The vector comprising the transgene can be an expression vector that expresses a MANF family protein. The MANF family protein can be a synthetic form of MANF, or an active fragment thereof. In one example, the transgene can comprise a nucleotide sequence that encodes for a peptide sequence that has at least about 80% identity to SEQ ID NO:4. In another example, the transgene can comprise a nucleotide sequence that encodes for a peptide sequence that has at least about 90% identity to SEQ ID NO:4. In another example, the transgene can comprise a nucleotide sequence that encodes for a peptide sequence that has at least about 95% identity to SEQ ID NO:4. In another example, the transgene can comprise a nucleotide sequence that encodes for a peptide sequence that has 100% identity with SEQ ID NO:4. In any of these examples, the peptide sequence can have a length that is at least about 5% the length of SEQ ID NO:4. In any of these examples, the peptide sequence can have a length that is at least about 50% the length of SEQ ID NO:4. In any of these examples, the peptide sequence can have a length that is at least about 80% the length of SEQ ID NO:4. In any of these examples, the peptide sequence can have a length that is at least about 90% the length of SEQ ID NO:4. In any of these examples, the peptide sequence can have a length that is at least about 95% the length of SEQ ID NO:4. The peptide sequence, in any of these examples, can also have a maximum length. The maximum length can be, e.g., 100%, 90%, 80%, 70%, 60%, 50%, or 25% the length of SEQ ID NO:4.

The vector comprising the transgene can be an expression vector that expresses a MANF family protein. The MANF family protein can be CDNF, or an active fragment thereof. The transgene can comprise a nucleotide sequence that encodes for CDNF or an active fragment thereof, wherein the nucleotide sequence has at least about 70% identity to SEQ ID NO:186. The transgene can comprise a nucleotide sequence that encodes for CDNF or an active fragment thereof, wherein the nucleotide sequence has at least about 80% identity to SEQ ID NO:186. The transgene can comprise a nucleotide sequence that encodes for CDNF or an active fragment thereof, wherein the nucleotide sequence has at least about 90% identity to SEQ ID NO:186. The transgene can comprise a nucleotide sequence that encodes for CDNF or an active fragment thereof, wherein the nucleotide sequence has at least about 95% identity to SEQ ID NO:186. The transgene can comprise a nucleotide sequence that encodes for CDNF or an active fragment thereof, wherein the nucleotide sequence is SEQ ID NO:186.

TABLE 5

Human MANF cDNA Sequences.

| SEQ ID | NAME | ASCESSION Number | SEQUENCE |
| --- | --- | --- | --- |
| SEQ ID NO: 184 | Human Pro-MANF cDNA | NM_006010 | agctacggcg cgcggccggg acttggaggc ggtgcggcgc ggcgggtgcg gttcagtcgg tcggcggcgg cagcggagga ggaggaggag gaggaggatg aggaggatga ggaggatgtg ggccacgcag gggctggcgg tggcgctggc tctgagcgtg ctgccgggca gccgggcgct gcggccgggc gactgcgaag tttgtatttc ttatctggga agattttacc aggacctcaa agacagagat gtcacattct caccagccac tattgaaaac gaacttataa agttctgccg ggaagcaaga ggcaaagaga atcggttgtg ctactatatc ggggccacag atgatgcagc caccaaaatc atcaatgagg tatcaaagcc tctggcccac cacatccctg tggagaagat ctgtgagaag cttaagaaga aggacagcca gatatgtgag cttaagtatg acaagcagat cgacctgagc acagtggacc tgaagaagct ccgagttaaa gagctgaaga agattctgga tgactggggg gagacatgca aaggctgtgc agaaaagtct gactacatcc ggaagataaa tgaactgatg cctaaatatg cccccaaggc agccagtgca cggaccgatt tgtagtctgc tcaatctctg ttgcacctga gggggaaaaa acagttcaac tgcttactcc caaaacagcc tttttgtaat ttatttttta agtgggctcc tgacaatact gtatcagatg tgaagcctgg |

TABLE 5-continued

Human MANF cDNA Sequences.

| SEQ ID | NAME | ASCESSION Number | SEQUENCE |
|---|---|---|---|
| | | | agctttcctg atgatgctgg |
| | | | ccctacagta cccccatgag |
| | | | gggattccct tccttctgtt |
| | | | gctggtgtac tctaggactt |
| | | | caaagtgtgt ctgggatttt |
| | | | tttattaaag aaaaaaaatt |
| | | | tctagctgtc cttgcagaat |
| | | | tatagtgaat accaaaatgg |
| | | | ggttttgccc caggaggctc |
| | | | ctaaaaaaaa aaaaaaaaaa |
| | | | aaaaaaaaaa aaa |
| SEQ ID NO: 185 | Human Pro-MANF cDNA (Coding Region Only) | | atgtgggcca cgcaggggct ggcggtggcg ctggctctga gcgtgctgcc gggcagccgg gcgctgcggc cgggcgactg cgaagtttgt atttcttatc tgggaagatt ttaccaggac ctcaaagaca gagatgtcac attctcacca gccactattg aaaacgaact tataaagttc tgccgggaag caagaggcaa agagaatcgg ttgtgctact atatcggggc cacagatgat gcagccacca aaatcatcaa tgaggtatca aagcctctgg cccaccacat ccctgtggag aagatctgtg agaagcttaa gaagaaggac agccagatat gtgagcttaa gtatgacaag cagatcgacc tgagcacagt ggacctgaag aagctccgag ttaaagagct gaagaagatt ctggatgact gggggagac atgcaaaggc tgtgcagaaa agtctgacta catccggaag ataaatgaac tgatgcctaa atatgccccc aaggcagcca gtgcacggac cgatttgtag |

The vector comprising the transgene can be an expression vector that expresses a MANF family protein. The MANF family protein can be CDNF, or an active fragment thereof. The transgene can comprise a nucleotide sequence that encodes for CDNF or an active fragment thereof, wherein the nucleotide sequence has at least about 70% identity to SEQ ID NO:187. The transgene can comprise a nucleotide sequence that encodes for CDNF or an active fragment thereof, wherein the nucleotide sequence has at least about 80% identity to SEQ ID NO:187. The transgene can comprise a nucleotide sequence that encodes for CDNF or an active fragment thereof, wherein the nucleotide sequence has at least about 90% identity to SEQ ID NO:187. The transgene can comprise a nucleotide sequence that encodes for CDNF or an active fragment thereof, wherein the nucleotide sequence has at least about 95% identity to SEQ ID NO:187. The transgene can comprise a nucleotide sequence that encodes for CDNF or an active fragment thereof, wherein the nucleotide sequence is SEQ ID NO: 187.

The vector comprising the transgene can be an expression vector that expresses a MANF family protein. The MANF family protein can be a pro-CDNF or an active fragment thereof. In one example, the transgene can comprise a nucleotide sequence that encodes for a peptide sequence that has at least about 80% identity to SEQ ID NO:5. In another example, the transgene can comprise a nucleotide sequence that encodes for a peptide sequence that has at least about 90% identity to SEQ ID NO:5. In another example, the transgene can comprise a nucleotide sequence that encodes for a peptide sequence that has at least about 95% identity to SEQ ID NO:5. In another example, the transgene can comprise a nucleotide sequence that encodes for a peptide sequence that has 100% identity with SEQ ID NO:5. In any of these examples, the peptide sequence can have a length that is at least about 5% the length of SEQ ID NO:5. In any of these examples, the peptide sequence can have a length that is at least about 50% the length of SEQ ID NO:5. In any of these examples, the peptide sequence can have a length that is at least about 80% the length of SEQ ID NO:5. In any of these examples, the peptide sequence can have a length that is at least about 90% the length of SEQ ID NO:5. In any of these examples, the peptide sequence can have a length that is at least about 95% the length of SEQ ID NO:5. The peptide sequence, in any of these examples, can also have a maximum length. The maximum length can be, e.g., 100%, 90%, 80%, 70%, 60%, 50%, or 25% the length of SEQ ID NO:5.

The vector comprising the transgene can be an expression vector that expresses a MANF family protein. The MANF family protein can be a mature or secreted form of CDNF, or an active fragment thereof. In one example, the transgene can comprise a nucleotide sequence that encodes for a peptide sequence that has at least about 80% identity to SEQ ID NO:6. In another example, the transgene can comprise a nucleotide sequence that encodes for a peptide sequence that has at least about 90% identity to SEQ ID NO:6. In another example, the transgene can comprise a nucleotide sequence that encodes for a peptide sequence that has at least about 95% identity to SEQ ID NO:6. In another example, the transgene can comprise a nucleotide sequence that encodes for a peptide sequence that has 100% identity with SEQ ID NO:6. In any of these examples, the peptide sequence can have a length that is at least about 5% the length of SEQ ID NO:6. In any of these examples, the peptide sequence can have a length that is at least about 50% the length of SEQ ID NO:6. In any of these examples, the peptide sequence can have a length that is at least about 80% the length of SEQ ID NO:6. In any of these examples, the peptide sequence can have a length that is at least about 90% the length of SEQ ID NO:6. In any of these examples, the peptide sequence can have a length that is at least about 95% the length of SEQ ID NO:6. The peptide sequence, in any of these examples, can also have a maximum length. The maximum length can be, e.g., 100%, 90%, 80%, 70%, 60%, 50%, or 25% the length of SEQ ID NO:6.

The vector comprising the transgene can be an expression vector that expresses a MANF family protein. The MANF family protein can be a synthetic form of CDNF, or an active fragment thereof. In one example, the transgene can comprise a nucleotide sequence that encodes for a peptide sequence that has at least about 80% identity to SEQ ID NO:7. In another example, the transgene can comprise a nucleotide sequence that encodes for a peptide sequence that has at least about 90% identity to SEQ ID NO:7. In another example, the transgene can comprise a nucleotide sequence that encodes for a peptide sequence that has at least about 95% identity to SEQ ID NO:7. In another example, the transgene can comprise a nucleotide sequence that encodes for a peptide sequence that has 100% identity with SEQ ID NO:7. In any of these examples, the peptide sequence can have a length that is at least about 5% the length of SEQ ID NO:7. In any of these examples, the peptide sequence can have a length that is at least about 50% the length of SEQ ID NO:7. In any of these examples, the peptide sequence can have a length that is at least about 80% the length of SEQ ID NO:7. In any of these examples, the peptide sequence can have a length that is at least about 90% the length of SEQ ID NO:7. In any of these examples, the peptide sequence can have a length that is at least about 95% the length of SEQ ID NO:7. The peptide sequence, in any of these examples, can also have a maximum length. The maximum length can be, e.g., 100%, 90%, 80%, 70%, 60%, 50%, or 25% the length of SEQ ID NO:7.

TABLE 6

Human CDNF cDNA Sequences.

| SEQ ID | NAME | ASCESSION Number | SEQUENCE |
|---|---|---|---|
| SEQ ID NO: 186 | Human CDNF cDNA | NM_001029954 | gcgcgggtgg cggaggcgat tgaagctgct ggcccagcat gtggtgcgcg agcccagttg ctgtggtggc cttttgcgcc gggcttttgg tctctcaccc ggtgctgacg cagggccagg aggccggggg gcggccaggg gccgactgtg aagtatgtaa agaattcttg aaccgattct acaagtcact gatagacaga ggagttaact tttcgctgga cactatagag aaagaattga tcagtttttg cttggacacc aaaggaaaag aaaaccgcct gtgctattat ctaggagcca caaaagacgc agccacaaag atcctaagtg aagtcactcg cccaatgagt gtgcatatgc ctgcaatgaa gatttgtgag aagctgaaga agttggatag ccagatctgt gagctgaaat atgaaaaaac actggacttg gcatcagttg acctgcggaa gatgagagtg gcagagctga agcagatcct gcatagctgg ggggaggagt gcagggcctg tgcagaaaaa actgactatg tgaatctcat tcaagagctg gcccccaagt atgcagcgac acacccccaaa acagagctct gatctccaat gccagcacat ttgtgacttg taattagaga gaaaagtgac tctctaggat atggacatgt tgattaagga taactgggaa tgcatcatat ttggtctcat gcttttttgtg ttggtattat tcctcagaat tttgttacgt gggtttatga gtgaaactaa tactactgat aacttacatt tgcagtgtac caaaagctaa aagttccttt ctcataagtt tcttggaatg actatgccag ttttcattgc ctgtctccta aaagtgacct actgacaaat tgatggagta aattgattcc aagaaagaag aaggcattca gagactcctc tctggatgca atttttaaaat atattggact aaaacaaaag acacaacagt cagcttatct aatgcacaac ttcaatccca aatacagaat caaaagtttt tttcaagtga attttctgtt ttcactctat attgtagctc tctttggtat cagaaatggt caggcaggag tactcgtttt tcccattgga agaaaaccca cttaaaccta cttaaagaaa atagagagat caagaaaccg tataagtata gccaatgttt ggcaattata tcaacattta cattgttaat tgaaccaagc |

TABLE 6-continued

Human CDNF cDNA Sequences.

| SEQ ID | NAME | ASCESSION Number | SEQUENCE |
|---|---|---|---|
| SEQ ID NO: 187 | Human CDNF cDNA (Coding region only) | | atgtggtgcg cgagcccagt tgctgtggtg gccttttgcg ccgggctttt ggtctctcac ccggtgctga cgcagggcca ggaggccggg gggcggccag gggccgactg tgaagtatgt aaagaattct tgaaccgatt ctacaagtca ctgatagaca gaggagttaa cttttcgctg gacactatag agaaagaatt gatcagtttt tgcttggaca ccaaaggaaa agaaaaccgc ctgtgctatt atctaggagc cacaaaagac gcagccacaa agatcctaag tgaagtcact cgcccaatga gtgtgcatat gcctgcaatg aagatttgtg agaagctgaa gaagttggat agccagatct gtgagctgaa atatgaaaaa acactggact tggcatcagt tgacctgcgg aagatgagag tggcagagct gaagcagatc ctgcatagct ggggggagga gtgcagggcc tgtgcagaaa aaactgacta tgtgaatctc attcaagagc tggcccccaa gtatgcagcg acacacccca aaacagagct ctga |

Viral expression vectors can be used in the methods disclosed herein. The viral expression vectors can comprise a transgene that expresses one or more neuroprotective peptides. The one or more neuroprotective peptides can be any of the neuroprotective peptides disclosed herein. The one or more neuroprotective peptides can comprise one or more MANF family proteins, or active fragments thereof. The one or more MANF family protein can be MANF, CDNF, or a combination thereof. In some embodiments, one or more neuroprotective peptides comprise MANF, or an active fragment thereof. In some embodiments, one or more neuroprotective peptides comprise CDNF, or an active fragment thereof.

Viruses useful as viral expression vectors include papovavirus, adenovirus, vaccinia virus, adeno-associated virus (AAV), herpesvirus, and retroviruses. Suitable retroviruses include the group consisting of HIV, SIV, FIV, EIAV, MoMLV.

Lentiviruses and adeno-associated viruses can integrate into the genome without cell divisions, and therefore can be useful in delivery of a transgene to neural cells.

AAV of any serotype can be used in the methods disclosed herein. The serotype of the viral vector can be AAV1, AAV2, AAV3, AAV4, MV5, AAV6, AAV7, and AAV8 (see, e.g., Gao et al. (2002) PNAS, 99:11854-11859; and Viral Vectors for Gene Therapy: Methods and Protocols, ed. Machida, Humana Press, 2003). Other serotype besides those listed herein can be used. Furthermore, pseudotyped AAV vectors may also be utilized in the methods described herein. Pseudotyped AAV vectors are those which contain the genome of one AAV serotype in the capsid of a second AAV serotype; for example, an AAV vector that contains the AAV2 capsid and the AAV1 genome or an AAV vector that contains the AAV5 capsid and the AAV 2 genome (Auricchio et al., (2001) Hum. Mol. Genet., 10(26):3075-81).

AAV vectors are derived from single-stranded (ss) DNA parvoviruses that are nonpathogenic for mammals (reviewed in Muzyscka (1992) Curr. Top. Microb. Immunol., 158:97-129). Briefly, AAV-based vectors have the rep and cap viral genes that account for 96% of the viral genome removed, leaving the two flanking 145-basepair (bp) inverted terminal repeats (ITRs), which are used to initiate viral DNA replication, packaging and integration. In the absence of helper virus, wild-type AAV integrates into the human host-cell genome with preferential site-specificity at chromosome 19q13.3 or it may remain expressed episomally. A single AAV particle can accommodate up to 5 kb of ssDNA, therefore leaving about 4.5 kb for a transgene and regulatory elements, which is typically sufficient. However, trans-splicing systems as described, for example, in U.S. Pat. No. 6,544,785, may nearly double this limit.

Lentiviruses, which can transduce a cell and integrate into its genome without cell division, can be used in the methods disclosed herein. Thus lentivirus can be a replication-defective lentivirus particle. Such a lentivirus particle can be produced from a lentiviral vector comprising a 5' lentiviral LTR, a tRNA binding site, a packaging signal, a promoter operably linked to a polynucleotide signal encoding one or more neuroprotective peptides, an origin of second strand DNA synthesis and a 3' lentiviral LTR. Methods for preparation and in vivo administration of lentivirus to neural cells are described in US 20020037281 (Methods for transducing neural cells using lentiviral vectors) and US 20020187951 (Lentiviral-mediated growth factor gene therapy for neurodegenerative diseases).

Construction of vectors for expression of one or more neuroprotective peptides can be accomplished using conventional techniques that do not require detailed explanation to one of ordinary skill in the art. For review, however, those of ordinary skill may wish to consult Maniatis et al., in Molecular Cloning: A Laboratory Manual, Cold Spring Harbor Laboratory, (NY 1982).

Chimeric expression constructs can be created, e.g., by amplifying a signal sequence and a nucleotide encoding a desired neuroprotective peptide by PCR and fusing these in overlapping PCR. As many signal sequences are relatively short, the 5' PCR primer used for amplifying the neuroprotective peptide coding sequence may include the sequence coding for the signal sequence as well as a TATA box and other regulatory elements.

Briefly, construction of recombinant expression vectors employs standard ligation techniques. For analysis to confirm correct sequences in vectors constructed, the genes are sequences using, for example, the method of Messing, et al., (Nucleic Acids Res., 9: 309-, 1981), the method of Maxam, et al., (Methods in Enzymology, 65: 499, 1980), or other suitable methods which will be known to those skilled in the art.

Expression of a gene is controlled at the transcription, translation or post-translation levels. Transcription initiation is an early and critical event in gene expression. This depends on the promoter and enhancer sequences and is influenced by specific cellular factors that interact with these sequences. The transcriptional unit of many genes consists of the promoter and in some cases enhancer or regulator elements (Banerji et al., Cell 27: 299 (1981); Corden et al., Science 209: 1406 (1980); and Breathnach and Chambon, Ann. Rev. Biochem. 50: 349 (1981)). For retroviruses, control elements involved in the replication of the retroviral genome reside in the long terminal repeat (LTR) (Weiss et al., eds., The molecular biology of tumor viruses: RNA tumor viruses, Cold Spring Harbor Laboratory, (NY 1982)). Moloney murine leukemia virus (MLV) and Rous sarcoma virus (RSV) LTRs contain promoter and enhancer sequences (Jolly et al., Nucleic Acids Res. 11: 1855 (1983); Capecchi et al., In: Enhancer and eukaryotic gene expression, Gulzman and Shenk, eds., pp. 101-102, Cold Spring Harbor Laboratories (NY 1991). Promoters that show long-term activity and are tissue- and even cell-specific are used in some embodiments. Non-limiting examples of promoters include, but are not limited to, the cytomegalovirus (CMV) promoter (Kaplitt et al. (1994) Nat. Genet. 8:148-154), CMV/human beta.3-globin promoter (Mandel et al. (1998) J. Neurosci. 18:4271-4284), GFAP promoter (Xu et al. (2001) Gene Ther. 8:1323-1332), the 1.8-kb neuron-specific enolase (NSE) promoter (Klein et at (1998) Exp. Neurol. 150:183-194), chicken beta actin (CBA) promoter (Miyazaki (1989) Gene 79:269-277), the beta.-glucuronidase (GUSB) promoter (Shipley et al. (1991) Genetics 10:1009-1018), and ubiquitin promoters such as those isolated from human ubiquitin A, human ubiquitin B, and human ubiquitin C as described in U.S. Pat. No. 6,667,174. To prolong expression, other regulatory elements may additionally be operably linked to the transgene, such as, e.g., the Woodchuck Hepatitis Virus Post-Regulatory Element (WPRE) (Donello et al. (1998) J. Virol. 72:5085-5092) or the bovine growth hormone (BGH) polyadenylation site.

In addition to using viral and non-viral promoters to drive transgene expression, an enhancer sequence may be used to increase the level of transgene expression. Enhancers can increase the transcriptional activity not only of their native gene but also of some foreign genes (Armelor, Proc. Natl. Acad. Sci. USA 70: 2702 (1973)). For example, in the present invention collagen enhancer sequences may be used with the collagen promoter 2 (I) to increase transgene expression. In addition, the enhancer element found in SV40 viruses may be used to increase transgene expression. This enhancer sequence consists of a 72 base pair repeat as described by Gruss et al., Proc. Natl. Acad. Sci. USA 78: 943 (1981); Benoist and Chambon, Nature 290: 304 (1981), and Fromm and Berg, J. Mol. Appl. Genetics, 1: 457 (1982), all of which are incorporated by reference herein. This repeat sequence can increase the transcription of many different viral and cellular genes when it is present in series with various promoters (Moreau et al., Nucleic Acids Res. 9: 6047 (1981).

Further expression enhancing sequences include but are not limited to Woodchuck hepatitis virus post-transcriptional regulation element, WPRE, SP163, rat Insulini1-intron or other introns, CMV enhancer, and Chicken [beta]-globin insulator or other insulators.

Transgene expression may also be increased for long term stable expression using cytokines to modulate promoter activity. Several cytokines have been reported to modulate the expression of transgene from collagen 2 (I) and LTR promoters (Chua et al., connective Tissue Res., 25: 161-170 (1990); Elias et al., Annals N.Y. Acad. Sci., 580: 233-244 (1990)); Seliger et al., J. Immunol. 141: 2138-2144 (1988) and Seliger et al., J. Virology 62: 619-621 (1988)). For example, transforming growth factor (TGF), interleukin (IL)-I, and interferon (INF) down regulate the expression of transgenes driven by various promoters such as LTR. Tumor necrosis factor (TNF) and TGF 1 up regulate, and may be used to control, expression of transgenes driven by a promoter. Other cytokines that may prove useful include basic fibroblast growth factor (bFGF) and epidermal growth factor (EGF).

Collagen promoter with the collagen enhancer sequence (Cobb (E)) may also be used to increase transgene expression by suppressing further any immune response to the vector that may be generated in a treated brain notwithstanding its immune-protected status. In addition, anti-inflammatory agents including steroids, for example dexamethasone, may be administered to the treated host immediately after vector composition delivery and continued, preferably, until any cytokine-mediated inflammatory response subsides. An immunosuppression agent such as cyclosporin may also be administered to reduce the production of interferons, which down-regulates LTR promoter and Coll (E) promoter-enhancer, and reduces transgene expression.

The vector may comprise further sequences such as a sequence coding for the Cre-recombinase protein, and LoxP sequences. A further way of ensuring temporary expression of the neublastin is through the use of the Cre-LoxP system which results in the excision of part of the inserted DNA sequence either upon administration of Cre-recombinase to the cells (Daewoong et al, Nature Biotechnology 19:929-933) or by incorporating a gene coding for the recombinase into the virus construct (Pluck, Int J Exp Path, 77:269-278). Incorporating a gene for the recombinase in the virus construct together with the LoxP sites and a structural gene (a neublastin in the present case) often results in expression of the structural gene for a period of approximately five days.

MANF Modulators/Small Molecules

MANF modulators are chemical or drug substances that up-regulate the expression of endogenous MANF family proteins, or increase the activity of MANF. Valproic acid is an exemplary MANF modulator.

Routes of Administration

The active ingredients (e.g., neuroprotective peptides, viral expression vectors, MANF modulators) can be administered systemically or locally. The route of administration used can depend upon the sensory loss that is being treated or prevented.

In various embodiments, the route of administration can be auricular (otic), buccal, conjunctival, cutaneous, dental, electro-osmosis, endocervical, endosinusial, endotracheal, enteral, epidural, extra-amniotic, extracorporeal, hemodialysis, infiltration, interstitial, intra-abdominal, intra-amniotic, intra-arterial, intra-articular, intrabiliary, intrabronchial, intrabursal, intracardiac, intracartilaginous, intracaudal, intracavernous, intracavitary, intracerebral, intracisternal, intracorneal, intracoronal, dental, intracoronary, intracorporus cavernosum, intradermal, intradiscal, intraductal, intraduodenal, intradural, intraepidermal, intraesophageal, intragastric, intragingival, intraileal, intralesional, intraluminal, intralymphatic, intramedullary, intrameningeal, intramuscular, intraocular, intraovarian, intrapericardial, intraperitoneal, intrapleural, intraprostatic, intrapulmonary, intrasinal, intraspinal, intrasynovial, intratendinous, intratesticular, intrathecal, intrathoracic, intratubular, intratumor, intratympanic, intrauterine, intravascular, intravenous, intravenous bolus, intravenous drip, intraventricular, intravesical, intravitreal, iontophoresis, irrigation, laryngeal, nasal, nasogastric, not applicable, occlusive dressing technique, ophthalmic, oral, oropharyngeal, other, parenteral, percutaneous, periarticular, peridural, perineural, periodontal, rectal, respiratory (inhalation), retrobulbar, soft tissue, subarachnoid, subconjunctival, subcutaneous, sublingual, submucosal, topical, transdermal, transmucosal, transplacental, transtracheal, transtympanicureteral, urethral, vaginal, or by other method or any combination of the forgoing as would be known to one of ordinary skill in the art (see, for example, Remington's Pharmaceutical Sciences, 18th Ed. Mack Printing Company, 1990, incorporated herein by reference).

When the cell death-related sensory loss includes symptoms of visual impairment (e.g., impaired vision, night blindness, retinal detachment, light sensitivity, tunnel vision, loss of peripheral vision, blindness, spots, or a combination thereof), administering the active ingredient(s) to a subject in need thereof can comprise administration to the subject's eye(s). Administration to the eye can be, for example, by conjunctival administration, intracorneal administration, intraocular administration, intravitreal administration, ophthalmic administration, retrobulbar administration, subconjunctival administration, or a combination thereof. These routes of administration are known in the art. In some embodiments, administration is intravitreal administration. In some embodiments, intravitreal administration can be with a syringe.

When the cell death-related sensory loss includes smell loss, administering the active ingredient(s) can be, for example, by endosunusial administration, intrasinal administration, intranasal administration, nasal administration, transmucosal administration, or a combination thereof.

When the cell death-related sensory loss includes taste loss, administering the active ingredients can be by, for example, buccal administration, sublingual administration, oral administration, or a combination thereof.

When the cell death-related sensory loss includes symptoms of peripheral neuropathy, administering the active ingredient(s) can be by, for example, by cutaneous injection, intraepidermal administration, intravenous administration, oral administration, perineural, subcutaneous administration, topical administration, transdermal administration, or a combination thereof.

When the cell death-related sensory loss includes hearing impairment (e.g., hearing loss, tinitis, vertigo, instability or loss of balance, nausea, or a combination thereof) administering the active ingredient(s) to a subject in need thereof can comprise administration to the subject's ear (auricular or otic administration) or inner ear. Administration to the inner ear may be accomplished by various delivery techniques. These include the use of devices to transport and/or deliver the compound in a targeted fashion to the membranes of the round or oval window, where it diffuses into the inner ear or is actively infused. Examples are otowicks (see, e.g., U.S. Pat. No. 6,120,484 to Silverstein), round window catheters (see, e.g., U.S. Pat. Nos. 5,421,818; 5,474,529; 5,476,446; 6,045,528; 6,377,849), or microimplants (see, e.g., WO2004/064912). They further include the use of devices that are inserted into the cochlear duct or any other part of the cochlea (see, e.g., U.S. Pat. No. 6,309,410). Another delivery technique is transtympanic injection (sometimes also called "intratympanic injection"), whereas the medication is injected through the tympanic membrane into the middle ear typically for diffusion across the round window membrane (for a description, see, e.g., Light J. and Silverstein H., Current Opinion in Otolaryngology & Head and Neck Surgery (12): 378-383 (2004). It has been used in clinical practice for a long time and is a relatively minor intervention, which can be carried out in a doctor's office. For repeated injections, a middle ear ventilation tube may be inserted into the tympanic membrane, through which the medication can be administered into the middle ear space. Drug carriers that are too viscous to be injected may also be deposited across a small opening in the tympanic membrane with the aid of surgical instrument.

Formulations and Dosage Forms

The active ingredients can be provided in a pharmaceutical composition. The pharmaceutical composition can comprise pharmaceutically acceptable diluent(s), excipient(s), or carrier(s). The pharmaceutical compositions can include other medicinal or pharmaceutical agents, carriers, adjuvants, such as preserving, stabilizing, wetting or emulsifying agents, solution promoters, salts for regulating the osmotic pressure, and/or buffers.

Methods well known in the art for making formulations are to be found in, for example, Remington: The Science and Practice of Pharmacy, (20th ed.) ed. A. R. Gennaro A R., 2000, Lippencott Williams & Wilkins. Formulations for parenteral administration may, for example, contain as excipients sterile water or saline, polyalkylene glycols such as polyethylene glycol, oils of vegetable origin, or hydrogenated naphthalenes, biocompatible, biodegradable lactide polymer, or polyoxyethylene-polyoxypropylene copolymers may be used to control the release of the present factors. Other potentially useful parenteral delivery systems for the factors include ethylene-vinyl acetate copolymer particles, osmotic pumps, implantable infusion systems, and liposomes. Formulations for inhalation may contain as excipients, for example, lactose, or may be aqueous solutions containing, for example, polyoxyethylene-9-lauryl ether, glycocholate and deoxycholate, or may be oily solutions for administration in the form of nasal drops, or as a gel to be applied intranasally.

The active ingredients (e.g., neuroprotective peptides, viral expression vectors, MANF modulators) can be attached to nanoparticles prior to delivery. The nanoparticles may then be used to deliver the active ingredients, e.g. into the cochlear or vestibular systems.

The concentration of the active ingredient(s) in the formulations can vary depending upon a number of issues, including the dosage to be administered, and the route of administration.

Exemplary Ophthalmic Formulations

For delivery of active ingredients to the eye, the active ingredient(s) can be formulated, for example, in a solution, a suspension, or a controlled-release formulation.

The active ingredient(s) can be formulated in a stable liquid ophthalmic formulation comprising the active ingredient(s), one or more organic co-solvents, one or more tonicity agents, a buffering agent, and optionally a stabilizing agent. The organic co-solvents can comprise for example, polysorbate 20 or polysorbate 80, polyethylene glycol (PEG), for example, PEG 3350, or propylene glycol, or a combination thereof; the tonicity agent can comprise, for example, sodium chloride or potassium chloride; the stabilizing agent can comprise sucrose, sorbitol, glycerol, trehalose, or mannitol; and the buffering agent can comprise, for example, phosphate buffer. (See, e.g., U.S. Pat. No. 8,481,046).

The active ingredients can be formulated in a sustained-release formulation comprising hexPLA. The poly(lactic acid) (PLA) derivative hexylsubstituted poly(lactic acid) (hexPLA; poly(2-hydroxyoctanoic acid)), wherein all methyl groups along the PLA-backbone are substituted by hexyl groups, is a viscous liquid at room-temperature. It can be synthesized by ring-opening polymerization (Trimaille et ah, 2004, Journal of Polymer Science Part A—Polymer Chemistry 42:4379) as well as by a green-chemistry polycondensation (Asmus et ah, 2011, European Journal of Pharmaceutics and Biopharmaceutics 79:584). Preparation of hexPLA is described in the Examples herein. HexPLA is stable under dry heat sterilization conditions and formulations with small, lipophilic molecules released the active compound over several weeks. Prior to formulation, the active ingredient(s) for formulation are preferably lyophilized using well-known techniques in the art.

The sustained release formulation can be prepared by cryo-milling. For example, lyophilized active ingredient (e.g., neuroprotective peptide) and the hexPLA polymer are slowly frozen to −80° C. and milled together in a SPEX 6700 Freezer/Mill (SPEX Industries, Edison, USA) under liquid nitrogen for 5 minutes. This cryo-milling procedure simultaneously reduces the particle size of the solid compound and homogeneously disperses it in the polymer matrix to form a suspension formulation. In certain embodiments, after milling, the formulation is slowly warmed to room temperature under conditions suitable to avoid water condensation on the product (e.g., vacuum, inert gas, or hermetically closed cylinders). (See, e.g., WO2013/113820).

The active ingredients can also be formulated in a sustained release formulation comprising a collagen gelling agent and one or more of a quaternary ammonium preservative, a stabilizing amount of a nonionic ethoxylated alkylphenol surfactant, a chelating agent, a tonicifier, a buffer, and other excipients such as a viscosity agent as well as other stabilizing agents in an aqueous vehicle. The amount of the collagen gelling agent is such that the formulation is a flowable liquid at mammalian eye temperature or less, i.e. at <32° C. and a gelled matrix after being administered to the mammalian eye. The pH and ionic strength can affect the gelling properties of the formulation. (See, e.g., EP 0422681).

Exemplary Inner Ear Formulations

For delivery of active ingredients to the inner ear, the active ingredient(s) can be formulated in a solution, a gel, a foam or fibrin, or other drug carriers can be used. Gels and foams can provide for the controlled release of the active ingredient(s) over an extended period of time such as hours, days or weeks, improve its diffusion into the inner ear by increasing the permeability of the middle-inner ear interface tissue structure or by keeping the formulation in continuous contact with such structure (see, e.g., US2009/0246255,)

The active ingredients can be formulated in a biocompatible polymer. Examples of gel forming biocompatible polymers include, but are not limited to, hyaluronic acid resp. hyaluronates, lecithin gels, (poly)alanine derivatives, pluronics, poly(ethyleneglycol), poloxamers, chitosans, xyloglucans, collagens, fibrins, polyesters, poly(lactides), poly(glycolide) or their copolymers PLGA, sucrose acetate isobutyrate, and glycerol monooleate.

Polymers composed of polyoxypropylene and polyoxyethylene form thermoreversible gels when incorporated into aqueous solutions. These polymers have the ability to change from the liquid state to the gel state at temperatures close to body temperature, therefore allowing useful formulations that are applied to inner ear. The liquid state-to-gel state phase transition can be dependent on the polymer concentration and the ingredients in the solution.

Poloxamer 407 (PF-127) is a nonionic surfactant composed of polyoxyethylene-polyoxypropylene copolymers. Other poloxamers include 188 (F-68 grade), 237 (F-87 grade), 338 (F-108 grade). Aqueous solutions of poloxamers are stable in the presence of acids, alkalis, and metal ions. PF-127 is a commercially available polyoxyethylene-polyoxypropylene triblock copolymer of general formula E106 P70 E106, with an average molar mass of 13,000. The polymer can be further purified by suitable methods that will enhance gelation properties of the polymer. It contains approximately 70% ethylene oxide, which accounts for its hydrophilicity. Concentrated solutions (>20% w/w) of PF-127 copolymer are transformed from low viscosity transparent solutions to solid gels on heating to body temperature.

PF-127 has good solubilizing capacity, low toxicity and is, therefore, considered a good medium for drug delivery systems.

The controlled release formulation can comprise a thermogel, such as a PEG-PLGA-PEG triblock copolymer (Jeong et al, Nature (1997), 388:860-2; Jeong et al, J. Control. Release (2000), 63:155-63; Jeong et al, Adv. Drug Delivery Rev. (2002), 54:37-51). The polymer exhibits sol-gel behavior over a concentration of about 5% w/w to about 40% w/w. Depending on the properties desired, the lactide/glycolide molar ratio in the PLGA copolymer ranges from about 1:1 to about 20:1. The resulting copolymers are soluble in water and form a free-flowing liquid at room temperature, but form a hydrogel at body temperature. A commercially available PEG-PLGA-PEG triblock copolymer is RESOMER RGP t50106 manufactured by Boehringer Ingelheim. This material is composed of a PGLA copolymer of 50:50 poly(DL-lactide-co-glycolide) and is 10% w/w of PEG and has a molecular weight of about 6000.

ReGel® is a tradename of MacroMed Incorporated for a class of low molecular weight, biodegradable block copolymers having reverse thermal gelation properties as described in U.S. Pat. Nos. 6,004,573, 6,117,949, 6,201,072, and 6,287,588. It also includes biodegradable polymeric drug carriers disclosed in pending U.S. patent application Ser. Nos. 09/906,041, 09/559,799 and 10/919,603. The biodegradable drug carrier comprises ABA-type or BAB-type triblock copolymers or mixtures thereof, wherein the A-blocks are relatively hydrophobic and comprise biodegradable polyesters or poly(orthoester)s, and the B-blocks are relatively hydrophilic and comprise polyethylene glycol (PEG), said copolymers having a hydrophobic content of between 50.1 to 83% by weight and a hydrophilic content of between 17 to 49.9% by weight, and an overall block copolymer molecular weight of between 2000 and 8000 Daltons. The drug carriers exhibit water solubility at temperatures below normal mammalian body temperatures and undergo reversible thermal gelation to then exist as a gel at temperatures equal to physiological mammalian body temperatures. The biodegradable, hydrophobic A polymer block comprises a polyester or poly(ortho ester), in which the polyester is synthesized from monomers selected from the group consisting of D,L-lactide, D-lactide, L-lactide, D,L-lactic acid, D-lactic acid, L-lactic acid, glycolide, glycolic acid, ε-caprolactone, ε-hydroxyhexanoic acid, γ-butyrolactone, γ-hydroxybutyric acid, δ-valerolactone, δ-hydroxyvaleric acid, hydroxybutyric acids, malic acid, and copolymers thereof and having an average molecular weight of between about 600 and 3000 Daltons. The hydrophilic B-block segment is preferably polyethylene glycol (PEG) having an average molecular weight of between about 500 and 2200 Daltons.

Additional biodegradable thermoplastic polyesters include AtriGel® (provided by Atrix Laboratories, Inc.) and/or those disclosed, e.g., in U.S. Pat. Nos. 5,324,519; 4,938,763; 5,702,716; 5,744,153; and 5,990,194; wherein the suitable biodegradable thermoplastic polyester is disclosed as a thermoplastic polymer. Examples of suitable biodegradable thermoplastic polyesters include polylactides, polyglycolides, polycaprolactones, copolymers thereof, terpolymers thereof, and any combinations thereof. In some such embodiments, the suitable biodegradable thermoplastic polyester is a polylactide, a polyglycolide, a copolymer thereof, a terpolymer thereof, or a combination thereof. In one embodiment, the biodegradable thermoplastic polyester is 50/50 poly(DL-lactide-co-glycolide) having a carboxy terminal group; is present in about 30 wt. % to about 40 wt. % of the composition; and has an average molecular weight of about 23,000 to about 45,000. Alternatively, in another embodiment, the biodegradable thermoplastic polyester is 75/25 poly (DL-lactide-co-glycolide) without a carboxy terminal group; is present in about 40 wt. % to about 50 wt. % of the composition; and has an average molecular weight of about 15,000 to about 24,000. In further or alternative embodiments, the terminal groups of the poly(DL-lactide-co-glycolide) are either hydroxyl, carboxyl, or ester depending upon the method of polymerization. Polycondensation of lactic or glycolic acid provides a polymer with terminal hydroxyl and carboxyl groups. Ring-opening polymerization of the cyclic lactide or glycolide monomers with water, lactic acid, or glycolic acid provides polymers with the same terminal groups. However, ring-opening of the cyclic monomers with a monofunctional alcohol such as methanol, ethanol, or 1-dodecanol provides a polymer with one hydroxyl group and one ester terminal groups. Ring-opening polymerization of the cyclic monomers with a diol such as 1,6-hexanediol or polyethylene glycol provides a polymer with only hydroxyl terminal groups.

Since the polymer systems of thermoreversible gels dissolve more completely at reduced temperatures, methods of solubilization include adding the required amount of polymer to the amount of water to be used at reduced temperatures. Generally after wetting the polymer by shaking, the mixture is capped and placed in a cold chamber or in a thermostatic container at about 0-10° C. in order to dissolve the polymer. The mixture is stirred or shaken to bring about a more rapid dissolution of the thermoreversible gel polymer. The active ingredient(s) and various additives such as buffers, salts, and preservatives are subsequently added and dissolved. In some instances the active ingredient(s) are suspended if they are insoluble in water. The pH is modulated by the addition of appropriate buffering agents. Round window membrane mucoadhesive characteristics can optionally be imparted to a thermoreversible gel by incorporation of round window membrane muco adhesive carbomers, such as Carbopol® 934P, to the composition (Majithiya et al, AAPS PharmSciTech (2006), 7(3), p. E1; EP0551626).

Exemplary Embodiments

In a first aspect, disclosed herein are methods of treating or preventing cell death-related hearing impairment comprising administering an effective amount of a neuroprotective peptide comprising a mesencephalic astrocyte-derived neurotrophic factor (MANF), or fragment thereof to a subject in need thereof.

In a second aspect, disclosed herein are methods of treating or preventing ototoxicity comprising administering an effective amount of a neuroprotective peptide comprising a mesencephalic astrocyte-derived neurotrophic factor (MANF), or fragment thereof to a subject in need thereof.

In either the first or second aspect, the peptide sequence of the neuroprotective peptide can comprise a sequence that has at least about 80% identity with SEQ ID NO:3. For example, the peptide sequence of the neuroprotective peptide can comprise a sequence that has at least about 90% identity with SEQ ID NO:3. In another example, the peptide sequence of the neuroprotective peptide can comprise a sequence that has at least about 95% identity with SEQ ID NO:3. In another example, the peptide sequence of the neuroprotective peptide can consist of a sequence that has at least about 80% identity with SEQ ID NO:3. In another example, the peptide sequence of the neuroprotective peptide can consist of a sequence that has at least about 90% identity with SEQ ID NO:3. In another example, the peptide sequence of the neuroprotective peptide can consist of a sequence that has at least about 95% identity with SEQ ID NO:3. In another example, the peptide sequence of the neuroprotective peptide can consist of a sequence that has 100% identity with SEQ ID NO:3.

The neuroprotective peptides of the first or second aspect can have a length that is greater than, equal to, or less than the length of SEQ ID NO:3. For example, the neuroprotective peptide can have a length that is at least 80% the length of SEQ ID NO:3. In another example, the neuroprotective peptide can have a length that is 100% the length of SEQ ID NO:3.

In either the first or second aspect, the peptide sequence of the neuroprotective peptide can consist of a sequence listed in Table 3. The neuroprotective peptide can be cell permeable.

In a third aspect, disclosed herein are methods of treating or preventing cell death-related hearing impairment comprising administering an effective amount of a neuroprotective peptide comprising a conserved dopamine neurotrophic factor (CDNF), or a fragment thereof.

In a fourth aspect, disclosed herein are methods of treating or preventing ototoxicity in a subject comprising administering an effective amount of a neuroprotective peptide comprising a conserved dopamine neurotrophic factor (CDNF), or a fragment thereof.

In either the third or fourth aspect, the peptide sequence of the neuroprotective peptide can comprise a sequence that has at least about 80% identity with SEQ ID NO:6. For example, the peptide sequence of the neuroprotective peptide can comprise a sequence that has at least about 90% identity with SEQ ID NO:6. In another example, the peptide sequence of the neuroprotective peptide can comprise a sequence that has at least about 95% identity with SEQ ID NO:6. In another example, the peptide sequence of the neuroprotective peptide can consist of a sequence that has at least about 80% identity with SEQ ID NO:6. In another example, the peptide sequence of the neuroprotective peptide can consist of a sequence that has at least about 90% identity with SEQ ID NO:6. In another example, the peptide sequence of the neuroprotective peptide can consist of a sequence that has at least about 95% identity with SEQ ID NO:6. In another example, the peptide sequence of the neuroprotective peptide can consist of a sequence that is SEQ ID NO:6.

The neuroprotective peptides of the first or second aspect can have a length that is greater than, equal to, or less than the length of SEQ ID NO:6. For example, the neuroprotective peptide can have a length that is at least 80% the length of SEQ ID NO:6. In another example, the neuroprotective peptide can have a length that is 100% the length of SEQ ID NO:6.

In either the third or fourth aspect, the peptide sequence of the neuroprotective peptide can consist of a sequence listed in Table 4. The neuroprotective peptide can be cell permeable.

In any of aspects one through four, the effective amount of the neuroprotective peptide can be in a formulation at a concentration of about 1 µMol-50 µMol. For example, the effective amount of the neuroprotective peptide can be in a formulation at a concentration of about 3 µMol-20 µMol. The effective amount can be administered in a volume of about 100 µL-500 µL of the formulation. For example, the effective amount can be administered in a volume of about 200 µL-300 µL of the formulation.

In any of aspects one through four, the effective amount of the neuroprotective peptide can be about 1 µg-500 µg. For example, the effective amount of the neuroprotective peptide can be about 5 µg-250 µg.

In any of aspects one through four, the subject can suffer from one or more symptoms comprising hearing loss, tinnitus, vertigo, instability or loss of balance, nausea, or a combination thereof. At least one of the symptoms can be improved following treatment.

In any of aspects one through four, the administering can comprise topical administration, systemic administration, intratympanic administration, intracochlear administration, transtympanic injection, or a combination thereof. For example, the administering can comprise intratympanic administration by injection or perfusion. In another example, the administering can comprise intrachochlear administration that is: by injection, with a cochlear implant, with an osmotic mini-pump, or with a reciprocating perfusion system.

In any of aspects one through four, the administering can occur prior to a therapeutic treatment with an ototoxic drug.

In any of aspects one through four, the administering can occur concurrently with a therapeutic treatment with an ototoxic drug.

In any of aspects one through four, the administering can occur after exposure to an ototoxic chemical or toxin.

In any of aspects one through four, the ototoxicity can be associated with an anesthetic, an antibiotic, an antimalarial, a cardiac medication, a chemotherapeutic agent, a diuretic, a glucocorticosteroid, an immunomodulatory drug, a mucosal protectant, a narcotic analgesic, a non-steroidal anti-inflammatory drug (NSAID), a psychopharmacologic agent, a quinine, a toxic substance, a vapor or solvent, or a combination thereof.

In any of aspects one through four, the ototoxicity can be associated with amikacin, amphotericin B, capreomycin, chloramphenicol, erythromycin, gentamycin, kanamycin, minocycline, polymyxin B, neomycin, netilimicin, streptomycin, a sulfonamide, tobramycin, vancomycin, chloroquine, hydroxychloroquine, celiprolol, flecainide, lidocaine, metoprolol, procainamide, propranolo, quinidine, bleomycine, bromocriptine, carboplatinum, cisplatin, methotrexate, nitrogen mustard, vinblastin, vincristine, acetazolamide, bendroflumethiazide, bumetadine, chlorthalidone, diapamide, ethacrynic acid, furosemide, hydrochlorthiazide, methylchlorthiazide, prednisolone, adrenocorticotrophic hormone (ACTH), thalidomide, misoprotol, hydrocodone, aspirin, acematacine, benorilate, benoxaprofen, carprofen, diclofenac, diflunisal, etocolac, fenoprofen, feprazon, ibuprofen, indomethacin, isoxicam, ketoprofen, methyl salicylates, naproxen, D-penicilliamin, phenylbutazone, piroxicam, proglumetacin, proquazon, rofecoxib, salicylates, sulindac, tolmetin, zomepirac, amitryptiline, alprazolam, clorazepate, chlordiazepoxide, diazepam, flurazepam, lorazepam, midazolam, oxazepam, prozepam, quazepam, temazepam, triazolam, bupropion, carbamzepine, diclofensine, doxepin, desiprimine, fluoxetin, imipramine, lithium, melitracen, molindon, paroxetin, phenelzin, protriptilin, trazodon, zimeldin, chloroquine phosphate, quinacrine hydrochloride, quinine sulfate, alcohol, arsenum, caffeine, lead, marijuana, nicotine, mercury, auronofin, cyclohexane, dichloromethane, hexane, lindane, methyl-chloride, methyl-n-butyl-ketone, perchlor-ethylene, styrene, tetrachlor-ethane, toluol, trichloroethylene, or a combination thereof.

In any of aspects one through four, the effective amount of the neuroprotective peptide can be formulated in a solution, a gel, a foam or fibrin.

In a fifth aspect, disclosed herein are methods of improving visual acuity comprising administering to a subject in need thereof an effective amount of a neuroprotective peptide comprising a MANF family protein, or fragment thereof.

In a sixth aspect, disclosed herein are methods of treating a retinal disorder comprising administering to a subject in need thereof an effective amount of a neuroprotective peptide comprising a MANF family protein, or fragment thereof.

In the sixth aspect, the retinal disorder can be macular degeneration, diabetic eye disease, age-related macular degeneration, branch retinal vein occlusion, central retinal vein occlusion, central retinal artery occlusion, central serous retinopathy, diabetic retinopathy, Fuchs' dystrophy, giant cell arteritis, glaucoma, hypertensive retinopathy, thyroid eye disease, iridocorneal endothelial syndrome, ischemic optic neuropathy, juvenile macular degeneration, macular edema, macular telangioctasia, Marfan syndrome, optic neuritis, photokeratitis, retinitis pigmentosa, retinopathy of prematurity, Stargardt disease, usher syndrome, Wolfram syndrome, or any combination thereof. For example, the retinal disorder can be retinitis pigmentosa.

In either the fifth or sixth aspect, the MANF family protein can be MANF.

In either the fifth or sixth aspect, where the MANF family protein is MANF, the peptide sequence of the neuroprotective peptide can comprise a sequence that has at least about 80% identity with SEQ ID NO:3. For example, the peptide sequence of the neuroprotective peptide can comprise a sequence that has at least about 90% identity with SEQ ID NO:3. In another example, the peptide sequence of the neuroprotective peptide can comprise a sequence that has at least about 95% identity with SEQ ID NO:3. In another example, the peptide sequence of the neuroprotective peptide can consist of a sequence that has at least about 80% identity with SEQ ID NO:3. In another example, the peptide sequence of the neuroprotective peptide can consist of a sequence that has at least about 90% identity with SEQ ID NO:3. In another example, the peptide sequence of the neuroprotective peptide can consist of a sequence that has at least about 95% identity with SEQ ID NO:3. In another example, the peptide sequence of the neuroprotective peptide can consist of a sequence that has 100% identity with SEQ ID NO:3.

The neuroprotective peptides of the fifth or sixth aspect, where the MANF family protein is MANF, can have a length that is greater than, equal to, or less than the length of SEQ ID NO:3. For example, the neuroprotective peptide can have a length that is at least 80% the length of SEQ ID NO:3. In another example, the neuroprotective peptide can have a length that is 100% the length of SEQ ID NO:3.

In either the fifth or sixth aspect, where the MANF family protein is MANF, the peptide sequence of the neuroprotective peptide can consist of a sequence listed in Table 3. The neuroprotective peptide can be cell permeable.

In either the fifth or sixth aspect, the MANF family protein can be CDNF.

In either the fifth or sixth aspect, where the MANF family protein is CDNF, the peptide sequence of the neuroprotective peptide can comprise a sequence that has at least about 80% identity with SEQ ID NO:6. For example, the peptide sequence of the neuroprotective peptide can comprise a sequence that has at least about 90% identity with SEQ ID NO:6. In another example, the peptide sequence of the neuroprotective peptide can comprise a sequence that has at least about 95% identity with SEQ ID NO:6. In another example, the peptide sequence of the neuroprotective peptide can consist of a sequence that has at least about 80% identity with SEQ ID NO:6. In another example, the peptide sequence of the neuroprotective peptide can consist of a sequence that has at least about 90% identity with SEQ ID NO:6. In another example, the peptide sequence of the neuroprotective peptide can consist of a sequence that has at least about 95% identity with SEQ ID NO:6. In another example, the peptide sequence of the neuroprotective peptide can consist of a sequence that is SEQ ID NO:6.

The neuroprotective peptides of the fifth or sixth aspect, where the MANF family protein is CDNF, can have a length that is greater than, equal to, or less than the length of SEQ ID NO:6. For example, the neuroprotective peptide can have a length that is at least 80% the length of SEQ ID NO:6. In another example, the neuroprotective peptide can have a length that is 100% the length of SEQ ID NO:6.

In either the fifth or sixth aspect, where the MANF family protein is CDNF, the peptide sequence of the neuroprotective peptide can consist of a sequence listed in Table 4. The neuroprotective peptide can be cell permeable.

In either the fifth or sixth aspect, the administering is topical, intravitreal, intracameral, systemic, conjunctival, intracorneal, intraocular, ophthalmic, retrobulbar, subconjunctival, or a combination thereof.

In a seventh aspect, disclosed herein are methods of treating or preventing cell death-related sensory loss comprising administering to a subject in need thereof an effective amount of a neuroprotective peptide comprising a MANF family protein, or fragment thereof.

In the seventh aspect, the effective amount of the neuroprotective peptide can be in a formulation at a concentration of about 1 µMol-50 µMol. For example, the effective amount of the neuroprotective peptide can be in a formulation at a concentration of about 3 µMol-20 µMol. The effective amount can be administered in a volume of about 100 µL-500 µL of the formulation. For example, the effective amount can be administered in a volume of about 200 µL-300 µL of the formulation.

In the seventh aspect, the effective amount of the neuroprotective peptide can be about 1 µg-500 µg. For example, the effective amount of the neuroprotective peptide can be about 5 µg-250 µg.

In an eighth aspect, disclosed herein are methods of treating or preventing cell death-related sensory loss comprising administering to a subject in need thereof an effective amount of a viral expression vector comprising a promoter sequence capable of directing the expression of an operably linked transgene encoding a neuroprotective peptide comprising a MANF family protein, or fragment thereof.

In either the seventh or eighth aspect, the MANF family protein can be MANF.

In the seventh or eighth aspect, where the MANF family protein is MANF, the peptide sequence of the neuroprotective peptide can comprise a sequence that has at least about 80% identity with SEQ ID NO:3. For example, the peptide sequence of the neuroprotective peptide can comprise a sequence that has at least about 90% identity with SEQ ID NO:3. In another example, the peptide sequence of the neuroprotective peptide can comprise a sequence that has at least about 95% identity with SEQ ID NO:3. In another example, the peptide sequence of the neuroprotective peptide can consist of a sequence that has at least about 80% identity with SEQ ID NO:3. In another example, the peptide sequence of the neuroprotective peptide can consist of a sequence that has at least about 90% identity with SEQ ID NO:3. In another example, the peptide sequence of the neuroprotective peptide can consist of a sequence that has at least about 95% identity with SEQ ID NO:3. In another example, the peptide sequence of the neuroprotective peptide can consist of a sequence that has 100% identity with SEQ ID NO:3.

In the seventh or eighth aspect, where the MANF family protein is MANF, the neuroprotective peptide can have a length that is greater than, equal to, or less than the length of SEQ ID NO:3. For example, the neuroprotective peptide can have a length that is at least 80% the length of SEQ ID NO:3. In another example, the neuroprotective peptide can have a length that is 100% the length of SEQ ID NO:3.

In the seventh or eighth aspect, where the MANF family protein is MANF, the peptide sequence of the neuroprotective peptide can consist of a sequence listed in Table 3. The neuroprotective peptide can be cell permeable.

In the eighth aspect, where the MANF family protein is MANF, the transgene can comprise a nucleotide sequence that has at least about 80% identity with SEQ ID NO:184. For example, the transgene can comprise a nucleotide sequence that has at least about 90% identity with SEQ ID NO:184. In another example, the transgene can comprise a nucleotide sequence that has at least about 95% identity with SEQ ID NO:184.

In the eighth aspect, where the MANF family protein is MANF, the transgene can comprise a nucleotide sequence that has at least about 80% identity with SEQ ID NO:185. For example, the transgene can comprise a nucleotide sequence that has at least about 90% identity with SEQ ID NO:185. In another example, the transgene can comprise a nucleotide sequence that has at least about 95% identity with SEQ ID NO:185.

In either the seventh or eighth aspect, the MANF family protein can be CDNF.

In the seventh or eighth aspect, where the MANF family protein is CDNF, the peptide sequence of the neuroprotective peptide can comprise a sequence that has at least about 80% identity with SEQ ID NO:6. For example, the peptide sequence of the neuroprotective peptide can comprise a sequence that has at least about 90% identity with SEQ ID NO:6. In another example, the peptide sequence of the neuroprotective peptide can comprise a sequence that has at least about 95% identity with SEQ ID NO:6. In another example, the peptide sequence of the neuroprotective peptide can consist of a sequence that has at least about 80% identity with SEQ ID NO:6. In another example, the peptide sequence of the neuroprotective peptide can consist of a sequence that has at least about 90% identity with SEQ ID NO:6. In another example, the peptide sequence of the neuroprotective peptide can consist of a sequence that has at least about 95% identity with SEQ ID NO:6. In another example, the peptide sequence of the neuroprotective peptide can consist of a sequence that is SEQ ID NO:6.

In the seventh or eighth aspect, where the MANF family protein is CDNF, the neuroprotective peptide can have a length that is greater than, equal to, or less than the length of SEQ ID NO:6. For example, the neuroprotective peptide can have a length that is at least 80% the length of SEQ ID NO:6. In another example, the neuroprotective peptide can have a length that is 100% the length of SEQ ID NO:6.

In the seventh or eighth aspect, where the MANF family protein is CDNF, the peptide sequence of the neuroprotective peptide can consist of a sequence listed in Table 4. The neuroprotective peptide can be cell permeable.

In the eighth aspect, where the MANF family protein is CDNF, the transgene can comprise a nucleotide sequence that has at least about 80% identity with SEQ ID NO:186. For example, the transgene can comprise a nucleotide sequence that has at least about 90% identity with SEQ ID NO:186. In another example, the transgene can comprise a nucleotide sequence that has at least about 95% identity with SEQ ID NO:186.

In the eighth aspect, where the MANF family protein is CDNF, the transgene can comprise a nucleotide sequence that has at least about 80% identity with SEQ ID NO:187. For example, the transgene can comprise a nucleotide sequence that has at least about 90% identity with SEQ ID NO:187. In another example, the transgene can comprise a nucleotide sequence that has at least about 95% identity with SEQ ID NO:187.

In the eighth aspect, the viral expression vector can be HIV, SIV, FIV, EIAV, AAV, adenovirus, retrovirus, herpes virus, lentivirus, or a replication defective version thereof.

In a ninth aspect, disclosed herein are methods of treating or preventing cell death-related sensory loss in a subject in need thereof, the method comprising administering an effective amount of a MANF modulator. The MANF modulator can be valproic acid.

In any of the seventh, eighth, or ninth aspects, the cell death-related sensory loss can be impaired vision, night blindness, retinal detachment, light sensitivity, tunnel vision, loss of peripheral vision, blindness, spots, or a combination thereof. The cell death-related sensory loss can be caused by macular degeneration, diabetic eye disease, age-related macular degeneration, branch retinal vein occlusion, central retinal vein occlusion, central retinal artery occlusion, central serous retinopathy, diabetic retinopathy, Fuchs' dystrophy, giant cell arteritis, glaucoma, hypertensive retinopathy, thyroid eye disease, iridocorneal endothelial syndrome, ischemic optic neuropathy, juvenile macular degeneration, macular edema, macular telangioctasia, marfan syndrome, optic neuritis, photokeratitis, retinitis pigmentosa, retinopathy of prematurity, stargardt disease, usher syndrome, Wolfram syndrome, or any combination thereof. The administering can be topical, intravitreal, intracameral, systemic, conjunctival, intracorneal, intraocular, ophthalmic, retrobulbar, subconjunctival, or a combination thereof.

In any of the seventh, eighth, or ninth aspects, the cell death-related sensory loss can be a loss or decrease of the ability to smell. The cell death-related sensory loss can be caused by age, trauma, disease, or a combination thereof. Administering can comprise endosunusial administration, intrasinal administration, intranasal administration, nasal administration, transmucosal administration, or a combination thereof.

In any of the seventh, eighth, or ninth aspects, the cell death-related sensory loss can be a loss or decrease of the ability to taste. The cell death-related sensory loss can be caused by zinc deficiency or zinc toxicity, age, drug or toxin exposure, or a combination thereof. Administering can comprise buccal administration, sublingual administration, oral administration, endosunusial administration, intrasinal administration, intranasal administration, nasal administration, transmucosal administration, or a combination thereof.

In any of the seventh, eighth, or ninth aspects, the cell death-related sensory loss can be reduced sensitivity to temperature change and pain, spontaneous tingling or burning pain, skin allodynia (severe pain from normally nonpainful stimuli, such as light touch), or a combination thereof. The cell death-related sensory loss can be caused by chemotherapy-linked neuropathy or diabetic neuropathy. Administering can comprise cutaneous injection, intraepidermal administration, intravenous administration, oral administration, perineural, subcutaneous administration, topical administration, transdermal administration, or a combination thereof.

In any of the seventh, eighth, or ninth aspects, the cell death-related sensory loss can be hearing loss, tinnitus, vertigo, instability or loss of balance, nausea, or a combination thereof. The cell death-related sensory loss can be age-related hearing loss. The cell death-related sensory loss can be noise-induced hearing loss. The cell death-related sensory loss can be caused by an ototoxic chemical. The cell death-related sensory loss can be caused by drug-induced ototoxicity. Administering can comprise topical administration, systemic administration, intratympanic administration, intracochlear administration, transtympanic injection, or a combination thereof.

In a tenth aspect, disclosed herein are methods of treating or preventing ototoxicity comprising administering to a subject in need thereof an effective amount of a viral expression vector comprising a promoter sequence capable of directing the expression of an operably linked transgene encoding a neuroprotective peptide comprising a MANF family protein, or fragment thereof.

In the tenth aspect, the MANF family protein can be MANF.

In the tenth aspect, where the MANF protein is MANF, the peptide sequence of the neuroprotective peptide can comprise a sequence that has at least about 80% identity with SEQ ID NO:3. For example, the peptide sequence of the neuroprotective peptide can comprise a sequence that has at least about 90% identity with SEQ ID NO:3. In another example, the peptide sequence of the neuroprotective peptide can comprise a sequence that has at least about 95% identity with SEQ ID NO:3. In another example, the peptide sequence of the neuroprotective peptide can consist of a sequence that has at least about 80% identity with SEQ ID NO:3. In another example, the peptide sequence of the neuroprotective peptide can consist of a sequence that has at least about 90% identity with SEQ ID NO:3. In another example, the peptide sequence of the neuroprotective peptide can consist of a sequence that has at least about 95% identity with SEQ ID NO:3. In another example, the peptide sequence of the neuroprotective peptide can consist of a sequence that has 100% identity with SEQ ID NO:3.

In the tenth aspect, where the MANF family protein is MANF, the neuroprotective peptide can have a length that is greater than, equal to, or less than the length of SEQ ID NO:3. For example, the neuroprotective peptide can have a length that is at least 80% the length of SEQ ID NO:3. In another example, the neuroprotective peptide can have a length that is 100% the length of SEQ ID NO:3.

In the tenth aspect, where the MANF family protein is MANF, the peptide sequence of the neuroprotective peptide can consist of a sequence listed in Table 3. The neuroprotective peptide can be cell permeable.

In the tenth aspect, where the MANF family protein is MANF, the transgene can comprise a nucleotide sequence that has at least about 80% identity with SEQ ID NO:184. For example, the transgene can comprise a nucleotide sequence that has at least about 90% identity with SEQ ID NO:184. In another example, the transgene can comprise a nucleotide sequence that has at least about 95% identity with SEQ ID NO:184.

In the tenth aspect, where the MANF family protein is MANF, the transgene can comprise a nucleotide sequence that has at least about 80% identity with SEQ ID NO:185. For example, the transgene can comprise a nucleotide sequence that has at least about 90% identity with SEQ ID NO:185. In another example, the transgene can comprise a nucleotide sequence that has at least about 95% identity with SEQ ID NO:185.

In the tenth aspect, the MANF family protein can be CDNF.

In the tenth aspect, where the MANF family protein is CDNF, the peptide sequence of the neuroprotective peptide can comprise a sequence that has at least about 80% identity with SEQ ID NO:6. For example, the peptide sequence of the neuroprotective peptide can comprise a sequence that has at least about 90% identity with SEQ ID NO:6. In another example, the peptide sequence of the neuroprotective peptide can comprise a sequence that has at least about 95% identity with SEQ ID NO:6. In another example, the peptide sequence of the neuroprotective peptide can consist of a sequence that has at least about 80% identity with SEQ ID NO:6. In another example, the peptide sequence of the neuroprotective peptide can consist of a sequence that has at least about 90% identity with SEQ ID NO:6. In another example, the peptide sequence of the neuroprotective peptide can consist of a sequence that has at least about 95% identity with SEQ ID NO:6. In another example, the peptide sequence of the neuroprotective peptide can consist of a sequence that is SEQ ID NO:6.

In the tenth aspect, where the MANF family protein is CDNF, the neuroprotective peptide can have a length that is greater than, equal to, or less than the length of SEQ ID NO:6. For example, the neuroprotective peptide can have a length that is at least 80% the length of SEQ ID NO:6. In another example, the neuroprotective peptide can have a length that is 100% the length of SEQ ID NO:6.

In the tenth aspect, where the MANF family protein is CDNF, the peptide sequence of the neuroprotective peptide can consist of a sequence listed in Table 4. The neuroprotective peptide can be cell permeable.

In the tenth aspect, where the MANF family protein is CDNF, the transgene can comprise a nucleotide sequence that has at least about 80% identity with SEQ ID NO:186. For example, the transgene can comprise a nucleotide sequence that has at least about 90% identity with SEQ ID NO:186. In another example, the transgene can comprise a nucleotide sequence that has at least about 95% identity with SEQ ID NO:186.

In the tenth aspect, where the MANF family protein is CDNF, the transgene can comprise a nucleotide sequence that has at least about 80% identity with SEQ ID NO:187. For example, the transgene can comprise a nucleotide sequence that has at least about 90% identity with SEQ ID NO:187. In another example, the transgene can comprise a nucleotide sequence that has at least about 95% identity with SEQ ID NO:187.

In the tenth aspect, the viral expression vector can be HIV, SIV, FIV, EIAV, AAV, adenovirus, retrovirus, herpes virus, lentivirus, or a replication defective version thereof.

In an eleventh aspect, disclosed herein are methods of treating or preventing ototoxicity comprising administering to a subject in need thereof an effective amount of a MANF modulator. The MANF modulator can be valproic acid.

In the tenth or eleventh aspect, administering can occur prior to a therapeutic treatment with a drug.

In the tenth or eleventh aspect, administering can comprise topical administration, systemic administration, intratympanic administration, intracochlear administration, transtympanic injection, or a combination thereof. For example, administering can comprise intratympanic administration by injection or perfusion. In another example, administering can comprise intrachochlear administration that is: by injection, with a cochlear implant, with an osmotic mini-pump, or with a reciprocating perfusion system.

In the tenth or eleventh aspect, administering can occur prior to a therapeutic treatment with a drug.

In the tenth or eleventh aspect, administering can occur after beginning a therapeutic treatment with a drug.

In the tenth or eleventh aspect, administering can occur after the subject in need thereof has experienced symptoms of drug-induced ototoxicity.

In the tenth or eleventh aspect, administering can occur before an anticipated exposure, during an exposure, or after an exposure to an ototoxic chemical or toxin.

In the tenth or eleventh aspect, the subject in need thereof can have symptoms of ototoxicity comprising hearing loss, tinnitus, vertigo, instability or loss of balance, nausea, or a combination thereof.

In the tenth or eleventh aspect, the ototoxicity can be caused by an anesthetic, an antibiotic, an antimalarial, a cardiac medication, a chemotherapeutic agent, a diuretic, a glucocorticosteroid, an immunomodulatory drug, a mucosal protectant, a narcotic analgesic, a non-steroidal anti-inflammatory drug (NSAID), a psychopharmacologic agent, a quinine, a toxic substance, a vapor or solvent, or a combination thereof.

In the tenth or eleventh aspect, the ototoxicity can be caused by amikacin, amphotericin B, capreomycin, chloramphenicol, erythromycin, gentamycin, kanamycin, minocycline, polymyxin B, neomycin, netilimicin, streptomycin, a sulfonamide, tobramycin, vancomycin, chloroquine, hydroxychloroquine, celiprolol, flecainide, lidocaine, metoprolol, procainamide, propranolo, quinidine, bleomycine, bromocriptine, carboplatinum, cisplatin, methotrexate, nitrogen mustard, vinblastin, vincristine, acetazolamide, bendroflumethiazide, bumetadine, chlorthalidone, diapamide, ethacrynic acid, furosemide, hydrochlorthiazide, methylchlorthiazide, prednisolone, adrenocorticotrophic hormone (ACTH), thalidomide, misoprotol, hydrocodone, aspirin, acematacine, benorilate, benoxaprofen, carprofen, diclofenac, diflunisal, etocolac, fenoprofen, feprazon, ibuprofen, indomethacin, isoxicam, ketoprofen, methyl salicylates, naproxen, D-Penicilliamin, phenylbutazone, piroxicam, proglumetacin, proquazon, rofecoxib, salicylates, sulindac, tolmetin, zomepirac, amitryptiline, alprazolam, clorazepate, chlordiazepoxide, diazepam, flurazepam, lorazepam, midazolam, oxazepam, prozepam, quazepam, temazepam, triazolam, bupropion, carbamzepine, diclofensine, doxepin, desiprimine, fluoxetin, imipramine, lithium, melitracen, molindon, paroxetin, phenelzin, protriptilin, trazodon, zimeldin, chloroquine phosphate, quinacrine hydrochloride, quinine sulfate, alcohol, arsenum, caffeine, lead, marijuana, nicotine, mercury, auronofin, cyclohexane, dichloromethane, hexane, lindane, methyl-chloride, methyl-n-butyl-ketone, perchlor-ethylene, styrene, tetrachlor-ethane, toluol, trichloroethylene, or a combination thereof.

EXAMPLES

Example 1: MANF Protects Hair Cells in an In Vitro Assay of Hair Cell Survival

This example demonstrates the ability of MANF to protect hair cells in the cochlea from ototoxic stimuli in an in vitro cochlea organ culture.

Briefly, on the first day, the middle part of the cochlea is dissected out from p5 rat pups. The cochlea are placed on coverslips coated with poly-ornithine and laminin and cultured in p35 dishes with 2 mL of cochlea culture media.

Three conditions are performed: an untreated control, a treatment with G418 only, and a treatment with MANF and G418. On the second day, in the experimental condition, the cultured cochlea are treated with 100 ng/mL of MANF. On the third day, the appropriate cultured cochlea are treated with 1 μg G418. On the fourth day, Live/Dead cell viability reagents are added to all of the cultured cochlea according to the manufacturer's protocol, and the cultured cochlea are imaged on a fluorescence dissecting microscope. Exemplary images are shown in FIG. 1.

In control cultures (top row, FIG. 1), the majority of the cells are alive at 4 days in culture, as demonstrated by the middle panel, top row. Some cell death is demonstrated by the presence of fluorescence in the outer hair cell population, as demonstrated by the small red fluorescent dots (dead cells) in the right panel, top row. Treatment with Geneticin (G418) leads to elevated levels of cell death (middle row, FIG. 1). The orientation of the cochlea also allows visualization of both the inner hair cells and the spiral ganglia—the cells that are internal to the outer hair cell layer. Pre-treatment with MANF reduces the number of dead cells (bottom row, FIG. 1). There are some clumps of unidentified cells that contain both live and dead cells that are laying on top of the outer hair cells.

The method of cochlear isolation can damage the ends, leading to focal cell death at the ends of the tissue. Nevertheless, cell death is increased in response to G418, a result that is not seen in the MANF pre-treated culture.

Example 2: Dose-Dependent Evaluation of Mesencephalic Astrocyte-Derived Neurotrophic Factor (MANF) to Prevent Visual Acuity Loss and Photoreceptor Cell Loss in Rd10/Rd10 Mice Objective:

To determine the efficacy of Mesencephalic Astrocyte-derived Neurotrophic Factor (MANF) to prevent loss of visual acuity and photoreceptor cells following intravitreal delivery to rd10/rd10 mice, a mouse model of retinitis pigmentosa.

Materials and Methods:

Test Compound and Vehicle:

The test compound is prepared from a stock solution of rhMANF (3 mg/mL). The vehicle is PBS pH 7.4.

Recombinant human mesencephalic astrocyte-derived neurotrophic factor (rhMANF) is used. rhMANF is expressed in a Chinese hamster ovary (CHO)-based cell line using QMCF technology and purified by ion-exchange and gel-filtration chromatography from serum-free CHO growth medium. The rhMANF is homogenous, as determined by mass-spectroscopy and displayed a molecular weight of 18142.3 Da. Coomassie-stained SDS-PAGE and Western blotting results in a single band of the expected molecular weight. The endotoxin level is less than 1 EU/mg of protein as determined by the LAL method.

rhMANF displays cellular activity on dopaminergic neurons in the expected concentration range and is active in vivo in a mouse model of retinal degeneration.

rhMANF is provided as a 3 mg/ml solution in PBS, pH 7.4.

rhMANF is shipped on dry-ice and is stored at −70 degrees Celsius upon receipt. Repeated freeze-thaw cycles are avoided and therefore the rhMANF solution is aliquoted into smaller quantities.

Animals:

A mouse model of retinitis pigmentosa is used in these experiments. Pde6b$^{rd10}$ (rd10) is a spontaneous missense point mutation in Pde6b (cGMP phosphodiesterase 6B, rod receptor, beta polypeptide). Mice homozygous for the rd10 mutation show histological changes at postnatal day 16 (P16) of age and sclerotic retinal vessels at four weeks of age, consistent with retinal degeneration. Retinal sections have been shown to be highly positive for TUNEL and activated caspase-3 immunoreactivity, specifically in the outer nuclear layer (ONL). ERGs of these mice are typically never normal, but rod and cone ERG a- and b-waves can be measured at P18 with a steady decline by over 90% by two months of age. Rearing mice homozygous rd10 in total darkness typically delays degeneration for at least a week, after which morphological and functional loss typically progresses irregularly. (See, e.g., Chang et al. (2007) Vision Res. 47 (5) 624-33.)

All rd10/rd10 mice will be housed in groups of 3-5 in large cages kept in ventilated shelves under standard animal care conditions. Animals will receive an ear tag with a 4 digit ID number for tracking and all animal information will be stored in a local MS Access database.

Animals (rd10/rd10 mice) will be dark-reared from birth. On P31, the pups will be transferred to housing in a normal cyclic light environment. Briefly, Rd10/rd10 pregnant dams will be house in darkness upon observation of a mucus plug. Newborn pups will be housed with mothers in complete darkness from postnatal day 1 through postnatal day 30. On postnatal day 31, animals will be transitioned to maintenance under normal cyclical light conditions consisting of 12 hours of light (<500 lux) followed by 12 hours of darkness.

Also on P31, bilateral intravitreal dosing of vehicle or test agent (1 µL volume) will be performed. On P38 and P45, OKT analyses (see below) will be performed to quantify spatial frequency threshold. On P46, enucleation of eyes and fixation in 4% paraformaldehyde for quantification of retinal thickness will be performed. Animals showing hemorrhage following intravitreal injection will be excluded from the analysis. This plan is summarized in Table 7. Six (6) animals will be used in each study arm.

TABLE 7

Arm Allocation

| Arm | Model | Treatment | Treatment Details | Assessment |
|---|---|---|---|---|
| 1 | rd10 | PBS, pH 7.4 (n = 6) | Bilateral intravitreal injection on P31 | OKT analyses at P38 and P45; Enucleation of eyes at P46 for histological quantification of retinal thickness |
| 2 | rd10 | MANF 2.0 µg/eye (n = 6) | Bilateral intravitreal injection on P31 | OKT analyses at P38 and P45; Enucleation of eyes at P46 for histological quantification of retinal thickness |
| 3 | rd10 | MANF 1.0 µg/eye (n = 6) | Bilateral intravitreal injection on P31 | OKT analyses at P38 and P45; Enucleation of eyes at P46 for histological quantification of retinal thickness |
| 4 | rd10 | MANF 0.33 µg/eye (n = 6) | Bilateral intravitreal injection on P31 | OKT analyses at P38 and P45; Enucleation of eyes at P46 for histological quantification of retinal thickness |

Optokinetic Tracking (OKT):

All optokinetic tracking experiments are performed using an OptoMotry designed for rodent use (Cerebral Mechanics Inc.). In this non-invasive assessment, mice are placed onto a platform surrounded by 4 LCD screens which reside within a light-protected box. Visual stimuli are then presented to the mice via the LCD screens and a masked observer visualizes and scores optokinetic tracking reflexes from a digital camcorder which is mounted on the top of the box. For measurements of spatial frequency threshold, the mice will be tested at a range of spatial frequencies from 0.034 to 0.664 cycles/degree. The OptoMotry device employs an algorithm to accept the input from the masked observer and automatically adjust the testing stimuli based upon whether the animal exhibited the correct or incorrect tracking reflex.

Tissue Collection:

Following sedation with ketamine/xylazine, animals are euthanized with a lethal dose of pentobarbital. The right eye of all animals will be scorched with a flamed needle to demarcate the superior portion of the eye, enucleated, fixed in 4% paraformaldehyde and processed for H&E (Hematoxylin and eosin) histology.

Quantification of Retinal Thickness

Paraffin sections will be obtained through the central retina along the vertical meridian, as identified by demarcation prior to enucleation. Following H&E staining, microscopy will be used to visualize the sections. Digital images are captured and Spot Advanced software (Spot Imaging Solutions) is used to quantify the thickness of the outer nuclear layer at 200 µm intervals from superior retina to the inferior retina.

Data and Statistical Analyses

Statistical significance is determined using Prism software (Graphpad Inc.) to perform t-test or one-way Analysis of Variance (ANOVA) calculations, and a threshold of $p<0.05$ is set to determine whether any changes are statistically significant.

Results:

Spatial Frequency Threshold—Optokinetic Tracking Experiment

Figure 2:
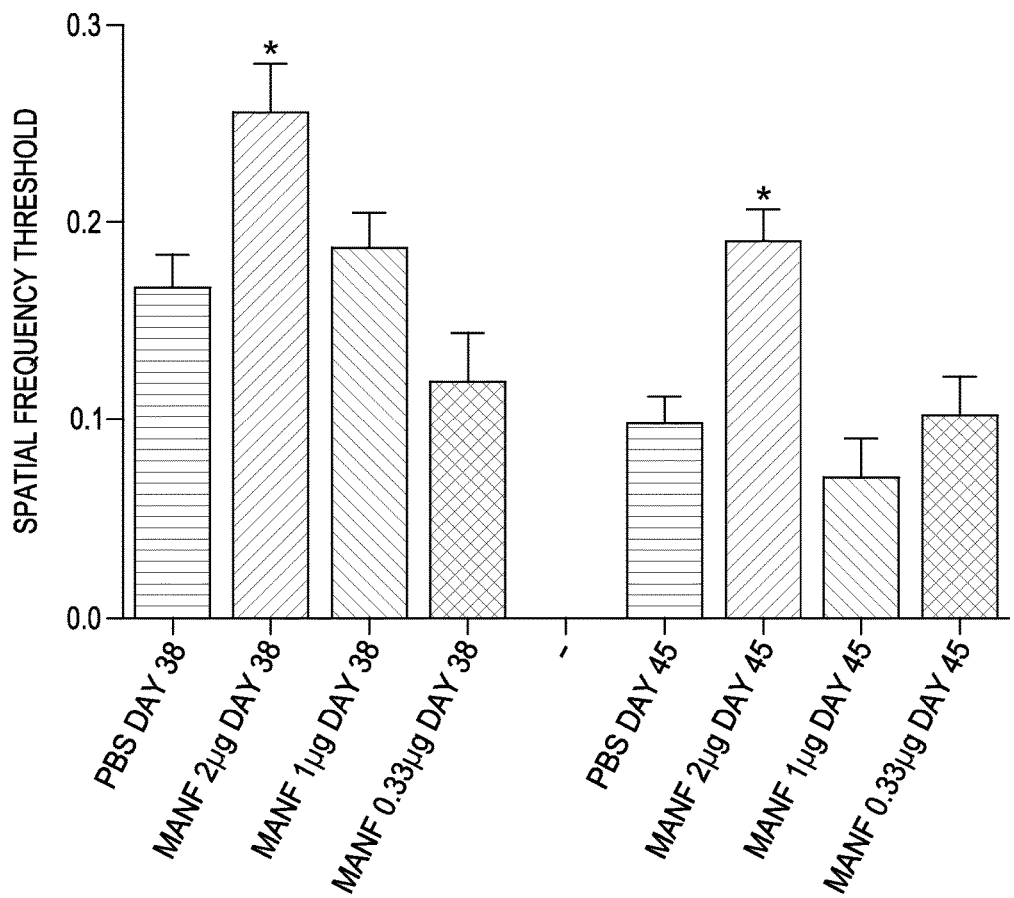
FIG. 2 illustrates spatial frequency thresholds measured in mice homozygous for the rd10 mutation and treated with either rhMANF or PBS (vehicle control).

The results of the OKT analysis are shown in FIG. 2. At both day 38 and day 45, the spatial frequency thresholds (cycles/degree) for mice treated with 2 µg of rhMANF were higher than those of mice treated with the vehicle (PBS) with a statistical significance of less than 0.05 as determined by 1-way ANOVA, Dunn's post test. These data indicate that treatment with 2 µg rhMANF was effective in improving visual acuity in a mouse model of retinitis pigmentosa.

Example 3: Effects of MANF on Cochlear Hair Cell Survival

Background

MANF is well established as a neurotrophic factor that can rescue certain neurons from cell death induced by a variety of insults. This example tests the hypothesis that MANF could protect cochlear hair cells from cell death induced by antibiotics and other ototoxic insults. The results show that MANF can protect ganglion cells and hair cells from antibiotic-associated ototoxicity.

Experimental Design

Cochleae from P0-P3 rat pups are isolated and then cultured in vitro in the presence or absence of G418 (Geneticin), an ototoxic aminoglycoside antibiotic. Some cochleae are pre-treated with varying levels of MANF to assess protection. Following treatment, cultures are stained with different vital dyes to determine the anatomy and viability of the cells. The Live/Dead reagent (Molecular Probes) is used to label living cells green with calcien-AM and dead cells red with ethidium bromide heterodimer. A separate fluorescent reagent, FM1-43, is used to label functional hair cells, because it selectively enters the mechanosensory channel on functioning hair cells. Confocal microscopy is used to image the cells.

All animal housing and procedures followed IACUC approved animal care and welfare policies. SAS SD rat pups (Charles River Laboratories International, Inc.) were sacrificed via decapitation at age P0-P3. Inner ear otic capsules were dissected in ice cold PBS. The Organ of Corti was carefully separated from the immature bone of each otic capsule and mounted on poly-D-lysine coated glass coverslips that had also been treated with Cell-Tak. Coverslips were then transferred to 3.5 cm tissue culture dish in 2 ml medium volume of medium. Culture dishes were placed in a humidified incubator with 5% CO2, at 37° C.

Figure 3:
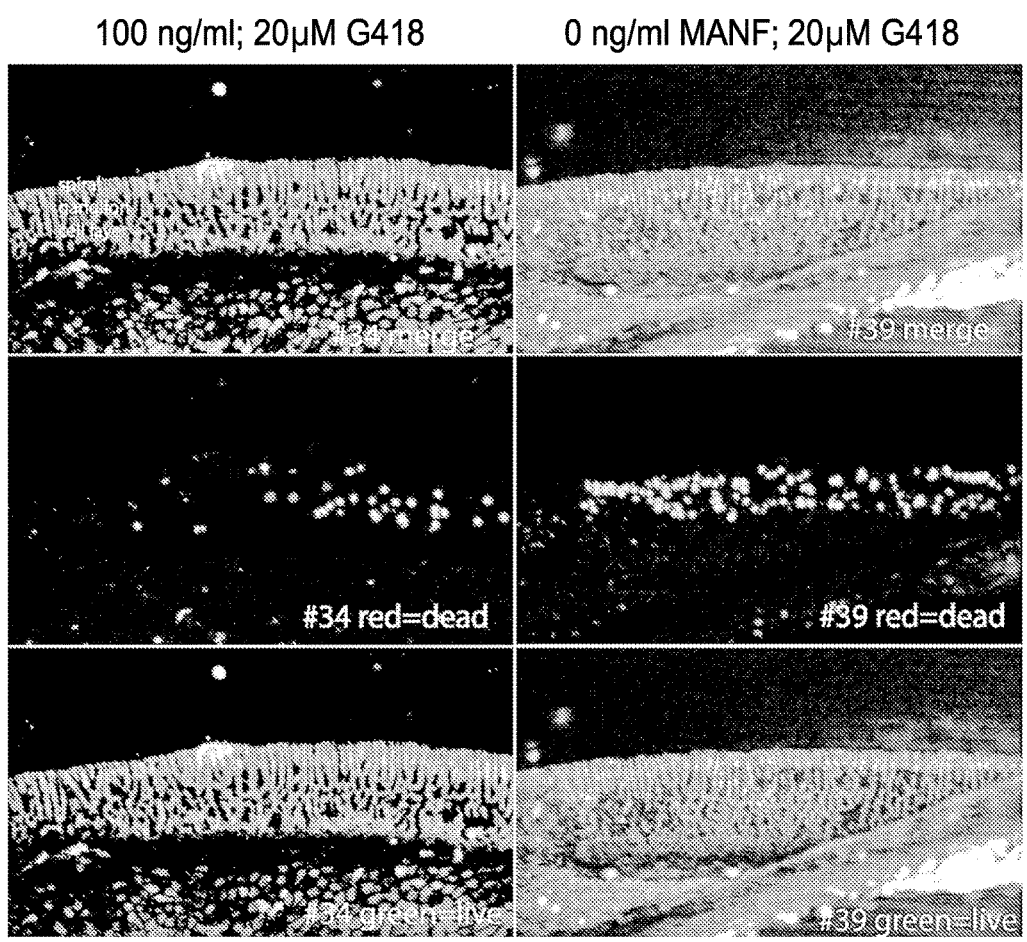
FIG. 3 illustrates the results of an in vitro assay for ganglion cell survival in cochlea cultured 20 μM G418, with (left column) or without (right column) pretreatment with 100 ng/mL MANF, and stained with LIVE/DEAD; the middle row shows dead cells within the spiral ganglion cell layer, the bottom row shows live cells, and the top row is a merged image.
Figure 4:
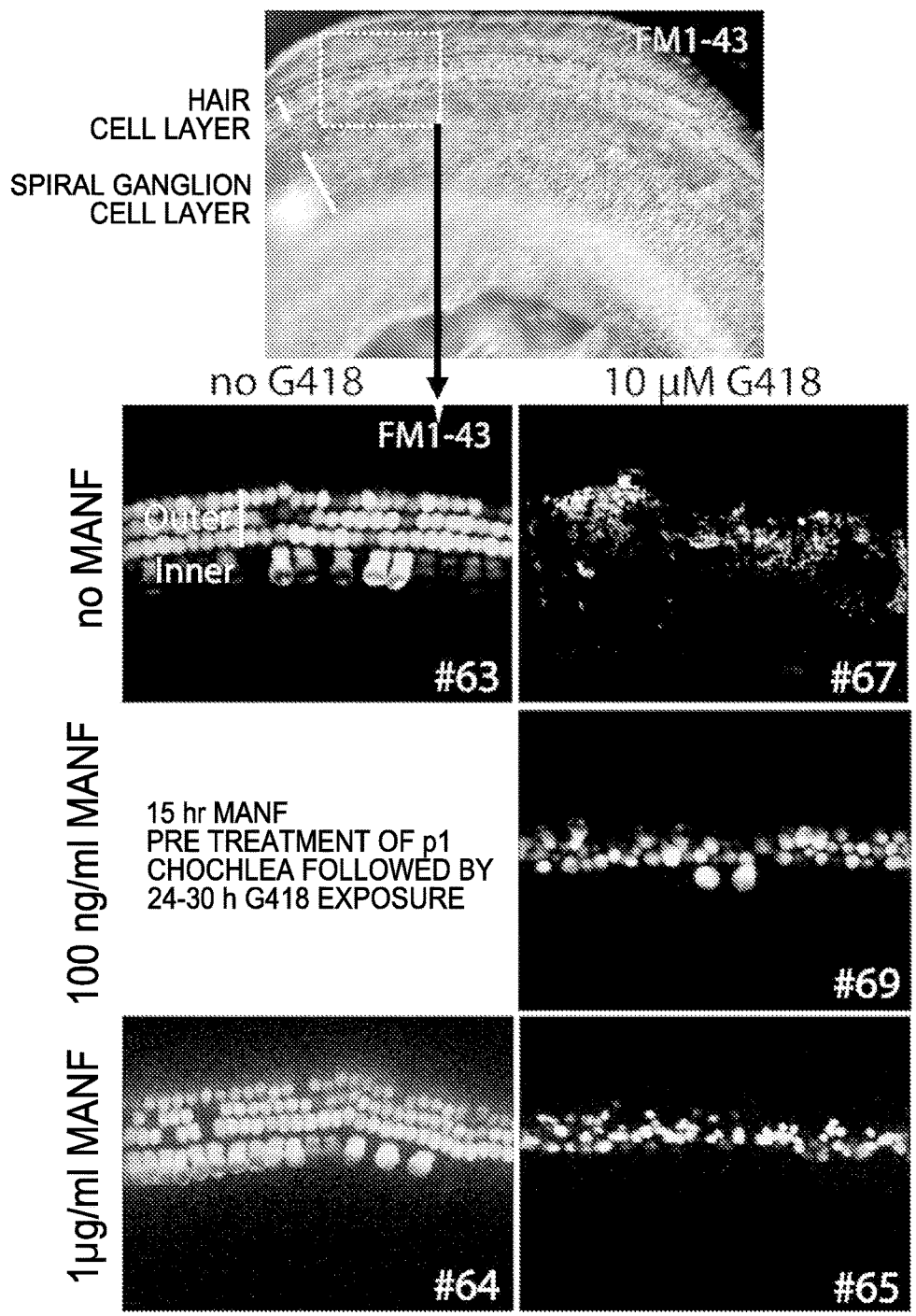
FIG. 4 illustrates the results of an in vitro assay for hair cell survival; the top image shows a broad view of the Organ of Corti with the hair cell and spiral ganglion cell layers labeled; the bottom images are higher magnification views of the hair cell layer from cochlea cultured with (left column) or without (right column) 10 μM G418 and stained with vital dye FM1-43 to label hair cells; the cochlea were pre-treated with either no MANF (top row), 100 ng/mL MANF (middle row), or 1 μg/mL MANF (bottom row).

The cochleae are cultured under two different conditions. Some cochleae, such as those shown in FIG. 3, are cultured in DMEM medium supplemented with 10% fetal bovine serum (FBS), 50 I.U./mL penicillin, and 50 µg/mL streptomycin. Other cochleae, such as those shown in FIG. 4, are cultured in DMEM/F-12 medium supplemented with 10% FBS and 5 µg/mL ampicillin. It is notable that the pen/strep combination can be ototoxic independent of the G418 antibiotic.

Results

The data show that pretreatment of cochleae with MANF can protect ganglion cells (FIG. 3) and hair cells (FIG. 4) from ototoxic cell death due to exposure to G418.

FIG. 3 illustrates that MANF can protect ganglion cells deep within the cochlea from antibiotic-associated ototoxicity. The middle row of images shows that pretreatment with 100 ng/mL MANF reduced the number of dead cells in the spiral ganglion cell layer of the cochlea following exposure to 20 µM G418. The bottom row of images shows live cells; the top row of images shows an overlay of live and dead cells.

FIG. 4 illustrates that MANF can protect hair cells of the cochlea from antibiotic-associated ototoxicity. The top image shows a broad view of the Organ of Corti (a region of the cochlea) with the hair cell layer and spiral ganglion cell layer labelled. The bottom images are higher magnification images focused on the hair cell layer. In the absence of G418, the hair cell layer shows a characteristic four layers of hair cells (top left), the structure of which does not appear to be adversely affected by treatment with 1 µg/mL MANF (bottom left). The top right image shows that treatment of the cochleae with 10 µM G418 for 24-30 hours almost completely destroys this hair cell layer. Pretreatment for 15 hours with either 100 ng/mL MANF (middle right) or 1 µg/mL MANF (bottom right) prevents much of the ototoxic cell loss in the hair cell layer.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of treating ototoxicity comprising administering an effective amount of a neuroprotective peptide comprising a mesencephalic astrocyte-derived neurotrophic factor (MANF) to a subject in need thereof, wherein said neuroprotective peptide comprises SEQ ID NO:3.

2. The method of claim 1, wherein the neuroprotective peptide is cell permeable.

3. The method of claim 1, wherein the subject suffers from one or more symptoms comprising hearing loss, tinnitus, vertigo, instability or loss of balance, nausea, or a combination thereof.

4. The method of claim 1, wherein administering comprises topical administration, systemic administration, intratympanic administration, intracochlear administration, transtympanic injection, or a combination thereof.

5. The method of claim 1, wherein the administering comprises intratympanic administration by injection or perfusion.

6. The method of claim 1, wherein the administering comprises intracochlear administration that is: by injection, with a cochlear implant, with an osmotic mini-pump, or with a reciprocating perfusion system.

7. The method of claim 1, wherein the ototoxicity is associated with an anesthetic, an antibiotic, an antimalarial, a cardiac medication, a chemotherapeutic agent, a diuretic, a glucocorticosteroid, an immunomodulatory drug, a mucosal protectant, a narcotic analgesic, a non-steroidal anti-inflammatory drug (NSAID), a psychopharmacologic agent, a quinine, a toxic substance, a vapor or solvent, or a combination thereof.

8. The method of claim 1, wherein ototoxicity is associated with amikacin, amphotericin B, capreomycin, chloramphenicol, erythromycin, gentamycin, kanamycin, minocycline, polymyxin B, neomycin, netilimicin, streptomycin, a sulfonamide, tobramycin, vancomycin, chloroquine, hydroxychloroquine, celiprolol, flecainide, lidocaine, metoprolol, procainamide, propranolo, quinidine, bleomycine, bromocriptine, carboplatinum, cisplatin, methotrexate, nitrogen mustard, vinblastin, vincristine, acetazolamide, bendroflumethiazide, bumetadine, chlorthalidone, diapamide, ethacrynic acid, furosemide, hydrochlorthiazide, methylchlorthiazide, prednisolone, adrenocorticotrophic hormone (ACTH), thalidomide, misoprotol, hydrocodone, aspirin, acematacine, benorilate, benoxaprofen, carprofen, diclofenac, diflunisal, etocolac, fenoprofen, feprazon, ibuprofen, indomethacin, isoxicam, ketoprofen, methyl salicylates, naproxen, D-penicilliamin, phenylbutazone, piroxicam, proglumetacin, proquazon, rofecoxib, salicylates, sulindac, tolmetin, zomepirac, amitryptiline, alprazolam, clorazepate, chlordiazepoxide, diazepam, flurazepam, lorazepam, midazolam, oxazepam, prozepam, quazepam, temazepam, triazolam, bupropion, carbamzepine, diclofensine, doxepin, desiprimine, fluoxetin, imipramine, lithium, melitracen, molindon, paroxetin, phenelzin, protriptilin, trazodon, zimeldin, chloroquine phosphate, quinacrine hydrochloride, quinine sulfate, alcohol, arsenum, caffeine, lead, marijuana, nicotine, mercury, auronofin, cyclohexane, dichloromethane, hexane, lindane, methyl-chloride, methyl-n-butyl-ketone, perchlor-ethylene, styrene, tetrachlor-ethane, toluol, trichloroethylene, or a combination thereof.

* * * * *